US012286636B2

(12) United States Patent
Mason et al.

(10) Patent No.: US 12,286,636 B2
(45) Date of Patent: Apr. 29, 2025

(54) REPLICATING AND NON-REPLICATING VECTORS FOR RECOMBINANT PROTEIN PRODUCTION IN PLANTS AND METHOD OF USE THEREOF

(71) Applicant: ARIZONA BOARD OF REGENTS ON BEHALF OF ARIZONA STATE UNIVERSITY, Scottsdale, AZ (US)

(72) Inventors: Hugh Mason, Phoenix, AZ (US); Andrew Diamos, Tempe, AZ (US); Sun Hee Rosenthal, Santa Ana, CA (US)

(73) Assignee: Arizona Board of Regents on Behalf of Arizona, Scottsdale, AZ (US)

( * ) Notice: Subject to any disclaimer, the term of this patent is extended or adjusted under 35 U.S.C. 154(b) by 1189 days.

(21) Appl. No.: 16/976,739

(22) PCT Filed: Mar. 4, 2019

(86) PCT No.: PCT/US2019/020621

§ 371 (c)(1),
(2) Date: Aug. 28, 2020

(87) PCT Pub. No.: WO2019/169409

PCT Pub. Date: Sep. 6, 2019

(65) Prior Publication Data

US 2020/0407741 A1 Dec. 31, 2020

Related U.S. Application Data

(60) Provisional application No. 62/638,010, filed on Mar. 2, 2018.

(51) Int. Cl.
*C12N 15/82* (2006.01)

(52) U.S. Cl.
CPC ..... *C12N 15/8258* (2013.01); *C12N 15/8205* (2013.01); *C12N 15/822* (2013.01); *C12N 2750/12043* (2013.01)

(58) Field of Classification Search
None
See application file for complete search history.

(56) References Cited

U.S. PATENT DOCUMENTS

| | | | |
|---|---|---|---|
| 7,026,123 | B1 | 4/2006 | Duvick |
| 2014/0130205 | A1 | 5/2014 | Bhyri |
| 2015/0368660 | A1 | 12/2015 | Mason |
| 2017/0081676 | A1 | 3/2017 | Gupta |

OTHER PUBLICATIONS

U.S. Appl. No. 17/190,745, filed Mar. 3, 2021.*
Perez-Gonzalez and Caro. BMC Res Notes (2018) 11:511.*
Meshcheriakova, Y. A., Saxena, P., and Lomonossoff, G. P. (2014). Fine-tuning levels of heterologous gene expression in plants by orthogonal variation of the untranslated regions of a nonreplicating transient expression system. Plant Biotechnol. J. 12, 718-727. doi:10.1111/ pbi.12175.
Millevoi S, Vagner S (2009) Molecular mechanisms of eukaryotic pre-mRNA 3' end processing regulation Nucleic Acids Research 38:2757-2774 doi:10.1093/nar/gkp1176.
Mlynárová, L., Hricová, A., Loonen, A., and Nap, J.-P. (2003). The presence of a chromatin boundary appears to shield a transgene in tobacco from RNA silencing. Plant Cell 15, 2203-17. doi:10.1105/ tpc.012070.
Mogen BD, MacDonald MH, Graybosch R, Hunt AG (1990) Upstream Sequences Other than AAUAAA Are Required for Efficient Messenger RNA 3'-End Formation in Plants The Plant Cell 2:1261 doi:10.2307/3869344.
Moore MJ, Proudfoot NJ (2009) Pre-mRNA Processing Reaches Back to Transcription and Ahead to Translation Cell 136:688-700 doi:10.1016/j.cell.2009.02.001.
Mor, T. et al., "Geminivirus vectors for high-level expression of foreign proteins in plant cells", Biotechnology and Bioengineering, Feb. 2003 (available online Dec. 2002), vol. 81, No. 4, pp. 430-437 <DOI:10.1002/bit.10483>.
Nagaya S, Kawamura K, Shinmyo A, Kato K (2009) The HSP Terminator of *Arabidopsis thaliana* Increases Gene Expression in Plant Cells Plant and Cell Physiology 51:328-332 doi:10.1093/pcp/ pcp188.
Nandi, S. et al., "Techno-economic analysis of a transient plant-based platform for monoclonal antibody production", mAbs, Sep. 2016 (available online Aug. 2016), vol. 8, No. 8, pp. 1456-1466 <DOI:10.1080/19420862.2016.1227901>.
Narsai R, Howell KA, Millar AH, O'Toole N, Small I, Whelan J (2007) Genome-Wide Analysis of mRNA Decay Rates and Their Determinants in *Arabidopsis thaliana*. Plant Cell Online 19:3418-3436. doi: 10.1105/tpc.107.055046.

(Continued)

*Primary Examiner* — Medina A Ibrahim
(74) *Attorney, Agent, or Firm* — BOOTH UDALL Fuller, PLC; Rodney J. Fuller

(57) ABSTRACT

The present disclosure relates to plant-based recombinant protein production systems and their methods of production and use. The plant-based recombinant protein production system is a vector comprising a 5' UTR and a 3' UTR, wherein the 3' UTR comprises at least one terminator selected from the group consisting of: EU, IEU, NbACT3, NbACT617, NbACT567, Pin2, BDB501, BDB282, NbHSP, NbHSPb, Rep, RbcS, SIR, SIR 5'/3', SIR 3', AtHSP, 35S, RepA, NOS, TMV, TNVD, PEMV, and BYDV. In certain implementations, the vector comprises two terminators in the 3' UTR, where the two terminators are fused to form a double terminator. For example, the double terminator comprises two members selected from the group consisting of: EU, IEU, NbACT3, NbACT617, NbACT567, Pin2, BDB501, BDB282, NbHSP, NbHSPb, Rep, RbcS, SIR, SIR 5'/3', SIR 3', AtHSP, 35S, RepA, NOS, TMV, TNVD, PEMV, and BYDV. In some aspects, the vector further comprises a chromatin scaffold/matrix attachment region (MAR) that is downstream of the terminators.

13 Claims, 13 Drawing Sheets

Specification includes a Sequence Listing.

(56) References Cited

OTHER PUBLICATIONS

Olinger, G. G., Pettitt, J., Kim, D., Working, C., Bohorov, O., Bratcher, B., et al. (2012). Delayed treatment of Ebola virus infection with plant-derived monoclonal antibodies provides protection in rhesus macaques. Proc. Natl. Acad. Sci. U. S. A. 109, 18030-5. doi:10.1073/pnas.1213709109.

Pietrzak, M., Shillito, R. D., Hohn, T., and Potrykus, I. (1986). Expression in plants of two bacterial antibiotic resistance genes after protoplast transformation with a new plant expression vector. Nucleic Acids Res. 14, 5857-5868. doi:10.1093/nar/14.14.5857.

Qin, C., Shi, N., Gu, M., Zhang, H., Li, B., Shen, J., et al. (2012). Involvement of RDR6 in short-range intercellular RNA silencing in Nicotiana benthamiana. Sci. Rep. 2, 467. doi:10.1038/srep00467.

Qiu, X., Wong, G., Audet, J., Bello, A., Fernando, L., Alimonti, J. B., et al. (2014). Reversion of advanced Ebola virus disease in nonhuman primates with ZMapp. Nature 514, 47-53. doi:10.1038/nature13777.

Qu X, Lykke-Andersen S, Nasser T, Saguez C, Bertrand E, Jensen TH, Moore C (2009) Assembly of an Export-Competent mRNP Is Needed for Efficient Release of the 3'-End Processing Complex after Polyadenylation Molecular and Cellular Biology 29:5327-5338 doi:10.1128/mcb.00468-09.

Que, Q., Wang, H. Y., English, J. J., and Jorgensen, R. A. (1997). The Frequency and Degree of Cosuppression by Sense Chalcone Synthase Transgenes Are Dependent on Transgene Promoter Strength and Are Reduced by Premature Nonsense Codons in the Transgene Coding Sequence. Plant Cell 9, 1357-1368. doi:10.1105/tpc.9.8.1357.

Rethmeier N, Seurinck J, Van Montagu M, Cornelissen M (1997) Intron-mediated enhancement of transgene expression in maize is a nuclear, gene-dependent process The Plant Journal 12:895-899 doi:10.1046/j.1365-313x.1997.12040895.x.

Richter, L. J., Thanavala, Y., Arntzen, C. J., and Mason, H. S. (2000). Production of hepatitis B surface antigen in transgenic plants for oral immunization. Nat. Biotechnol. 18, 1167-71. doi:10.1038/81153.

Rose AB (2008) Intron-Mediated Regulation of Gene Expression. Springer Berlin Heidelberg. doi:10.1007/978-3-540-76776-3_15.

Rothnie HM, Chen G, Futterer J, Hohn T (2001) Polyadenylation in Rice Tungro Bacilliform Virus: cis-Acting Signals and Regulation Journal of Virology 75:4184-4194 doi:10.1128/jvi.75.9.4184-4194.2001.

Sainsbury, F. et al., "pEAQ: versatile expression vectors for easy and quick transient expression of heterologous proteins in plants", Plant Biotechnology Journal, Sep. 2009 (available online Aug. 2009), vol. 7, No. 7, pp. 682-693 <DOI:10.1111/j.1467-7652.2009.00434.x>.

Sainsbury, F., and Lomonossoff, G. P. (2008). Extremely high-level and rapid transient protein production in plants without the use of viral replication. Plant Physiol. 148, 1212-8. doi:10.1104/pp.108.126284.

Sanfacon H, Brodmann P, Hohn T (1991) A dissection of the cauliflower mosaic virus polyadenylation signal Genes & Development 5:141-149 doi:10.1101/gad.5.1.141.

Schubert, D., Lechtenberg, B., Forsbach, A., Gils, M., Bahadur, S., and Schmidt, R. (2004). Silencing in Arabidopsis T-DNA transformants: the predominant role of a gene-specific RNA sensing mechanism versus position effects. Plant Cell 16, 2561-72. doi:10.1105/tpc.104.024547.

Sharma AK, Sharma MK (2009) Plants as bioreactors: Recent developments and emerging opportunities Biotechnology Advances 27:811-832 doi:10.1016/j.biotechadv.2009.06.004.

Sheldon CC, Conn AB, Dennis ES, Peacock WJ (2002) Different Regulatory Regions Are Required for the Vernalization-Induced Repression of Flowering Locus C and for the Epigenetic Maintenance of Repression. Plant Cell Online 14:2527-2537. doi: 10.1105/tpc.004564.

Showalter AM, Keppler B, Lichtenberg J, Gu D, Welch LR (2010) A Bioinformatics Approach to the Identification, Classification, and Analysis of Hydroxyproline-Rich Glycoproteins Plant Physiology 153:485-513 doi:10.1104/pp.110.156554.

Sieburth LE, Meyerowitz EM (1997) Molecular Dissection of the AGAMOUS Control Region Shows That cis Elements for Spatial Regulation Are Located Intragenically The Plant Cell 9:355 doi:10.2307/3870487.

Simon, A. E., and Miller, W. A. (2013). 3' cap-independent translation enhancers of plant viruses. Annu. Rev. Microbiol. 67, 21-42. doi: 10.1146/annurev-micro-092412-155609.

Singh, G., Pratt, G., Yeo, G. W., and Moore, M. J. (2015). The Clothes Make the mRNA: Past and Present Trends in mRNP Fashion. Annu. Rev. Biochem. 84, 325-354. doi:10.1146/annurev-biochem-080111-092106.

Slomovic S, Schuster G (2013) Circularized RT-PCR (cRT-PCR). Elsevier. doi:10.1016/ b978-0-12-420037-1.00013-0.

Strasser, R. et al., "Controlled glycosylation of plant-produced recombinant proteins", Current Opinion in Biotechnology, Dec. 2014 (available online Jul. 2014), vol. 30, pp. 95-100 <DOI:10.1016/j.copbio.2014.06.008>.

Streatfield SJ (2007) Approaches to achieve high-level heterologous protein production in plants Plant Biotechnology Journal 5:2-15 doi:10.1111/j.1467-7652.2006.00216.x.

Tan-Wong SM et al. (2012) Gene Loops Enhance Transcriptional Directionality Science 338:671-675 doi:10.1126/science.1224350.

Tan-Wong SM, Wijayatilake HD, Proudfoot NJ (2009) Gene loops function to maintain transcriptional memory through interaction with the nuclear pore complex Genes & Development 23:2610-2624 doi:10.1101/gad.1823209.

Tian B, Manley JL (2013) Alternative cleavage and polyadenylation: the long and short of it Trends in Biochemical Sciences 38:312-320 doi:10.1016/j.tibs.2013.03.005.

Tokuhisa, J. G., Singh, K., Dennis, E. S., and Peacock, W. J. (1990). A DNA-Binding Protein Factor Recognizes Two Binding Domains within the Octopine Synthase Enhancer Element. Plant Cell 2, 215. doi:10.2307/3869136.

Tora L, Dantonel J-C, Murthy KGK, Manley JL (1997) Nature 389:399-402 doi: 10.1038/38763.

Tusé, D. et al., "Manufacturing Economics of Plant-Made Biologics: Case Studies in Therapeutic and Industrial Enzymes", BioMed Research International, May 2014, vol. 2014, article 256135, 16 pages <DOI:10.1155/2014/256135>.

Wigington, C. P., Williams, K. R., Meers, M. P., Bassell, G. J., and Corbett, A. H. (2014). Poly(A) RNA-binding proteins and polyadenosine RNA: new members and novel functions. Wiley Interdiscip. Rev. RNA 5, 601-622. doi:10.1002/wrna.1233.

Wolterink-van Loo, S., Escamilla Ayala, A. A., Hooykaas, P. J. J., and van Heusden, G. P. H. (2015). Interaction of the Agrobacterium tumefaciens virulence protein VirD2 with histones. Microbiology 161, 401-10. doi:10.1099/mic.0.083410-0.

Xing A, Moon BP, Mills KM, Falco SC, Li Z (2010) Revealing frequent alternative polyadenylation and widespread low-level transcription read-through of novel plant transcription terminators Plant Biotechnology Journal 8:772-782 doi:10.1111/j.1467-7652.2010.00504.x.

Zhang X, Mason H (2006) Bean Yellow Dwarf Virus replicons for high-level transgene expression in transgenic plants and cell cultures Biotechnology and Bioengineering 93:271-279 doi:10.1002/bit.20695.

Zhang, J., Lu, L., Ji, L., Yang, G., and Zheng, C. (2009). Functional characterization of a tobacco matrix attachment region-mediated enhancement of transgene expression. Transgenic Res. 18, 377-385. doi:10.1007/s11248-008-9230-3.

Zhao H, Xing D, Li QQ (2009) Unique features of plant cleavage and polyadenylation specificity factor revealed by proteomic studies. Plant Physiol 151:1546-56. doi: 10.1104/pp.09.142729.

Zhao J, Hyman L, Moore C (1999) Formation of mRNA 3' ends in eukaryotes: mechanism, regulation, and interrelationships with other steps in mRNA synthesis Microbiol Mol Biol Rev 63:405-445.

Zhao, C.-P., Guo, X., Chen, S.-J., Li, C.-Z., Yang, Y., Zhang, J.-H., et al. (2017). Matrix attachment region combinations increase

(56) References Cited

OTHER PUBLICATIONS transgene expression in transfected Chinese hamster ovary cells. Sci. Rep. 7, 42805. doi:10.1038/srep42805.
Zimran, A. et al., "Pivotal trial with plant cell-expressed recombinant glucocerebrosidase, taliglucerase alfa, a novel enzyme replacement therapy for Gaucher disease", Blood, Nov. 2011, vol. 118, No. 22, pp. 5767-5773 <DOI:10.1182/blood-2011-07-366955>.
Ali S, Taylor WC (2001) The 3' non-coding region of a C4 photosynthesis gene increases transgene expression when combined with heterologous promoters Plant Mol Biol 46:325-333.
Allen, E., and Howell, M. D. (2010). miRNAs in the biogenesis of trans-acting siRNAs in higher plants. Semin. Cell Dev. Biol. 21, 798-804. doi:10.1016/j.semcdb.2010.03.008.
Allen, G. C., Hall, G., Michalowski, S., Newman, W., Spiker, S., Weissinger, A. K., et al. (1996). High-Level Transgene Expression in Plant Cells□: Effects of a Strong Scaffold Attachment Region from Tobacco. Plant Cell 8, 899-913. doi:10.1105/tpc.8.5.899.
Arntzen CJ (2008) Plant science. Using tobacco to treat cancer Science 321:1052-1053 doi:10.1126/science.1163420.
Andersen, P. K., Lykke-Andersen, S., and Jensen, T. H. (2012). Promoter-proximal polyadenylation sites reduce transcription activity. Genes Dev. 26, 2169-2179. doi:10.1101/gad.189126.112.
Arntzen CJ (2008) Plant science. Using tobacco to treat cancer Science 321:1052-1053 doi:10.1126/science.1163420.
Baeg K, Iwakawa H, Tomari Y (2017) The poly(A) tail blocks RDR6 from converting self mRNAs into substrates for gene silencing. Nat Plants 3:17036. doi: 10.1038/nplants.2017.36.
Béclin, C., Boutet, S., Waterhouse, P., and Vaucheret, H. (2002). A branched pathway for transgene-induced RNA silencing in plants. Curr. Biol. 12, 684-688. doi:10.1016/S0960-9822(02)00792-3.
Bombarely A, Rosli HG, Vrebalov J, Moffett P, Mueller LA, Martin GB (2012) A Draft Genome Sequence of Nicotiana benthamianato Enhance Molecular Plant- Microbe Biology Research. Mol Plant-Microbe Interact 25:1523-1530. doi:10.1094/mpmi-06-12-0148-ta.
Calikowski, T. T., Meulia, T., and Meier, I. (2003). A proteomic study of the arabidopsis nuclear matrix. J. Cell. Biochem. 90, 361-78. doi:10.1002/jcb.10624.
Carrington JC, Freed DD, Leinicke AJ (1991) Bipartite Signal Sequence Mediates Nuclear Translocation of the Plant Potyviral NIa Protein The Plant Cell 3:953 doi:10.2307/3869157.
Chen, Q. et al., "The potential of plants as a system for the development and production of human biologics", F1000 Research, May 2016, vol. 5, No. 912, 8 pages <DOI:10.12688/f1000research.8010.1>.
Chung BYW, Simons C, Firth AE, Brown CM, Hellens RP "Effect of 5'UTR introns on gene expression in *Arabidopsis thaliana*" (2006) BMC Genomics 7:120 doi:10.1186/1471-2164-7-120.
Collens JI, Mason HS, Curtis WR (2008) Agrobacterium-Mediated Viral Vector-Amplified Transient Gene Expression in Nicotiana glutinosa Plant Tissue Culture Biotechnology Progress 23:570-576 doi:10.1021/bp060342u.
D'Aoust, M.-A., Couture, M. M.-J., Charland, N., Trépanier, S., Landry, N., Ors, F., et al. (2010). The production of hemagglutinin-based virus-like particles in plants: a rapid, efficient and safe response to pandemic influenza. Plant Biotechnol. J. 8, 607-19. doi:10.1111/j.1467-7652.2009.00496.x.
Dong H et al. (2007) An exploration of 3'-end processing signals and their tissue distribution in Oryza sativa Gene 389:107-113 doi:10.1016/j.gene.2006.10.015.
Fan, Q., Treder, K., and Miller, W. A. (2012). Untranslated regions of diverse plant viral RNAs vary greatly in translation enhancement efficiency. BMC Biotechnol. 12, 22. doi:10.1186/1472-6750-12-22.
Fernandez-Pozo, N., Menda, N., Edwards, J. D., Saha, S., Tecle, I. Y., Strickler, S. R., et al. (2015). The Sol Genomics Network (SGN)—from genotype to phenotype to breeding. Nucleic Acids Res. 43, D1036-41. doi:10.1093/nar/gku1195.
Fox, J. L. (2012). First plant-made biologic approved. Nat. Biotechnol. 30, 472-472. doi:10.1038/nbt0612-472.Francis KE, Spiker S (2004) Identification of *Arabidopsis thaliana* transformants without selection reveals a high occurrence of silenced T-DNA integrations The Plant Journal 41:464-477 doi:10.1111/j.1365-313x.2004.02312.x.
Francis KE, Spiker S (2004) Identification of *Arabidopsis thaliana* transformants without selection reveals a high occurrence of silenced T-DNA integrations The Plant Journal 41:464-477 doi:10.1111/j.1365-313x.2004.02312.x.
Gilmartin GM (2005) Eukaryotic mRNA 3' processing: a common means to different ends Genes & Development 19:2517-2521 doi:10.1101/gad.1378105.
Gleba YY, TuséD, Giritch A (2014) Plant viral vectors for delivery by Agrobacterium. In: Current Topics in Microbiology and Immunology. pp. 155-192.
Hiatt, A. et al., "Glycan variants of a respiratory syncytial virus antibody with enhanced effector function and in vivo efficacy", Proceedings of the National Academy of Sciences of the United States of America, Apr. 2014, vol. 111, No. 16, pp. 5992-5997 <DOI:10.1073/pnas.1402458111>.
Hirsinger C, Parmentier Y, Durr A, Fleck J, Jamet E (1997) Plant Molecular Biology 33:279-289 doi:10.1023/a:1005738815383.
Hori K, Watanabe Y (2007) Context analysis of termination codons in mRNA that are recognized by plant NMD. Plant Cell Physiol 48:1072-8. doi:10.1093/pcp/pcm075.
Huang, Z. et al., "A DNA replicon system for rapid high-level production of virus-like particles in plants", Biotechnology and Bioengineering, Jul. 2009 (available online Feb. 2009), vol. 103, No. 4, pp. 706-714 <DOI:10.1002/bit.22299>.
Huang, Z. et al., "Conformational analysis of hepatitis B surface antigen fusions in an Agrobacterium-mediated transient expression system", Plant Biotechnology Journal, May 2004 (available online Mar. 2004), vol. 2, No. 3, pp. 241-249 <DOI:10.1111/j.1467-7652.2004.00068.x>.
Huang, Z., Phoolcharoen, W., Lai, H., Piensook, K., Cardineau, G., Zeitlin, L., et al. (2010). High-level rapid production of full-size monoclonal antibodies in plants by a single-vector DNA replicon system. Biotechnol. Bioeng. 106, 9-17. doi:10.1002/bit.22652.
Hunt AG (2008) Messenger RNA 3' end formation in plants. Curr. Top. Microbiol. Immunol. 326:151-177 doi:10.1007/978-3-540-76776-3_9.
Ingelbrecht LW, Herman LMF, Dekeyser RA, Montagu MC Van, Depicker AG (1989) Different 3' End Regions Strongly Influence the Level of Gene Expression in Plant Cells. Plant Cell 1:671-680 doi:10.1105/tpc.1.7.671.
Ji G, Zheng J, Shen Y, Wu X, Jiang R, Lin Y, Loke JC, Davis KM, Reese GJ, Li QQ (2007) Predictive modeling of plant messenger RNA polyadenylation sites. BMC Bioinformatics 8:43. doi: 10.1186/1471-2105-8-43.
Jiang X, Wang M, Graham DY, Estes MK (1992) Expression, self-assembly, and antigenicity of the Norwalk virus capsid protein J Virol 66:6527-6532.
Kato H, Xie G, Sato Y, Imai R (2010) Isolation of Anther-specific Gene Promoters Suitable for Transgene Expression in Rice. Plant Mol Biol Report 28:381-387. doi: 10.1007/s11105-009-0162-8.
Kertész S, Kerényi Z, Mérai Z, Bartos I, Pálfy T, Barta E, Silhavy D (2006) Both introns and long 3'-UTRs operate as cis-acting elements to trigger nonsense-mediated decay in plants Nucleic Acids Research 34:6147-6157 doi:10.1093/nar/gkl737.
Kooiker M, Airoldi CA, Losa A, Manzotti PS, Finzi L, Kater MM, Colombo L (2005) Basic Pentacysteine1, a GA binding protein that induces conformational changes in the regulatory region of the homeotic Arabidopsis gene Seedstick. Plant Cell 17:722-729. doi: 10.1105/tpc.104.030130.
Lacroix, B., Loyter, A., and Citovsky, V. (2008). Association of the Agrobacterium T-DNA-protein complex with plant nucleosomes. Proc. Natl. Acad. Sci. 105, 15429-15434. doi:10.1073/pnas.0805641105.
Lai, H., He, J., Engle, M., Diamond, M. S., and Chen, Q. (2012). Robust production of virus-like particles and monoclonal antibodies with geminiviral replicon vectors in lettuce. Plant Biotechnol. J. 10, 95-104. doi:10.1111/j.1467-7652.2011.00649.x.
Libri D, Dower K, Boulay J, Thomsen R, Rosbash M, Jensen TH (2002) Interactions between mRNA export commitment, 3'-end quality control, and nuclear degradation. Mol Cell Biol 22:8254-8266. doi: 10.1128/MCB.22.23.8254- 8266.2002.

(56) References Cited

OTHER PUBLICATIONS

Liebich, I., Bode, J., Reuter, I., and Wingender, E. (2002). Evaluation of sequence motifs found in scaffold/matrix-attached regions (S/MARs). Nucleic Acids Res. 30, 3433-3442. doi:10.1093/nar/gkf446.

Limkul, J., Misaki, R., Kato, K., and Fujiyama, K. (2015). The combination of plant translational enhancers and terminator increase the expression of human glucocerebrosidase in Nicotiana benthamiana plants. Plant Sci. 240, 41-49. doi:10.1016/j.plantsci.2015.08.018.

Loke JC (2005) Compilation of mRNA Polyadenylation Signals in Arabidopsis Revealed a New Signal Element and Potential Secondary Structures. Plant Physiol 138:1457-1468. doi: 10.1104/pp.105.060541.

Lomonossoff GP, D'Aoust M-A (2016) Plant-produced biopharmaceuticals: A case of technical developments driving clinical deployment. Science 353:1237-40. doi: 10.1126/science.aaf6638.

Luo Z, Chen Z (2007) Improperly terminated, unpolyadenylated mRNA of sense transgenes is targeted by RDR6-mediated RNA silencing in Arabidopsis. Plant Cell 19:943-58. doi: 10.1105/tpc.106.045724.

Lyon, G. M., Mehta, A. K., Varkey, J. B., Brantly, K., Plyler, L., McElroy, A. K., et al. (2014). Clinical Care of Two Patients with Ebola Virus Disease in the United States. N. Engl. J. Med. 371, 2402-2409. doi: 10.1056/nejmoa1409838.

Macfarlane, S. A., Gilmer, D., and Davies, J. W. (1992). Efficient inoculation with CaMV 35 S promoter-driven DNA clones of the tobravirus PEBV. Virology 187, 829-831. doi:10.1016/0042-6822(92)90488-b.

Mandel CR, Bai Y, Tong L (2007) Protein factors in pre-mRNA 3'-end processing Cellular and Molecular Life Sciences 65:1099-1122 doi:10.1007/s00018-007-7474-3.

Mankin, S. L., Allen, G. C., Phelan, T., Spiker, S., and Thompson, W. F. (2003). Elevation of transgene expression level by flanking matrix attachment regions (MAR) is promoter dependent: a study of the interactions of six promoters with the RB7 3' MAR. Transgenic Res 12, 3-12. Available at: http://www.ncbi.nlm.nih.gov/pubmed/12650520.

Mapendano CK, Lykke-Andersen S, Kjems J, Bertrand E, Jensen TH (2010) Crosstalk between mRNA 3' End Processing and Transcription Initiation Molecular Cell 40:410-422 doi:10.1016/j.molcel.2010.10.012.

Mason HS, Ball JM, Shi JJ, Jiang X, Estes MK, Arntzen CJ (1996) Expression of Norwalk virus capsid protein in transgenic tobacco and potato and its oral immunogenicity in mice Proceedings of the National Academy of Sciences 93:5335-5340 doi:10.1073/pnas.93.11.5335.

Mathew LG, Maloney B, Takeda N, Mason HS (2011) Spurious polyadenylation of Norovirus Narita 104 capsid protein mRNA in transgenic plants Plant Molecular Biology 75:263-275 doi:10.1007/s11103-010-9725-1.

Menossi M, Rabaneda F, Puigdomenech P, Martinez-Izquierdo JA (2003) Analysis of regulatory elements of the promoter and the 3' untranslated region of the maize Hrgp gene coding for a cell wall protein Plant Cell Rep 21:916-923 doi:10.1007/s00299-003-0602-0.

Beyene et al., "Unprecedented enhancement of transient gene expression from minimal cassettes using a double terminator", Plant Cell Rep, (Oct. 22, 2010), vol. 30, doi:doi:10.1007/s00299-010-0936-3, pp. 13-25, XP019869854.

Diamos et al., "5' and 3' Untranslated Regions Strongly Enhance Performance of Geminiviral Replicons in Nicotiana benthamiana Leaves", Front Plant Sci, (Feb. 24, 2016), vol. 7, No. 200, pp. 1-15.

Diamos et al., "Chimeric 3' flanking regions strongly enhance gene expression in plants", Plant Biotechnol J, (May 21, 2018), vol. 16, pp. 1971-1982.

Diamos, A.G., "Chimeric 3' flanking regions strongly enhance gene expression in plants", Optimization of a Viral System to Produce Vaccines and other Biopharmaceuticals in Plants, Doctoral Thesis, (Dec. 31, 2017), pp. 86-132, URL: https://repository.asu.edu/attachments/194162/content/Diamos_asu_0010E_17585.pdf, (May 20, 2019).

Diamos, Andy (Doctoral Dissertation on Optimization of a Viral System to Produce Vaccines and Other Biophrmaceuticals in plants, Dec. 2017) (Year: 2017).

Halweg et al., "The Rb7 matrix attachment region increases the likelihood and magnitude of transgene expression in tobacco cells: a flow cytometric study", Plant Cell, (Jan. 19, 2005), vol. 17, doi:doi:10.1105/tpc.104.028100, pp. 418-429, XP002442315.

Ji et al., "TM6, a novel nuclear matrix attachment region, enhances its flanking gene expression through influencing their chromatin structure", Mol Cells, (Jul. 12, 2013), vol. 36, doi:doi: 10.1007/s10059-013-0092-z, pp. 127-137, XP055354122.

Rosenthal et al., "An intronless form of the tobacco extensin gene terminator strongly enhances transient gene expression in plant leaves", Plant Mol Biol, (Feb. 10, 2018), vol. 96, pp. 429-443.

Stewart et al (JBC, 2006, 281(32): 22665-22673) (Year: 2006).

* cited by examiner

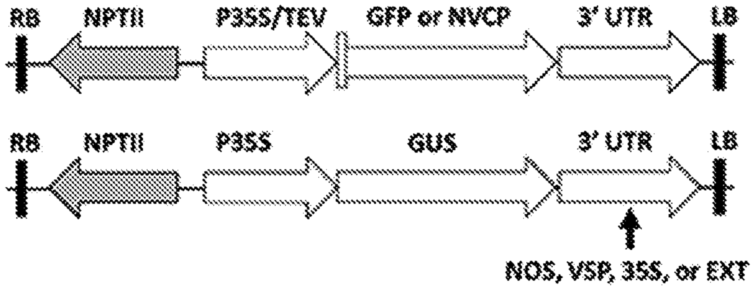
Fig. 1A
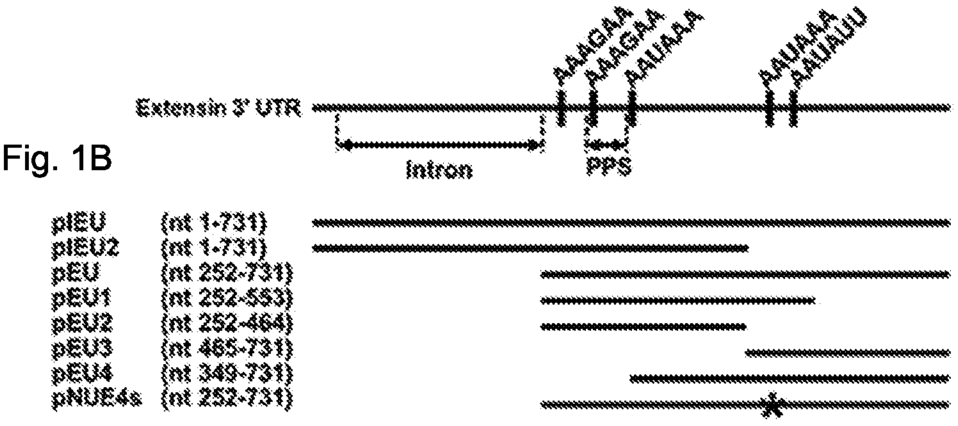
Fig. 1B
Fig. 2A
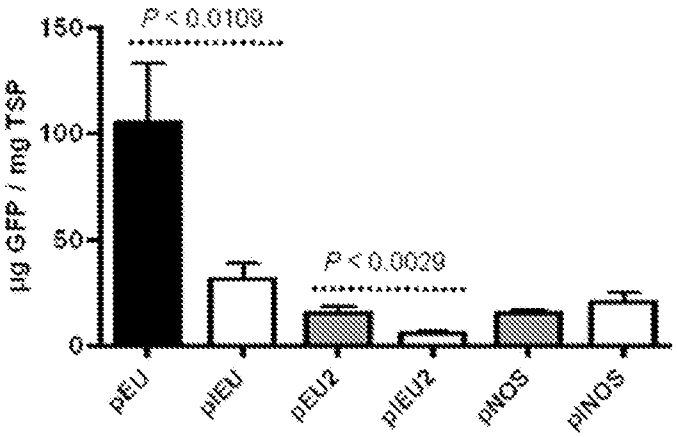
Fig. 2B
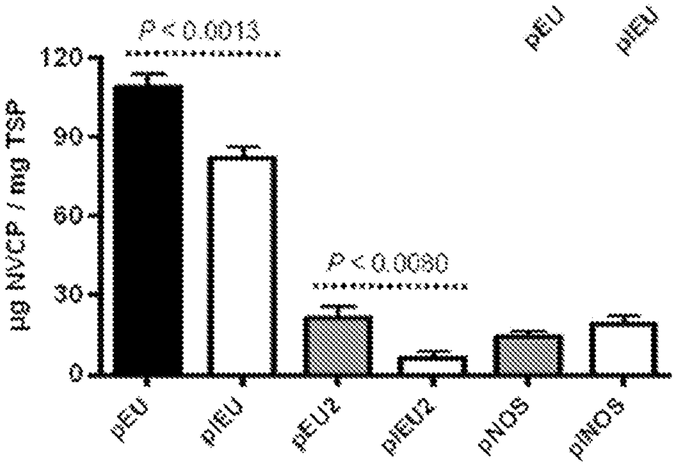

Fig. 5A

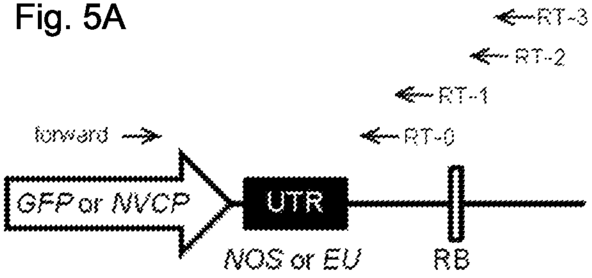

Fig. 5B

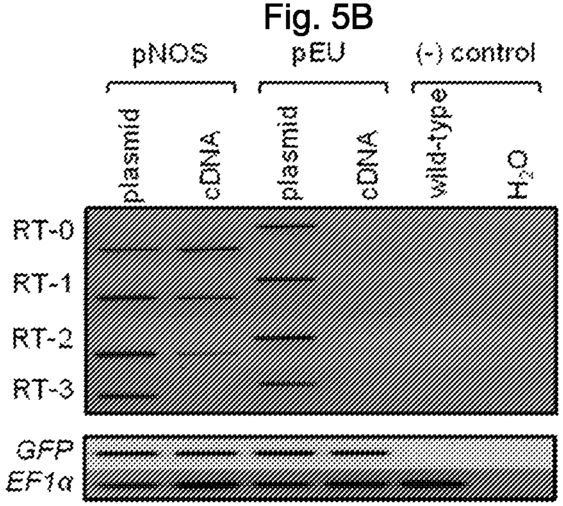

Fig. 5C

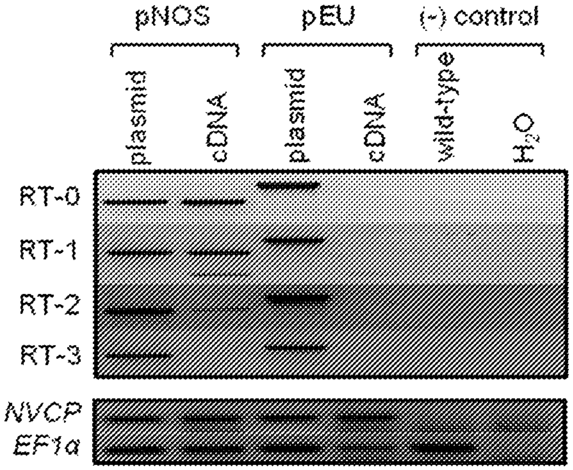

Fig. 6

```
                      NUE1
252 ~ caaagcagaatgctgagctaaaagaaaggctttttccattttcgagagac
             NUE2   Polypurine Sequence (PPS)
302 ~ aatgagaaaagaagaagaagaagaagaagaagaagaagaagaaaagagta
         NUE3
352 ~ aataataaagccccacaggaggcgaagttcttgtagctccatgttatcta
                        pA(2)
402 ~ agttattgatattgtttgccctatattttatttctgtcattgtgtatgtt
                                                  NUE4
452 ~ ttgttcagtttcgatctccttgcaaaatgcagagattatgagatgaataa
                              NUE5
                  pA(3)       pA(9)
502 ~ actaagttatattattatacgtgttaatattctcctcctctctctagcta
552 ~ gccttttgttttctctttttcttatttgatttctttaaatcaatccatt
602 ~ ttaggagaggggccagggagtgatccagcaaaacatgaagattagaagaaa
652 ~ cttccctcttttttttcctgaaaacaatttaacgtcgagatttatctctt
702 ~ tttgtaatggaatcatttctacagttatgacg
```

Fig. 7

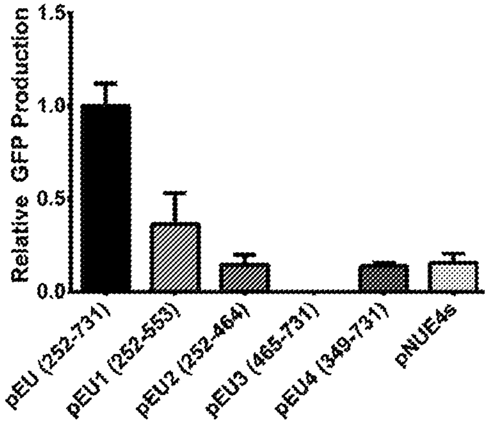

Stain-free Gel

REPLICATING AND NON-REPLICATING VECTORS FOR RECOMBINANT PROTEIN PRODUCTION IN PLANTS AND METHOD OF USE THEREOF

CROSS REFERENCE TO RELATED APPLICATIONS

This application is the U.S. National Stage of International Application No. PCT/US2019/020621, filed Mar. 4, 2019, which claims the benefit of U.S. Provisional Patent Application No. 62/638,010, filed Mar. 2, 2018, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 104,506 byte ASCII (text) file named "SeqList" created on Mar. 1, 2019.

TECHNICAL FIELD

The disclosure relates to plant-based recombinant protein production systems and their methods of production and use.

BACKGROUND

Plant-based recombinant protein production systems are have emerged as promising alternatives to traditional mammalian and microbial cell culture systems due to unique advantages of lower costs, high scalability, and improved safety (Chen and Davis 2016; Kamarova et al., 2010). Case studies have shown the potential for large cost reductions in capital investment and the cost of goods for plant-made therapeutics compared to conventional methods (Tusé et al., 2014; Nandi et al., 2016). The capacity for these systems to rapidly and safely produce therapeutics has been demonstrated by two success stories: the FDA approval of an enzyme replacement therapy for Gaucher's disease, which became the first plant-made therapeutic (Zimran et al., 2011; Fox 2012); and the monoclonal antibody therapy ZMapp given during the 2014 Ebola outbreak, which was shown to protect against lethal virus challenge (Lyon et al., 2014; Qui et al., 2014). Many strategies for improving protein production in plants have been explored, such as viral expression systems, subcellular targeting, *agrobacterium* strain, expression host, promoters, introns, and 5' untranslated regions (UTR). However, another key component in many of these systems is the gene terminator and surrounding regions, which have not been systematically optimized.

SUMMARY

The disclosure relates to plant-based recombinant protein production systems. In one aspect, the plant-based recombinant protein production system is a plant expression vector comprising at least one expression cassette. In some aspects, the disclosure relates to 3' UTRs that can be used in the expression cassettes disclosed herein.

The at least one expression cassette comprises a 5' UTR and a 3' UTR, wherein the 3' UTR comprises a first terminator; and a second terminator, a chromatin scaffold/matrix attachment region (MAR), or both. In some embodiments, the first terminator and the second terminator form a double terminator. In some embodiments, the 3' UTR further comprises MAR. In some aspects, MAR is downstream of the double terminator, while in other aspects, MAR is downstream of the first terminator. In certain implementations, the double terminator increases protein expression from the expression cassette.

In some embodiments, the first terminator is intronless tobacco extension terminator (EU) and the second terminator is selected from the group consisting of: *Nicotiana benthamiana* actin 3' UTR (NbACT3), p19 suppressor of RNA silencing from tomato bushy stunt virus (P19), *N. benthamiana* 18.8 kDa class II heat shock protein 3' UTR (NbHSP), short intergenic region of bean yellow dwarf virus (SIR), *agrobacterium* nopaline synthase 3' UTR (NOS), cauliflower mosaic virus 35S 3' UTR (35S), tobacco mosaic virus 3' UTR (TMV), BDB501 (bean dwarf mosaic virus DNA B nuclear shuttle protein 3' UTR, the intergenic region, the 3' end of the movement protein, and additional 200 nt downstream of the movement protein sequence), tobacco necrosis virus-D 3' UTR (TNVD), pea enation mosaic virus 3' UTR (PEMV), and barley yellow dwarf virus 3' UTR (BYDV). In some aspects, EU is upstream of the second terminator. Where the second terminator is 35S, 35S is upstream of EU in some embodiments.

In some embodiments, the first terminator is intron-containing tobacco extension terminator (IEU) and the second terminator is selected from the group consisting of: SIR, 35S, and long intergenic region from bean yellow dwarf virus (LIR). In some aspects, IEU is upstream of the second terminator.

In some embodiments, the at least one expression cassette comprises a 5' UTR and a 3' UTR, wherein the 3' UTR comprises a first terminator and MAR. In some aspects, the 3' UTR comprises EU and the MAR is selected from the group consisting of: Rb7 and TM6. In other aspects, the 3' UTR comprises IEU and the MAR is selected from the group consisting of: Rb7 and TM6. In certain embodiments, the 3' UTR of the at least one expression cassette comprises the first terminator, the second terminator, and MAR. In one embodiment, the 3' UTR comprises IEU, 35S, and Rb7, wherein IEU is upstream of 35S. In other embodiments, the 3' UTR comprises EU. In one aspect, such 3' UTR comprises EU, 35S, and Rb7, wherein EU is downstream or upstream of 35S. In another aspect, such 3' UTR comprises EU, NbACT3, and Rb7, wherein EU is upstream of NbACT3. In still another aspect, such 3' UTR comprises EU, BD501, and Rb7, wherein EU is upstream of BD501. In yet another aspect, such 3' UTR comprises EU, *A. thaliana* heat shock protein 3' UTR (AtHSP), and Rb7, wherein EU is downstream of AtHSP. In another aspect, such 3' UTR comprises EU, 35S, and TM6, wherein EU is upstream of 35S.

In another embodiment, the plant expression vector comprises an expression cassette with 3' UTR comprising at least one terminator selected from the group consisting of: EU, IEU, NbACT3, NbACT617 (downstream 617-nt region of NbACT3), NbACT567 (downstream 567 nt of NbACT3), Pin2, BDB501, BDB282 (282 nucleotides comprising bean dwarf mosaic virus DNA B nuclear shuttle protein 3' UTR, the intergenic region, and the 3' end of the movement protein), NbHSP, NbHSPb (NbHSP missing 75 nt from 5' end), bean dwarf mosaic virus rep gene 3' UTR (Rep), pea rubisco small subunit 3' UTR (RbcS), SIR, SIR 5'/3' (SIR with additional sequences both upstream and downstream), SIR 3' (SIR with its additional downstream viral sequence), AtHSP, 35S, bean dwarf mosaic virus repA gene 3' UTR (RepA), NOS, TMV, TNVD, PEMV, and BYDV. In some aspects, the 3' UTR comprises at least one terminator selected from the group consisting of: NbACT3, NbACT617, NbACT567, Pin2, BDB501, BDB282, NbHSP, NbHSPb, Rep, RbcS, SIR, SIR 5'/3', SIR 3', AtHSP, and RepA. In some implementations, the 3' UTR comprises a double terminator, wherein the double terminator is a fusion of two members selected from the group consisting of: EU, IEU, NbACT3, NbACT617, NbACT567, Pin2, BDB501, BDB282, NbHSP, NbHSPb, Rep, RbcS, SIR, SIR 5'/3', SIR 3', AtHSP, 35S, RepA, NOS, TMV, TNVD, PEMV, and BYDV. For example, the 3' UTR comprises a double terminator, wherein the double terminator is a fusion of two members selected from the group consisting of: EU, IEU, NbACT3, NbACT617, NbACT567, Pin2, BDB501, BDB282, NbHSP, NbHSPb, Rep, RbcS, SIR, SIR 5'/3', SIR 3', AtHSP, 35S, RepA, NOS, TMV, TNVD, PEMV, and BYDV. In some aspects, the 3' UTR comprises EU and a second terminator selected from the group consisting of: NbACT, P19, NbHSP, SIR, NOS, 35S, TMV, BDB501, TNVD, PEMV, and BYDV, wherein EU is upstream of the second terminator in some embodiments. In other aspects, the 3' UTR comprises 35S and a second terminator selected from the group consisting of: NbACT3, NOS, EU, NbHSP, Pin2, and BDB501, wherein in 35S is upstream of the second terminator in some embodiments. In some embodiments, the 3' UTR comprises 35S and NOS, wherein NOS is upstream of 35S. in some aspects, the 3' UTR comprises NbHSP and a second terminator selected from the group consisting of: NbACT3, NOS, and Pin2, wherein NbHSP is upstream of the second terminator in some embodiments.

In some implementations of the plant expression vector, the 3' UTR further comprises a chromatin scaffold/matrix attachment region (MAR) that is downstream of the terminators. In certain embodiments, the MAR is Rb7 or TM6. In some embodiments, the 3' UTR comprises Rb7 downstream of EU, IEU, AtHSp, 35S, BDB501, NbHSP, NOS, or NbACT3. In other embodiments, the 3' UTR comprises TM6 downstream of IEU, 35S, or NbACT3. In some aspects, the 3' UTR comprises RB7 downstream of a double terminator selected from the group consisting of: 35S+NbACT3, EU+35S, EU+NbACT3, NbHSP+NbACT3, 35S+EU, AtHSP+NOS, 35S+NOS, EU+BDB501, AtHSP+NbHSP, NbHSP+NOS, AtHSP+EU, NbHSP+Pin2, and IEU+35S. In other aspects, the 3' UTR comprises TM6 downstream of a double terminator selected from the group consisting of: EU+35S, 35S+NOS, NbHSP+NOS, and NbHSP+Pin2.

The disclosure also relates to the method of using the aforementioned plant-based recombinant protein production systems. In one implementation the vector described above are introduced into a plant or plant part. In some aspects, the plant is tobacco or lettuce or the plant part is from tobacco or lettuce. The some implementations, the vector transforms the plant or plant part using *agrobacterium*, for example, *Agrobacterium tumefaciens.*

BRIEF DESCRIPTION OF THE DRAWINGS

FIGS. 1A and 1B, in accordance with certain embodiments, depict schematics of the vector and constructs described herein. FIG. 1A shows a generalized schematic representation of the T-DNA regions of the vectors encoding Norwalk virus capsid protein (NVCP), green fluorescent protein (GFP), or β-glucuronidase (GUS). Different terminators are placed downstream of gene of interest. As used in FIG. 1A, P35S/TEV5' refers to the CaMV 35S promoter with tobacco etch virus 5' UTR. NOS refers to the *Agrobacterium* nopaline synthase gene 3' element. VSP refers to the soybean vspB gene 3' element. 35S refers to the CaMV 35S terminator. EU refers to the intronless tobacco extensin gene terminator. LB and RB refer to the left and right borders, respectively, of the T-DNA region. NPTII refers to the expression cassette encoding nptII gene for kanamycin resistance. FIG. 1B depicts constructs containing various lengths of the extension (Ext) terminator used in the examples (GenBank accession no. D13951, 1-731 nt). In the top portion, the vertical black bars indicate the putative near upstream elements (NUEs). The positions of intron and polypurine sequence (PPS) are indicated with arrows. The bottom portion show the regions of Ext terminator fused downstream of the GFP gene in deletion constructs and are aligned with the map in the top portion. The numbers in parentheses indicate the portion of the Ext terminator used for each construct. As used in FIG. 1B and also in FIGS. 2A-9B (unless specified otherwise), IEU refers to the portion of the Ext terminator that contains the intron while EU refers to the portion of the Ext terminator that lack the intron.

FIGS. 2A and 2B, in accordance with certain embodiments, depict the influence of the Ext intron (nt 24-249) on gene expression with either the Ext or NOS terminator. FIG. 2A shows GFP expression as determined by fluorometric analysis from three independently infiltrated samples and normalized by total soluble protein as measured by Bradford assay. FIG. 2B shows NVCP expression as measured by ELISA from six independent samples. White or filled bars represent constructs with or without intron, respectively. Data shown are means±S.D. P-values were determined by student's t test.

FIG. 3A depicts fluorometric analysis of GFP expression from constructs using different terminators. Infiltrated leaf extracts were analyzed by spectrofluorimetry and normalized by total soluble protein as measured by Bradford assay. The inset image is exemplary visualization of GFP expression. Infiltrated leaf was examined at 2 days post infiltration (DPI) under UV illumination (365 nm) generated by a B-100AP lamp (UVP). FIG. 3B shows NVCP expression from constructs with different terminators. FIG. 3C shows GUS expression from constructs using different terminators. Data shown are means±S.D. from six independently infiltrated samples.

FIGS. 4A and 4B respectively depict the relative mRNA accumulation of GFP and NVCP. Each sample was measured in triplicate for each transcript of interest. Elongation factor (EF1a) transcript served as the internal control. Transcript levels of GFP, NVCP and EF1a were quantified using separate standard curves and then the mRNA copy numbers of GFP and NVCP were normalized against the mRNA copy numbers of EFla. Data shown are means±S.D. from three independently infiltrated samples.

FIGS. 5A-5C, in accordance with certain embodiments, show that the Ext terminator is a highly efficient mediator of transcription termination. FIG. 5A depicts a portion of the T-DNA region of the constructs used in the study. The *Agrobacterium* nopaline synthase gene 3' element (NOS) or Ext terminator (indicated as EU in FIGS. 5A-5C) is placed downstream of the GFP or NVCP gene. RB refers to the right border of the T-DNA region. The horizontal arrows indicate primer regions used for the transcription read-through detection by RT-PCR. Agarose gel electrophoresis of RT-PCR product to check transcription readthrough using constructs with GFP gene (FIG. 5B) or NVCP gene (FIG. 5C). Template types are indicated. cDNA of wild-type leaf sample and $H_2O$ were used for negative (−) control. A gene specific forward primer was used with different reverse sense primers, which bind to different regions downstream of the terminator, indicated on the left of upper portion of FIG. 5A. To check RNA quality, RT-PCR was performed on the same RNA samples with GFP (FIG. 5B) or NVCP (FIG. 5C) and EF1a (FIGS. 5B and C) primer sets.

FIG. 6 identifies the poly(A) sites of the Ext terminator. The RNA samples from construct pPS-OGFPEU were decapped, circularized, reverse transcribed, PCR amplified, cloned, and sequenced. The cDNA sequence of the intronless Ext 3' UTR are shown (SEQ ID NO. 6 lacking all but two nucleotides from the pair of extraneous sequences). The putative NUEs are underlined and bold. The polypurine sequence (PPS) in the Ext terminator is shown in gray. The text "pA" is used to indicate the polyadenylation YA dinucleotide, followed by the number of sequenced clones in parentheses.

FIG. 7, in accordance with certain embodiments, show that influence of deletions in the Ext terminator on gene expression. Modified terminators were placed downstream of the GFP gene. Agroinfiltrated *N. benthamiana* leaves were harvested at 3 DPI and extracts were analyzed by SDS-PAGE followed by observation under UV illumination (365 nm) and by Coomassie staining. GFP band intensity was quantified using ImageJ software, using native plant proteins as a loading control. Data shown are means±standard error of three independently infiltrated leaves. All leaves were infiltrated with construct pEU as an internal control for leaf and plant variability.

FIG. 8A depicts a diagram of Ext terminator regions used in PPS testing constructs. Modified terminators are placed downstream of GFP gene. The positions of the putative NUEs and PPS are indicated with vertical bars and arrow, respectively. Deleted (pEUd) or substituted (pEUs) regions are indicated with discontinuous or dotted lines, respectively. FIG. 8B depicts the GFP expression relative to the reference construct pNOS. Test constructs were infiltrated side-by-side with reference construct pNOS and leaf extract were analyzed by spectrofluorimetry. Values from fluorometric analyses were converted to μg GFP/mg TSP and then normalized against the GFP expression of pNOS (indicated by dotted line). Asterisks denote a statistically significant reduction in GFP expression compared to pEU (Student's t test, $P<0.05$). Absolute mean value of pEU was 112.3 μg GFP/mg TSP. Data shown are means±S.D. from four to five independently infiltrated samples.

FIG. 10A depicts generalized schematic representation of the T-DNA region of the vectors used in this study. RB and LB refers to the right and left borders of the T-DNA region, respectively. NPTII refers to the kanamycin resistance cassette. P35S refers to the 35S promoter from cauliflower mosaic virus. TMV refers to the 5' UTR from tobacco mosaic virus. The 3' UTR is either a single terminator, double terminator, matrix attachment region, or combination of these elements as described in each experiment. FIG. 10B depicts the relative GFP production of nonreplicating vectors containing various 3' UTRs, which is inserted downstream from the GFP gene. The nonreplicating vectors were agroinfiltrated into *N. benthamiana* leaves. Leaves were photographed at 5 DPI under UV illumination (365 nm). The inset photo depicts a representative infiltrated leaf. Agroinfiltrated leaves were harvested between 4-5 DPI and extracts were analyzed by SDS-PAGE followed by observation under UV illumination (365 nm) and Coomassie staining. GFP band intensity was quantified using ImageJ software, using native plant protein bands as a loading control. Data shown are means±standard error of 3-4 independently infiltrated leaves. EU refers to intronless tobacco extensin 3' UTR. As used in FIGS. 10B-17B, IEU refers to intron-containing tobacco extensin 3' UTR; NbACT3 refers to the *N. benthamiana* actin 3' UTR; NbHSP refers to the *N. benthamiana* 18.8 kDa class II heat shock protein 3' UTR; pinII refers to the potato proteinase inhibitor II 3' UTR; RbcS refers to the pea rubisco small subunit 3' UTR; SIR refers to the short intergenic region of bean yellow dwarf virus, where SIR 5'/3' includes additional upstream and downstream sequences and SIR 3' include only additional downstream sequences; BDB refers to the bean dwarf mosaic virus DNA B nuclear shuttle protein 3' UTR; Rep refers to the bean dwarf mosaic virus rep gene 3' UTR; RepA refers to the bean dwarf mosaic virus repA gene 3' UTR; AtHSP refers to the *Arabidopsis thaliana* heat shock protein 3' UTR; 35S refers to the cauliflower mosaic virus 35S 3' UTR; and NOS refers to the *agrobacterium* nopaline synthase 3' UTR.

FIG. 14A shows the mean relative GFP expression±standard error of 3-4 independently infiltrated leaves. "(R)" indicates replicating geminiviral vector. FIG. 14B depicts SDS-PAGE gels showing GFP expression with the indicated constructs. RbcL refers to the large subunit of Rubisco.

FIG. 17A depicts photographs of leaves agroinfiltrated with nonreplicating GFP vectors containing either the tobacco Rb7 or tobacco TM6 MAR sequences. The photographs were taken after 5 DPI under UV illumination (365 nm). In FIG. 17A, "No 3' Elements" refers to vectors that contain no terminator or MAR; "Rb7 Only" refers to vectors that contain only the Rb7 MAR with no terminator; "5' Rb7" refers vectors that contain the Rb7 MAR inserted 5' of the promoter; and "3' Rb7," "Rb7," or "TM6," identifies the MAR that was inserted 3' of the gene terminator in the vector. FIG. 17B depicts a schematic of deletion mutants of the Rb7 MAR. GFP expression was measured by SDS-PAGE using ImageJ to quantify band intensity. Relative expression is given compared to terminator EU lacking the Rb7 MAR.

FIG. 18A depicts the generalized schematic of the replicating vector derived from bean yellow dwarf virus. The abbreviations used in FIG. 18A refers to the left and right T-DNA borders from *Agrobacterium* as RB and LB; the nopaline synthase 3' UTR from *Agrobacterium* as NOS3'; the p19 suppressor of RNA silencing from tomato bushy stunt virus as P19; the 35S promoter from cauliflower mosaic virus for P35S; the long intergenic region from bean yellow dwarf virus as LIR; the 5' UTR from *N. benthamiana* psaK gene as NbPsaK 5'; the target gene as indicated in each experiment as VLP; various single or double terminators as indicated in each experiment as T1/T2; the matrix attachment region from the tobacco Rb7 gene as Rb7 MAR; the short intergenic region from bean yellow dwarf virus for SIR; and the rep/repA genes from bean yellow dwarf virus Rep/RepA. FIGS. 18B and 18D respectively depicts ELISA results measuring GII.4 norovirus (B) or GI norovirus (D) capsid production in the *N. benthamiana* leaves were agroinfiltrated with the replicating vector derived from bean yellow dwarf virus. Plant-produced GI or GII norovirus capsid served as standard. Data shown are means±standard deviation from three independently infiltrated samples. Two asterisks () indicate $p<0.05$, and three asterisks (*) indicate $p<0.01$ as compared to the unmodified vector by student's t-test. FIG. 18C shows reducing SDS gel western of double terminator constructs with or without the addition of 0.1% Triton X-100 detergent (Triton). Probe is polyclonal rabbit anti-GII. The abbreviations as used in FIGS. 18B-18C refer to intron-containing tobacco extensin terminator as IEU; IEU fused to the 35S terminator from cauliflower mosaic virus as IEU-35S; intronless tobacco extensin terminator fused to the putative ACT3-like terminator from *N. benthamiana* as EU-NbACT3; and 35S terminator fused to NbACT3 terminator as 35S-NbACT3.

FIG. 19 depict the schematic for a 14115 bp plasmid (pBYR2eAK2Mc-GFP, sequence set forth in SEQ ID NO. 115) comprising in the 3' region of the expression cassette a double terminator of EU fused upstream of NbACT3 and the Rb7 MAR downstream of the double terminator.

FIG. 20 depicts the schematic for a 17111 bp plasmid (pBY11HA-GFP, sequence set forth in SEQ ID NO. 116), which comprises two expression cassettes. The upstream expression cassette comprises in the 3' region a double terminator of EU fused upstream of NbHSP (shown as HSP20 3' in the figure) and the Rb7 MAR downstream of the double terminator. The downstream expression cassette comprises in the 3' region a double terminator of EU fused upstream of NbACT3 and the Rb7 MAR downstream of the double terminator.

FIG. 21 depicts the schematic for a 19330 bp plasmid (pBY!11-h6D8M2, sequence set forth in SEQ ID NO. 117), which comprises expression cassettes for a modified mAb, where the upstream cassette codes the heavy chain fused to influenza antigen M2e and the second cassette codes the corresponding light chain. The 3' region of the upstream expression cassette comprises a double terminator of EU fused upstream of NbACT3 and the RB7 MAR downstream of the double terminator. The 3' region of the downstream expression cassette comprises a double terminator of EU fused upstream of NbHSP (shown as HSP20 3' in the figure) and the Rb7 MAR downstream of the double terminator.

FIG. 22A shows that relative percentage of the total soluble protein produced from leaves infiltrated with the plasmid with FIG. 21 that is the modified antibody encoded by the two expression cassettes. Although typical extraction protocol did not appear to yield much of the antibody in the total soluble proteins, the combination of urea and Triton X-100 resulted in over 40% of the total soluble protein being the modified antibody encoded in the plasmid. FIG. 22B depicts an exemplary gel that corresponds with the results of FIG. 22A. FIG. 22C compares fluorescence generated from the plasmid of FIG. 19 with plasmid that comprises a single terminator (pBYR2eK2Mc-GFP, labeled as 2eK2Mc in the figure), which shows the double terminator construct produces (pBYR2eAK2Mc-GFP, labeled in the figure as 2eAK2Mc) brighter fluorescence than the single terminator construct.

DETAILED DESCRIPTION

Figure 3A:
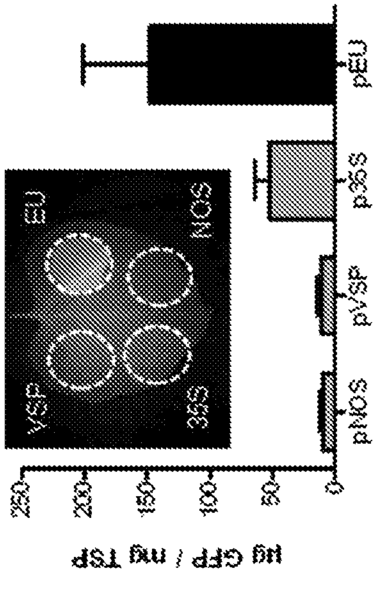
FIGS. 3A-3C, in accordance with certain embodiments, show that the Ext terminator increases transient transgene expression in *Nicotiana benthamiana* leaves.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

As used herein, the term "expression cassette" refers to a distinct component of vector DNA, which contains gene sequences and regulatory sequences to be expressed by the transfected cell. An expression cassette comprises three components: a promoter sequence (part of the 5' untranslated region, 5' UTR), an open reading frame, and a 3' untranslated region (3' UTR). In some aspects, the regulatory sequences are found in the 5' UTR and the 3' UTR.

As used herein, the term "terminator" refers to a DNA sequence that causes the dissociation of RNA polymerase from DNA and hence terminates transcription of DNA into mRNA. Accordingly, while the term encompasses terminator sequences of known genes, the term also encompasses other sequences that perform the same function, for example, sequences around the short intergenic region of bean yellow dwarf virus.

The disclosure relates to 3' untranslated regions (UTRs), which in an expression cassette encoding a protein increases the expression level of the protein, and vectors for recombinant protein production in plants that utilize in at least one of its expression cassettes the 3' UTR disclosed herein. In some aspects, the plant expression vector is a replicating vector, for example a geminivirus vector. In other aspects, the plant expression vector is a non-replicating vector.

The plant expression vector described herein comprise at least one expression cassette, wherein the 3' UTR of the expression cassette comprises a single terminator or a double terminator. As used herein, a single terminator refers to a terminator element that contains one set of terminator sequences. As used herein, a double terminator refers to a terminator element that contains one set of terminator sequences fused with another set of terminator sequences. In some aspects, the expression cassette further comprises a chromatin scaffold/matrix attachment region (MAR). The MAR is downstream of the single terminator of the double terminator.

The vectors described herein results an increase in protein production (for example, as determined by the reporter gene GFP) compared to vectors using the most widely used terminators in the past 30 years, which include nopaline synthase (NOS) and octopine synthase (OCS) terminators from *Agrobacterium tumefaciens*, the 35S terminator from cauliflower mosaic virus (MacFarlane et al.,1992; Ellis et al., 1987; Pietrzak et al., 1986), and the terminator of soybean vegetative storage protein (VSP). In some embodiments, the increase in recombinant protein production is more than 5-fold, 7-fold, 10-fold, 15-fold, 20-fold, 25-fold, 30-fold, 40-fold, 50-fold, 60-fold, 100-fold, or 150-fold. In some aspects, the increased recombinant protein production is due increased stability of the transcripts. The benefits of the vectors described in herein is seen in a variety of plants (including, for example, tobacco and lettuce) and with a variety of recombinant proteins.

The 3' UTR regions that provide enhanced production of the recombinant protein are the extensin 3' UTR (also referenced herein as the extensin terminator), *Nicotiana benthamiana* actin 3' UTR (NbACT3), potato proteinase inhibitor II 3' UTR (Pin2), bean dwarf mosaic virus DNA B nuclear shuttle protein 3' UTR (BDB), *N. benthamiana* 18.8 kDa class II heat shock protein 3' UTR (NbHSP), bean dwarf mosaic virus rep gene 3' UTR (Rep), pea rubisco small subunit 3' UTR (RbcS), short intergenic region of bean yellow dwarf virus (SIR), *A. thaliana* heat shock protein 3' UTR (AtHSP), cauliflower mosaic virus 35S 3' UTR (35S), bean dwarf mosaic virus repA gene 3' UTR (RepA), and *agrobacterium* nopaline synthase 3' UTR (NOS). The sequences of these 3'UTR are well-known in the art. In some implementations, the oligonucleotide sequences of these 3' UTRs for the synthesis of the vectors described herein are produced in the methods described in the Examples.

In some aspects, the nucleic acid sequence of the extensin terminator selected from the terminator sequences of the extensin gene in *Nicotiana tabacum, Nicotiana tomentosiformis, Nicotiana plumbaginifolia, Nicotinana attenuata, Nicotinana sylvestris, Nicotiana benthamiana, Solanum tuberosum, Solanum lycopersicum, Solanum pennellii, Capsicum annuum*, and *Arabidopsis thaliana*, the sequences of which are determinable from GenBank or the Sol Genomics Network. The nucleic acid sequence of the extension terminator comprises a polypurine sequence, an atypical near upstream element (NUE), an alternative polyA site, a far upstream element (FUE)-like region, a major NUE, and a major polyA region, and in certain embodiments, the nucleic acid sequence has at least 72%, at least 73%, at least 74%, at least 75%, at least 76%, at least 77%, at least 78%, at least 79%, 72%, 73%, 74%, 75%, 76%, 77%, 78%, or 79% identity to the sequence of the tobacco (*N. tabacum*) extension terminator. In some embodiments, the nucleic acid sequence of the extension terminator is that of the tobacco extensin gene. In certain embodiments, the portion of the extensin 3' UTR in the disclosed vector lacks the intron. In a particular embodiment, the 3' UTR region of the vector comprises an intronless tobacco extensin terminator (EU). Thus in some aspects, the nucleic acid sequence of EU spans nt 2764-3126 of the complete N. tabcacum gene for extensin (GenBank D13951.1). In certain other embodiments, the disclosed vector comprises intron-containing extensin terminator. Thus in some aspects, the 3' UTR region of the vector comprises an intron-containing tobacco extensin terminator (IEU). In such embodiments, the nucleic acid sequence of IEU spans nt 2396-3126 of the complete N. tabcacum gene for extensin (GenBank D13951.1).

In some aspects, the nucleic acid sequence of NbACT3 comprises nt 1460-1853 of actin gene (Gene ID Niben101Scf00096g04015.1). In some aspects, the nucleic acid sequence of NbACT3 comprises nt 33-1023 of the sequence set forth in SEQ ID NO. 8. In some aspects, the *N. benthamiana* actin 3' UTR is not the entirety of the 3' UTR, but only the downstream 617-nt region of NbACT3 (NbACT617). In such embodiments, the nucleic acid sequence of NbACT617 comprises nt 606-1023 of the sequence set forth in SEQ ID NO. 8. In other aspects, the *N. benthamiana* actin 3' UTR is not the entirety of the 3' UTR, but only the downstream 567-nt region of NbACT3 (NbACT567).

In some embodiments, the nucleic acid sequence of Pin2 spans nt 1507-1914 of the potato gene for proteinase inhibitor II (GenBank: X04118.1). In some aspects, the sequence of pinII is obtained from pHB114 (Richter et al., 2000) by SacI-EcoRI digestion.

In some embodiments, the nucleic acid sequence of BDB comprises the 3' end of the nuclear shuttle protein, the intergenic region, the 3' end of the movement protein, and additional 200 nt downstream of the movement protein sequence (BDB501), which spans nt 1213-1713 of bean dwarf mosaic virus segment DNA-B (GenBank: M88180.1). In some embodiments, the nucleic acid sequence of BDB comprises only the 282 nucleotides that include the 3' end of the nuclear shuttle protein, the intergenic region, and the 3' end of the movement protein (BDB282).

In some embodiments, the nucleic acid sequence of NbHSP comprises the complement to nt 988867-989307 of the sequence of Gene ID Niben101Scf04040. In some aspects, the nucleic acid sequence of NbHSP spans nt 33-424, nt 33-447, nt 33-421, nt 33-453, nt 45-424, nt 45-447, nt 45-421, or nt 45-453 of the sequence set forth in SEQ ID NO. 7. In one embodiment, the nucleic acid sequence spanning nt 45-421 of the sequence set forth in SEQ ID NO. 7 is NbHSP. In embodiments, the nucleic acid sequence of NbHSPb comprises the complement to nt 988942-989307 of the sequence of Gene ID Niben101Scf04040. In some aspects, the nucleic acid sequence spanning nt 45-372 of the sequence set forth in SEQ ID NO. 7 is NbHSPb.

In some embodiments, the nucleic acid sequence of Rep comprises a sequence with at least 95%, preferably 99%, sequence identity to the complement of nt 859-1522 of bean yellow dwarf virus putative genes V1, V2, C1, C1:C2 (GenBank: Y11023.2). In some aspects, the sequence of Rep is set forth in SEQ ID NO. 14.

In some embodiments, the nucleic acid sequence of rbcS comprises a sequence that is complementary to the sequence spanning nt 6-648 of transient gene expression vector pUCPMA-M24 (GenBank: KT388099.1). In some aspects, the sequence of rbcS is obtained from pRTL2-GUS (Carrington et al., 1999) by SacI-EcoRI digestion.

In some embodiments, the 3' UTR comprises SIR, SIR with its additional downstream viral sequence (SIR 3'), or SIR with additional sequences both upstream and downstream (SIR 5'/3'). In some aspects, the nucleic acid sequence of SIR573' comprises a sequence with at least 95%, preferably 99%, sequence identity to nt 730-1966 of bean yellow dwarf virus putative genes V1, V2, C1, C1:C2 (GenBank: Y11023.2). In some embodiments, the sequence of SIR 5'/3' is set forth in SEQ ID NO. 11. In some aspects, the nucleic acid sequence of SIR 3' comprises a sequence with at least 95%, preferably 99%, sequence identity to nt 1155-1966 of bean yellow dwarf virus putative genes V1, V2, C1, C1:C2 (GenBank: Y11023.2). In some embodiments, the sequence of SIR 3' is set forth in nt 7-818 of SEQ ID NO. 10. In aspects, the nucleic acid sequence of SIR comprises nt 1122-1326 of bean yellow dwarf virus putative genes V1, V2, C1, C1:C2 (GenBank: Y11023.2). In some embodiments, the nucleic acid sequence of SIR is set forth in nt 4-208 of SEQ ID NO. 9.

In some embodiments, the nucleic acid sequence of AtHSP comprises nt 1-250 of the partial sequence of the *A. thaliana* heat shock protein 18.3 gene (GenBank KP008108.1). In some aspects, the nucleic acid sequence of AtHSP spans nt 7-257 of SEQ ID NO. 13.

In some embodiments, the nucleic acid sequence of 35S comprises a sequence spanning nt 3511-3722 of plant transformation vector pSITEII-8C1 (GenBank: GU734659.1). In some aspects, the sequence of 35S is set forth in nt 7-218 of SEQ ID NO. 2. In some aspects, the sequence of 35S is the sequence of the amplication of pRTL2-GUS (Carrington et al 1991) using the primers 35STm-1 (SEQ ID NO. 26) and 35STm-2 (SEQ ID NO. 27).

In some embodiments, the nucleic acid sequence of RepA comprises the complementary sequence to nt 859-1311 of bean yellow dwarf virus putative genes V1, V2, C1, C1:C2 (GenBank: Y11023.2). In some aspects, the nucleic acid sequence of RepA is set forth in nt 6-458 of SEQ ID NO. 15.

In some embodiments, the nucleic acid sequence of NOS comprises nt 22206-22271 of the T-DNA region of cloning vector pSLJ8313 (GenBank: Y18556.1). In some aspects, the sequence of NOS is that of the fragment obtained from pHB103 (Richter et al., 2000) by SacI-EcoRI digestion. In some aspects, the nucleic acid sequence of NOS is set forth in nt 6-261 of SEQ ID NO. 1.

In some embodiments, the 3' UTR region comprises at least one member from the group consisting of: EU, IEU, NbACT3, NbACT617, NbACT567, Pin2, BDB501, BDB282, NbHSP, NbHSPb, Rep, RbcS, SIR, SIR 5'/3', SIR 3', AtHSP, 35S, RepA, and NOS. In certain embodiments, the 3' UTR region of the vector consists of a terminator selected from the group consisting of: EU, NbACT3, Pin2, BDB501, NbHSP, Rep, RbcS, NbACT617, SIR 5'/3', NbACT567, NbHSPb, and AtHSP. In some implementations, the 3' UTR region of the vector consists of a terminator selected from the group consisting of: EU, NbACT3, Pin2, BDB501, NbHSP, Rep, and RbcS.

In some aspects, the 3' UTR comprises two terminators, which produces a double terminator. The double terminator may be a repeat of same terminator or a combination of different terminators (for example, a fusion of two different terminators). In some embodiments, the double terminator consists of EU with NbACT, P19, NbHSP, SIR, NOS, 35S, tobacco mosaic virus 3' UTR (TMV), BDB501, tobacco necrosis virus-D 3' UTR (TNVD), pea enation mosaic virus 3' UTR (PEMV), or barley yellow dwarf virus 3' UTR (BYDV). In some aspects, the aforementioned pair of terminators are arranged where EU is arranged upstream of the other terminator, which is denoted as EU+NbACT, EU+P19, EU+NbHSP, EU+SIR, EU+NOS, EU+35S, EU+TMV, EU+BDB501, EU+TNVD, EU+PEMV, or EU+BYDV. In some embodiments, the double terminator consists of 35S with NbACT3, NOS, EU, NbHSP, Pin2, or BDB501. In some aspects, the aforementioned pair of terminators are arranged where 35S is arranged upstream of the other terminator, which is denoted as 35S+NbACT3, 35S+NOS, 35S+EU, 35S+NbHSP, 35S+Pin2, or 35S+BDB501. In some embodiments, the double terminator consists of IEU with SIR, 35S, or long intergenic region from bean yellow dwarf virus (LIR). In some aspects, the aforementioned pair of terminators are arranged where IEU is arranged upstream of the other terminator, which are denoted as IEU+SIR, IEU+35S, or IEU+LIR. In some embodiments, the double terminator consists of NbHSP with NbACT3, NOS, or Pin2. In some aspects, the aforementioned pair of terminators are arranged where NbHSP is upstream of the other terminator, which is denoted as NbHSP+NbACt3, NbHSP+NOS, or NbHSP+Pin2. In some embodiments, the double terminator consists of NOS with 35S, where NOS is arranged upstream of 35S (NOS+35S).

As used herein, the term "P19" refers to the P19 suppressor of RNAi silencing. An exemplary vector backbone that comprises P19 is pEAQ-HT (see Sainsbury et al., 2009).

In accordance with certain embodiments, the nucleic acid sequence of TMV spans nt 489-693 of the tobacco mosaic virus isolate TMV-JGL coat protein gene (GenBank: KJ624633.1). In some aspects, the nucleic acid sequence of TMV is set forth in nt 7-211 of SEQ ID NO. 21.

In accordance with certain embodiments, the nucleic acid sequence of TNVD has at least 85% identity, preferably 87% identity, to the sequence spanning nt 3457-3673 of the complete genome of tobacco necrosis virus D genome RNA (GenBank: D00942.1). In other embodiments, the nucleic acid sequence of TNVD has at least 90%, preferably 93%, sequence identity with nt 3460-3673 of tobacco necrosis virus-D genome (GenBank: U62546.1). In some embodiments, the nucleic acid sequence of TNVD comprises the sequence set forth in nt 29-222 of SEQ ID NO. 19.

In accordance with certain embodiments, the nucleic acid sequence of PEMV has at least 95%, preferably 98%, sequence identity with nt 3550-4250 of the pea enation mosaic virus-2 strain UK RNA-dependent RNA-polymerase, hypothetical protein, phloem RNA movement protein, and cell-to-cell RNA movement protein genes (GenBank: AY714213.1). In some aspects, the nucleic acid sequence of PEMV is set forth in nt 1-703 of SEQ ID NO. 20.

In accordance with certain embodiments, the nucleic acid sequence of BYDV has at least 95%, preferably 99%, sequence identity with nt 4807-5677 of barley yellow dwarf virus—PAV genomic RNA (GenBank: X07653.1). In some aspects, the nucleic acid sequence of BYDV is set forth in nt 5-875 of SEQ ID NO. 18.

In another embodiment, the vector further comprises at a chromatin scaffold/matrix attachment region (MAR) downstream of the region comprising the at least one terminator. In a preferred embodiment, the MAR is the Rb7 MAR (GenBank: U67619.1) or the TM6 enhancer region (GenBank: KC5555564.1). As used herein, the term "Rb7" refers to a sequence comprising the sequence of GenBank ID U67619.1 or set forth in nt 7-1174 of SEQ ID NO. 16. As used herein, the term "TM6" refers to a sequence comprising the sequence of GenBank ID KC5555564.1 or set forth in nt 10-1202 of SEQ ID NO. 17. Accordingly, in some implementations, the vector comprises the terminator EU in combination with Rb7, the terminator IEU with Rb7 or TM6, the terminator AtHSp with Rb7, the terminator 35S with Rb7 or TM6, the terminator BDB501 with Rb7, the terminator NbHSP with Rb7, the terminator NOS with Rb7, or the terminator NbACT3 with Rb7 or TM6.

In certain embodiments, the vector comprises a double terminator and a MAR, wherein the MAR is downstream of the double terminators. In some implementations, the MAR is Rb7, and it is downstream of the double terminators 35S+NbACT3, EU+35S, EU+NbACT3, NbHSP+NbACT3, 35S+EU, AtHSP+NOS, 35S+NOS, EU+BDB501, AtHSP+NbHSP, NbHSP+NOS, AtHSP+EU, NbHSP+Pin2, or IEU+35S. In other implementations, the MAR is TM6, it is downstream of the double terminators EU+35S, 35S+NOS, NbHSP+NOS, or NbHSP+Pin2.

The disclosure is also related to oligonucleotides for the production of disclosed vectors. SEQ ID NOs.1-21 provides the nucleic acid sequences for incorporating the aforementioned 3' UTRs into vectors. The nucleic acid sequence of the template for incorporating NOS is set forth in SEQ ID NO. 1. The nucleic acid sequence of the template for incorporating 35S is set forth in SEQ ID NO. 2. The nucleic acid sequence of the template for incorporating pinII is set forth in SEQ ID NO. 3. The nucleic acid sequence of the template for rbcS is set forth in SEQ ID NO. 4. The nucleic acid sequence of the template for incorporating IEU is set forth in SEQ ID NO. 5. The nucleic acid sequence of the template for incorporating EU is set forth in SEQ ID NO. 6. The nucleic acid sequence of the template for incorporating NbHSP is set forth in SEQ ID NO. 7. The nucleic acid sequence of the template for incorporating NbACT3 is set forth in SEQ ID NO. 8. The nucleic acid sequence of the template for incorporating SIR is set forth in SEQ ID NO. 9. The nucleic acid sequence of the template for incorporating SIR 3' is set forth in SEQ ID NO. 10. The nucleic acid sequence of the template for incorporating SIR 5'/3' is set forth in SEQ ID NO. 11. The nucleic acid sequence of the template for incorporating BDB501 is set form in SEQ ID NO. 12. The nucleic acid sequence of the template for incorporating AtHSP is set forth in SEQ ID NO. 13. The nucleic acid sequence of the template for incorporating Rep is set forth in SEQ ID NO. 14. The nucleic acid sequence of the template for incorporating RepA is set forth in SEQ ID NO. 15. The nucleic acid sequence of the template for incorporating Rb7 MAR is set forth in SEQ ID NO. 16. The nucleic acid sequence of the template for incorporating TM6 MAR is set forth in SEQ ID NO. 17. The nucleic acid sequence of the template for incorporating barley yellow dwarf virus's (BYDV's) 3' UTR is set forth in SEQ ID NO. 18. The nucleic acid sequence of the template for incorporating TNVD 3' UTR is set forth in SEQ ID NO. 19. The nucleic acid sequence of the template for incorporating PEMV 3' UTR is set forth in SEQ ID NO. 20. The nucleic acid sequence of the template for incorporating tobacco mosaic virus 3' UTR is set forth in SEQ ID NO. 21.

The disclosure is further related to methods of producing recombinant protein in a plant or plant part. In some aspects, the method produced at least 5-fold, 7-fold, 10-fold, 15-fold, 20-fold, 25-fold, 30-fold, or 40-fold yield of the recombinant protein than methods of the prior art. The method comprises introducing a vector described above into the plant or plant part. In some implementations, the plant or plant part is transformed by the vector of the disclosure using an *Agrobacterium*, for example, *Agrobacterium tumefaciens*, or more specifically, *A. tumefaciens* GV3101. In one aspect, the plant or plant part is transformed by the vector of the disclosure using agroinfiltration. In one implementation, the plant is tobacco or tomato while the plant part is from a tobacco plant or tomato plant.

Illustrative, Non-Limiting Examples in Accordance with Certain Embodiments

The disclosure is further illustrated by the following examples that should not be construed as limiting. The contents of all references, patents, and published patent applications cited throughout this application, as well as the Figures, are incorporated herein by reference in their entirety for all purposes.

Figure 9A:
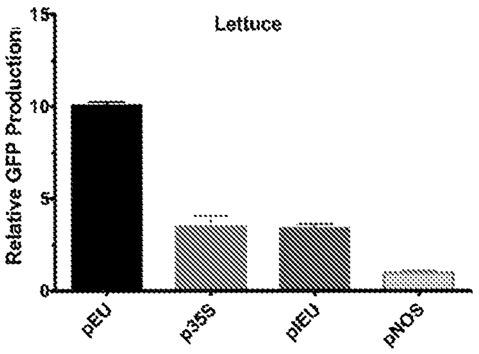
FIGS. 9A and 9B, in accordance with certain embodiments, show that the Ext terminator has strong activity in plants other than *N. benthamiana*. GFP constructs containing the Ext terminator with or without intron were agroinfiltrated into the leaves of lettuce (FIG. 9A) or tobacco (FIG. 9B). At 4 DPI, leaf tissue was harvested, and protein extracts were analyzed by SDS-PAGE followed by observation under UV illumination (365 nm) and by Coomassie staining. GFP band intensity was quantified using ImageJ software, using native plant proteins as a loading control. Data shown are means±standard error of three independently infiltrated leaves. All leaves were infiltrated with construct pEU as an internal control for leaf and plant variability.
Figure 9B:
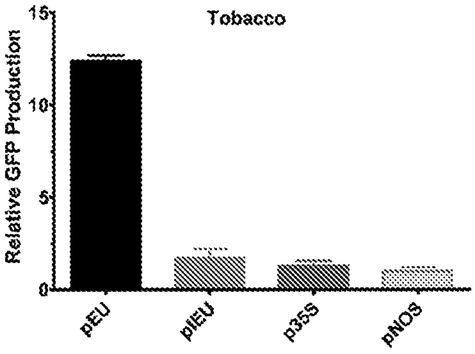

1. Tobacco Extensin (Ext) Terminator a. Influence of the Ext Intron on Gene Expression The Ext terminator consists of 746 nt and contains an intron between nt 24 and 249. To characterize the activity of the Ext terminator with and without the intron, different forms were cloned into *Agrobacterium* T-DNA vectors. Intron-containing Ext terminator constructs were generated (FIG. 1B): the Ext terminator segments from nt 1-731 or nt 1-464, including the intron sequence (nt 24-249), were PCR amplified from tobacco genomic DNA and fused to the GFP gene under the control of the strong 35S promoter from cauliflower mosaic virus (pIEU or pIEU2, respectively). Similar constructs were created with the intron deleted, using nt 252-731 or 252-464 (pEU or pEU2, respectively). These constructs were then compared by *Agrobacterium*-mediated transient expression in *N. benthamiana* leaves. The intron-less constructs pEU and pEU2 showed a significantly higher level of GFP expression compared to the intron-containing construct pIEU and pIEU2 (~3-fold, FIG. 2A). To test whether the effects of removing the Ext intron were gene-specific, the GFP gene was replaced with the NVCP gene. NVCP is a candidate vaccine antigen for the protection against Norwalk virus infections, which cause epidemic acute gastroenteritis in humans. The NVCP expression of the intron-containing construct, pIEU or pIEU2, was also lower than that of the intron-less constructs, pEU or pEU2 (~29-75% activity remained, FIG. 2B), though the magnitude of the inhibitory effect of the intron was not as great with pIEU. From the intron-containing constructs, either with GFP or NVCP gene, efficient splicing was confirmed by RT-PCR as no detectable unspliced product was found in ethidium bromide-stained agarose gel electrophoresis. The intron also greatly reduced expression of DsRed. To determine whether the inhibitory effect of the intron was species-specific, pEU and pIEU were agroinfiltrated into tobacco and lettuce leaves. In agreement with our results obtained with *N. benthamiana*, the presence of the intron substantially reduced gene expression in both species, with 34% activity remaining in lettuce and 14% remaining in tobacco (FIG. 9). These data indicate that the Ext intron may have a deleterious effect on gene expression, in agreement with previously reported findings for introns inserted into 3' UTRs (Kertesz 2006). However, we cannot exclude the possibility that the effect was due to the incorporation of the 23 nt (1-23 nt upstream of the intron) in the intron-containing constructs.

It has been reported that the effect of intron insertion changes in a context-dependent manner (Kertesz 2006). The effect of the Ext intron was also tested in context of the NOS terminator: PCR-amplified Ext intron (1-251 nt) was fused to the 5' end of the NOS terminator preceded by the GFP or NVCP gene. Unexpectedly, the addition of the Ext intron to NOS terminator caused slight but statistically insignificant increases in GFP or NVCP expression by 51% and 34%, respectively (FIGS. 2A and 2B, pNOS vs. pINOS). Taken together, these data indicate that the Ext intron has context-dependent effects on transient transgene expression.

b. Ext Terminator Increases Transient Transgene Expression

Figure 3B:
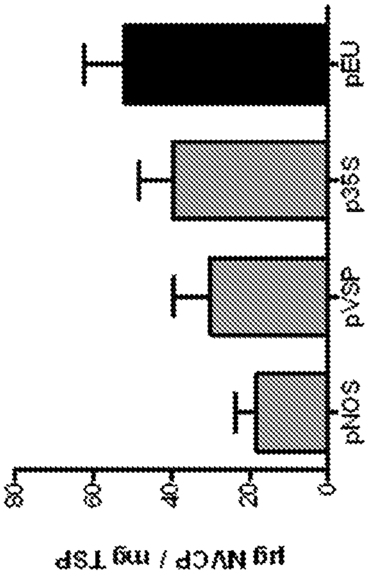

We evaluated the effects of the tobacco Ext terminator on transient transgene expression in comparison to other widely used terminators, including NOS, CaMV 35S, and soybean vegetative storage protein (VSP). For this comparison, we placed the intron-less Ext terminator (nt 252-731) and the other terminators downstream of the GFP gene, driven by the CaMV 35S promoter with the tobacco etch virus (TEV) 5' UTR (FIG. 1A). The resulting constructs were introduced into *N. benthamiana* leaves by agroinfiltration, and at 2 DPI the level of GFP expression was analyzed. Expression peaked between 2-3 DPI and declined thereafter, likely due to gene silencing (data not shown). The Ext construct (pEU) yielded the highest GFP expression level, at 13.5-fold, 11.9-fold, and 2.8-fold higher than those with the NOS, VSP, and 35S constructs (pNOS, pVSP, and p35S), respectively (FIG. 3A). To test whether the enhancing effect of the intron-less Ext terminator is gene specific, we replaced the GFP gene with the NVCP gene and compared the level of NVCP expression. Results using NVCP were similar to those with GFP, suggesting that the enhanced transgene expression by the Ext terminator is not gene specific (FIG. 3B). To determine whether the Ext terminator also functions without TEV 5' UTR, we directly fused the 35S promoter to a GUS reporter gene, followed by the various terminators (FIG. 1A). We found that the Ext terminator increased expression of GUS without TEV 5' UTR (FIG. 3C), suggesting that the ability of the Ext terminator to increase expression is independent of the specific 5' UTR and transgene. To assess whether these results are generalizable to other plant species, we tested the extensin, NOS, and 35S terminators in tobacco and lettuce. In agreement with our results in *N. benthamiana*, the intronless extensin terminator strongly enhanced transgene expression compared to either NOS or 35S, but the magnitude of the enhancing effect was slightly reduced in lettuce (FIG. 9). These results show that the intronless extensin terminator functions in a variety of different species and gene contexts as a potent enhancer of transgene expression compared to other commonly used terminators.

c. Ext Terminator Increases mRNA Accumulation

Figure 4A:
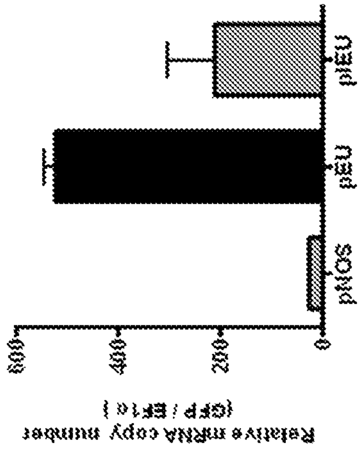
FIGS. 4A and 4B, in accordance with certain embodiments, show that the Ext terminator increases mRNA accumulation.
Figure 4B:
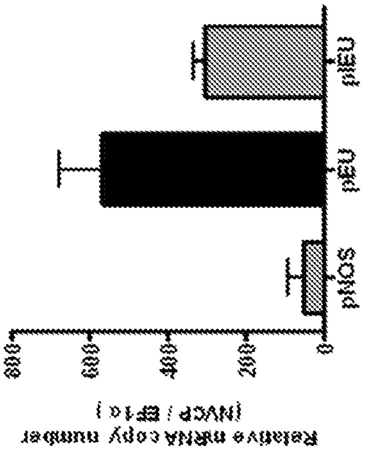

The 3' UTR influences the fate of mRNA through a complex interplay of multiple nuclear and cytoplasmic processes, including polyadenylation, transcript termination, transcript reinitiation, nuclear export, and translatability, as well as by avoiding deleterious interactions with RNA silencing and mRNA decay pathways. The upregulated transgene expression mediated by the intronless Ext terminator could be caused by an increase in either mRNA level or translational efficiency. To investigate whether the Ext terminator affects mRNA accumulation, the levels of accumulated transgene mRNAs were compared. Construct pEU produced approximately 20-fold increase in GFP mRNA accumulation compared to construct pNOS (FIG. 4A). Consistently, NVCP mRNA accumulation using construct pEU was approximately 10-fold higher compared to that of construct pNOS (FIG. 4B). These results indicate that the enhanced transgene expression mediated by the Ext terminator is due at least in part to increased mRNA accumulation.

We also compared the levels of mRNA accumulation between intronless and intron-containing constructs (pEU vs. pIEU). The use of the Ext intron caused a 40-50% decrease in mRNA accumulation (FIGS. 4A and 4B), which was consistent with the protein expression data (FIGS. 2A and 2B).

d. Ext Terminator Mediates Efficient Transcription Termination.

The stability of mRNA is greatly affected by the efficiency of transcription termination and mRNA 3' end processing. Improperly terminated and unpolyadenylated mRNA is targeted by RNA-dependent RNA polymerase 6 (RDR6)-mediated RNA silencing (Luo and Chen 2007) and long 3' UTRs are subject to the nonsense-mediated decay pathway (Kertesz 2006). To determine if the Ext terminator increases the efficiency of transcription termination, we tested for the presence of read-through transcripts from Ext and NOS terminator constructs using RT-PCR with random primed cDNA (FIG. 5A). A forward primer specific to either the GFP (FIG. 5A) or NVCP gene (FIG. 5C) (gfp-3f or sNV-3f) was paired with one of four antisense primers (RT-0, RT-1, RT-2, and RT-3) specific to different downstream regions of the terminator. From the NOS terminator samples, specific RT-PCR bands of the same size as the positive controls were detected with the first three reverse primers, RT-0, RT-1, and RT-2, indicating that the NOS terminator generated readily detectable read-through transcripts when driven by the strong CaMV 35S promoter. In contrast, no detectable levels of specific bands were amplified in the Ext terminator samples with any primer set. These data demonstrate that read-through transcription is greatly reduced by the Ext terminator compared to the NOS terminator.

e. Polyadenylation Sites of the Extensin Terminator

Positions of five putative NUEs and polypurine sequence (PPS) of the Ext terminator are indicated in FIG. 6. To characterize the location and features of the poly(A) sites of the Ext terminator, transgene transcripts were analyzed by circularized RT-PCR, a method which can detect the native position and length of poly(A) tails (Slomovic and Schuster 2013). GFP transcripts were decapped, circularized, RT-PCR amplified using primers specific for circularized templates, cloned, and sequenced. The data show that the Ext terminator contains a region of two nearby poly(A) sites (12 out of 14 sequences, 86%) at a YA dinucleotide either 13 or 25 nt downstream from the fourth putative NUE, a canonical AAUAAA motif (FIG. 6). Of the 12 polyadenylated transcripts detected in this region, 9 occurred at nt 527, while the other three occurred at nt 515. As multiple cleavage sites are typically found in the same area downstream from a single NUE, these data are consistent with the hypothesis that the fourth NUE directs most of the polyadenylation in the Ext terminator (Rothnie et al 2001). In support of the functional relevance of this region, homologous extensin 3' UTRs from plant species with available sequences (obtained from GenBank of the Sol Genomics Network) were aligned using the Clustal Omega Program. The extensin terminators of *N. tabacum, N. tomentosiformis, N. plumbaginifolia, N. attenuate, N. sylvestris, N. benthamiana, S. tuberosum, S. lycopersicum, S. pennellii, C. annuum*, and *A. thaliana* were compared, and the alignment revealed that the fourth NUE is highly conserved.

Alternative polyadenylation sites have been found in more than 50% of all eukaryotic genes (Tian and Manley 2013). An infrequently utilized alternative poly(A) site (14%, 2 out of 14) was found at position 424, between the third and fourth putative NUEs. This site was also highly conserved among related extensin terminators. As NUEs have been shown typically to reside 10-40 nucleotides upstream from the polyadenylation site (Loke et al 2005), and the closest typical NUE is 70 nt upstream from the alternative polyadenylation site, our results suggest an atypical NUE may direct polyadenylation at this site, consistent with its infrequent utilization. We found no evidence that the other putative NUEs were functionally active, though we cannot exclude the possibility that they are infrequently utilized.

f. Deletion Analysis of the Ext Terminator

Using a series of deletion constructs depicted in FIG. 1B, we investigated whether specific regions of the Ext terminator controlled its function by measuring transient expression of GFP (FIG. 7). Compared to the full-length construct pEU (nt 252-731), construct pEU2 (nt 252-464) removed the major polyadenylation site identified by cRT-PCR. Deletion construct pEU2 exhibited a substantially lower level of GFP gene expression compared to pEU (11-14% activity remained). These data indicate that the 89-bp sequence (nt 465-553) is essential to yield maximum gene expression. This result is consistent with the polyadenylation data that the fourth putative NUE directs most of the polyadenylation of the Ext terminator. The residual activity of this deletion construct may result from the infrequently utilized alternative polyadenylation site, which remained intact in this construct. To further confirm the role of the fourth NUE in the function of the Ext terminator, we created construct pNUE4a, which substitutes the A-rich region "AATAAACTAA" hypothesized to serve as the NUE, with "TCGTAGCTCT." This substitution greatly reduced GFP expression to a similar level compared to pEU2 (FIG. 7).

The deletion construct pEU1 (nt 252-553) retains all five NUEs, but removes the area immediately downstream from the putative major cleavage site, including a U-rich region typical of CEs. Compared to the full-length construct pEU, expression of pEU1 was substantially reduced (~36% activity remained), suggesting that this region is essential for optimum efficiency of the extensin terminator.

Figure 8A:
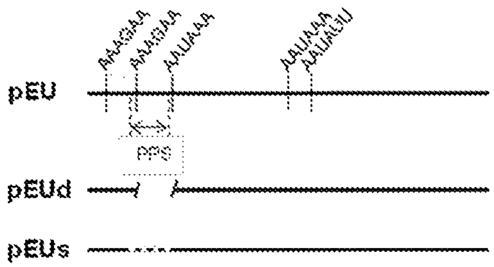
FIGS. 8A and 8B, in accordance with certain embodiments, show the effect of deletion or substitution of PPS on Ext terminator function.
Figure 8B:
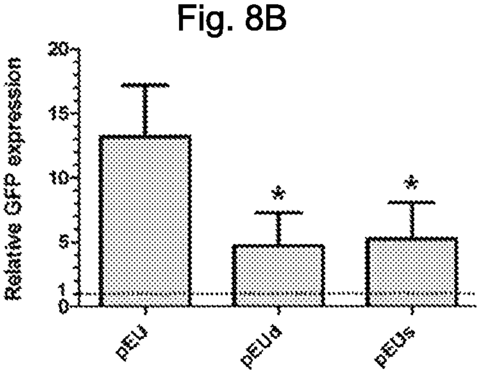

Deletion construct pEU3 (nt 465-731) was designed to include the fourth and fifth NUEs, but removes their upstream regions. Construct pEU3 showed no detectable level of GFP expression, indicating that the identified major polyA site, its putative NUE, and its downstream sequence alone were not sufficient to support gene expression. Inspection of this sequence reveals an UG-rich region, typical of plant FUEs that is well conserved among other plant extensin terminator sequences. This region also contains the alternative polyadenylation site. Therefore, both polyadenylation sites may have been disrupted by this deletion. To further confirm this result, construct pEU4 (nt 349-731) was tested. pEU4 contains the fourth and fifth NUEs, but additionally contains the larger FUE-like region. While this construct had restored activity similar to pEU2, it was still drastically reduced from the full-length construct, indicating that the first 97 nucleotides of the intronless extensin terminator are also essential for high levels of gene expression. Collectively, these data indicate that multiple regions of the Ext terminator are essential for its function, including canonical FUE, NUE, and CE regions, but also a region containing an atypical polypurine-rich region sequence ~175 nt upstream from the major polyadenylation sites. To determine whether this region contributed to the enhancement provided by the extensin terminator, we deleted or substituted the polypurine sequence and tested its effects on GFP expression (FIGS. 8A and 8B). For the substitution, some A residues were replaced with T, while maintaining the segment length. Upon deletion or substitution, the levels of GFP expression were substantially decreased (36-40% activity remained), yet they were still 4.7-5.2-fold higher than with the construct using the NOS terminator. These data indicate that the polypurine sequence is also an important element contributing to the enhancing effect of the Ext terminator.

g. Discussion

Figure 3C:
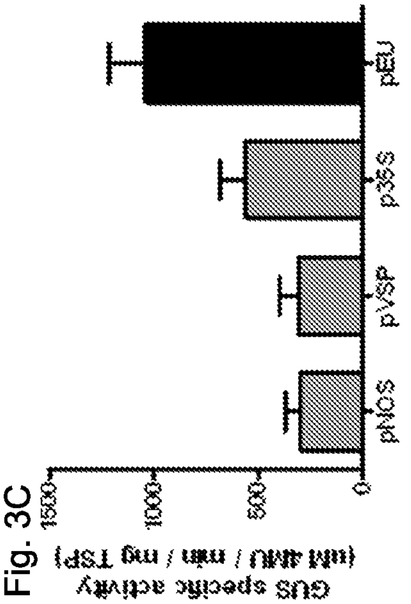

Pre-mRNA 3' end processing is an essential step in the expression of genes and is greatly affected by transcription terminators. Hence, careful selection of an optimal terminator is important for high yield recombinant protein production. Extensins are highly abundant components of the plant cell wall. Additionally, a genome-wide analysis of mRNA stability in *A. thaliana* found that extensin mRNAs were often highly resistant to degradation (Narsai et al 2007). These factors, as well as the unusual presence of an intron, led us to evaluate the tobacco Ext terminator for its potential to enhance transgene expression. When the native intron was removed, the Ext terminator produced higher levels (up to 13.5-fold) of transient transgene expression from three transgenes, GFP, NVCP, and GUS, compared to other commonly used gene terminators. Interestingly, the three transgenes showed similar expression level patterns in coordination with the tested terminators; i.e., all transgenes showed the highest expression level with the Ext terminator, followed in order by the 35S, VSP, and NOS terminators (FIGS. 3A-3C).

However, the magnitude of the difference varied between different transgenes, suggesting that if gene-specific effects exist, their effects are small compared to the intrinsic efficiency of each terminator. The NOS terminator is known to contain a cryptic poly(A) site that is only functional if a heterologous FUE is present upstream, which could be provided by some transgenes but not others (Sanfacon et al 1994). In agreement with our results in *N. benthamiana*, we found that the intronless extensin terminator strongly outperformed the 35S and NOS terminators in both its native tobacco and in lettuce, although again the magnitude of the enhancement varied. We did not directly address the effect of the 5' UTR on the efficiency of the Ext terminator, but the enhancing effect of the Ext terminator was not obviously affected by the 5' UTR, considering that the GFP and NVCP expressing vectors contained the TEV 5' UTR, while the GUS constructs did not. Additionally, we have found the Ext terminator to support very high levels of transgene production when used in conjunction with diverse plant, viral, and human 5' UTRs (Diamos et al 2016). These results demonstrate that the intronless extensin terminator is a highly effective terminator in multiple plant species and transgene contexts.

In addition to terminators, introns can also significantly affect gene expression. For example, some introns boost expression by containing enhancer elements or through a poorly defined process termed intron-mediated enhancement (IME) (Rethmeier et al 1997; Rose 2008). Conversely, some introns are required for tissue specific or developmentally restricted gene expression: introns in the *Arabidopsis* agamous (AG) gene and the Seedstick (STK) gene restrict AG and STK expression to specific tissues within the flower (Sieburth and Meyerowitz 1997; Kooiker et al 2005); and an intron in the *Arabidopsis* floral repressor Flowering Locus C (FLC) gene reduces FLC expression in response to vernalization (Sheldon et al 2002). It has been observed that the expression of Ext is regulated tissue-specifically and developmentally and is induced by various stress conditions (Showalter et al 2010; Hirsinger et al 1997). The presence of an intron in the 3' UTR of the Ext gene and its regulated expression might imply the involvement of the intron in the regulated Ext expression. Additionally, plant 3' UTRs containing introns have been shown to activate the nonsense-mediated decay pathways, sometimes resulting in decreased mRNA accumulation (Kertesz 2006). We showed that the Ext intron might have regulatory function on transient transgene expression in a context-dependent manner.

Specifically, the intron produced a deleterious effect (up to 70% decrease) when present in the Ext terminator but showed a slight increase when used in combination with NOS terminator (FIGS. 2A-2B). Consistent with these data, Menossi et al. (2003) reported the tissue dependent regulatory function of Maize HRGP gene 3' UTR: it increased GUS expression in fast-growing coleoptiles, but decreased GUS expression in maize suspension cells. Additionally, the extent to which nonsense-mediated decay is activated by the presence of an intron in the 3' UTR varies in a context-dependent manner (Kertesz 2006). Further studies of the Ext intron may provide valuable insight into the intron-mediated regulation of gene expression.

We showed that the Ext 3' UTR substantially reduces the level of readthrough transcripts compared to other terminators (FIGS. 5A-5C). Although limited transcription readthrough (~1% of transcripts) is a normal phenomenon of plant gene expression (Xing et al 2010), there are strong data indicating that readthrough transcripts have negative effects on gene expression.

For example, readthrough transcripts can trigger RDR6-mediated RNA silencing, which leads to a cascade of mRNA degradation (Luo and Chen 2007). Best studied in this regard is the GUS transgene expression in *A. thaliana*. A GUS transgene without a terminator produced readthrough mRNA and consistent RDR6-dependent RNA silencing. However, this phenomenon was resolved when two 3' terminators were placed 3' of the GUS transgene: the level of readthrough transcripts and GUS-specific small interfering RNA were decreased, resulting in higher GUS expression. Enhancement of transient gene expression from minimal cassettes using a double terminator was also suggested to be correlated with the reduction in aberrant RNA formation and therefore prevention of the triggering of post transcriptional gene silencing (PTGS) via the RDR6 pathway (Beyene G et al 2011). This mechanism was further characterized by Baeg et al (2017), showing that aberrant mRNAs lacking polyA tails are specifically selected for amplification by RDR6.

Mapendano et al. (2010) demonstrated another possible mechanism whereby readthrough transcripts mediated down regulation of gene expression. When the poly(A) signal was mutated, RNA polymerase II (RNAPII) complexes were found in the readthrough region of the mutated gene. This readthrough RNAPII, engaged on the mutated transcription units, sequesters the transcription initiation/elongation factors, and leading to their depletion at the promoter, thereby preventing transcript reinitiation. Based on these references and our data showing that the Ext terminator decreases the level of readthrough transcripts and increases mRNA accumulation, we hypothesize that the Ext terminator increases transgene expression at least in part by preventing the activation of gene silencing by RDR6 and/or by stimulating continued transcription.

The Ext 3' UTR contains five putative NUEs (FIG. 6). Sequence analyses of the 3' end of transgene transcripts revealed that most transcripts (86%) are polyadenylated at one of two YA dinucleotides shortly after the fourth NUE, which consists of a canonical AAUAAA motif. The fourth NUE resides 25 nt upstream from the cleavage site, which is typical of reported plant NUEs. While the AAUAAA NUE motif is very common in mammals and is still the single most abundant NUE motif identified in plants, it has been found to direct polyadenylation in only 10% of *Arabidopsis* transcripts (Loke et al 2005). Phylogenetic analysis showed that the general structure of the Ext terminator is found among many *Nicotiana* species, but in particular the region between the intron and the major polyA site is well conserved in *S. tuberosum* (79% identity), *C. annum* (76% identity), *S. lycopersicum* (73% identity), and *S. pennellii* (72% identity). Alignment of this region revealed that the AAUAAA motif was strongly conserved, supporting our data indicating that it functions as the dominant polyA site. In addition to this site, we found that a minority of Ext terminator transcripts were polyadenylated >60 nt downstream of the third putative NUE (also AAUAAA). However, the typical positioning of a NUE is 10-40 nt upstream from the poly(A) site, suggesting that an atypical NUE may instead direct its polyadenylation. Plant NUEs are generally A/AU-rich, but they tolerate significant degeneracy (Mogen et al 1991; Loke et al 2005). Thus, an unusual motif, such as the "AAGUUA" located 23 nt upstream from the infrequently utilized poly(A) site, may inefficiently direct 3'-end processing in a minority of Ext transcripts. This alternative polyadenylation site was also strongly conserved among related genes, suggesting alternative polyadenylation may be a general feature of plant extensins.

We performed a deletion analysis to identify which regions of the Ext terminator are necessary for its function (FIG. 7). The importance of the identified major polyadenylation site was supported by deletion construct pEU2, which showed a drastic, but not complete, reduction of Ext activity when the region containing the fourth NUE was removed. However, pEU2 retained the infrequently used polyadenylation site at nt 424 and its upstream sequence, which may explain its residual activity despite loss of the dominant polyadenylation site. These findings suggest that although an alternative polyadenylation site exists in the Ext terminator, it cannot compensate for the loss of the dominant polyadenylation site.

Plant polyadenylation requires the coordinated action of multiple regions upstream and downstream from the cleavage and polyadenylation site. Construct pEU1, which deleted the region downstream from the polyadenylation site, had greatly reduced expression (FIG. 7), in agreement with previous studies showing that U-rich regions downstream from the cleavage site are important for proper terminator function (Dong et al 2007). pEU3 included the dominant polyadenylation sites and their respective NUE, and yet had no detectable activity. Inspection of the upstream sequence removed in construct pEU3 revealed a UG-rich region located ~60-80 nt upstream from the cleavage site, typical of plant FUEs (Loke et al 2005), which was generally conserved across other homologous Ext genes. While including this putative FUE in pEU4 restored some of the activity of the terminator (~16%), our data clearly show that a region ~175 nt upstream from the identified polyA sites is also essential for optimum functioning of the extensin terminator.

The extensin terminator contains an unusual 45 nt polypurine sequence (PPS) in this upstream region that strongly affects its function. Deletion or substitution of the PPS caused a large ~60% decrease in GFP expression (FIG. 8*b*). Despite the enhancement provided by the PPS, the deletion construct lacking the PPS still outperformed all other tested terminators, indicating that the PPS alone does not account for the remarkable enhancement provided by the Ext terminator. The PPS contains a potential NUE, however no poly(A) sites were found in proximity to the PPS, suggesting that this NUE is not active. Additionally, the PPS shares no similarity to other known terminator elements, suggesting that its enhancing effect is due to an as of yet unidentified mechanism. The PPS is present at varying lengths in many *Nicotiana* species' Ext genes, however it is substantially shorter in the Ext genes from other sequenced plant species. Additionally, even among *Nicotiana* extensin terminators, the PPS is particularly long in tobacco. Further work is needed to determine whether the PPS is functional in Ext genes from other plant species, and whether the length of the PPS is an important contributing factor to its enhancing activity.

In conclusion, we find that the production of recombinant proteins in plants is enhanced by use of the Ext terminator, which increases transgene expression up to 13.5-fold compared to commonly used terminators when its naturally occurring intron is removed. The increased gene expression was associated with a reduction in readthrough transcription, and an increase in mRNA accumulation. The high activity of the intronless Ext terminator requires a NUE region consisting of a canonical AAUAAA motif 25 nt upstream from the dominant poly(A) site and surrounding CE, as well as a FUE-like UG-rich region located 60-80 nt upstream of the cleavage site, as well as an unusual polypurine rich region ~200n t upstream of the cleavage site. An infrequently utilized alternative polyadenylation site was also identified. This work highlights the importance of the terminator in controlling gene expression, and we anticipate that the enhancing effect of the Ext terminator will be broadly applicable to plant-based recombinant protein expression systems.

Figure 10A:
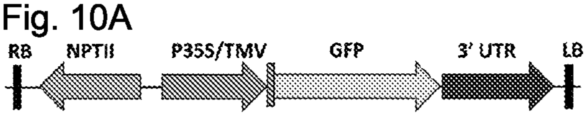
FIGS. 10A and 10B, in accordance with certain embodiments, show evaluations of a variety of 3' UTRs on GFP production.

2. Other Terminators and Chimeric 3' Flanking Regions a. Evaluation of Diverse Terminators on GFP Production To systematically evaluate diverse terminators, we constructed expression vectors using 20 different terminators from plant and viral sources, placed 3' of a GFP reporter gene, which was driven by the strong 35S promoter and tobacco mosaic virus 5' UTR (FIG. 10A). These constructs were delivered to *N. benthamiana* leaves by agroinfiltration and evaluated for GFP production. To minimize leaf-to-leaf variation, each leaf was also infiltrated with a GFP vector containing the intronless tobacco extensin terminator (EU) as an internal control, which we previously found to be a potent enhancer of gene expression (Diamos et al., 2016; Rosenthal et al., 2018)

Figure 10B:
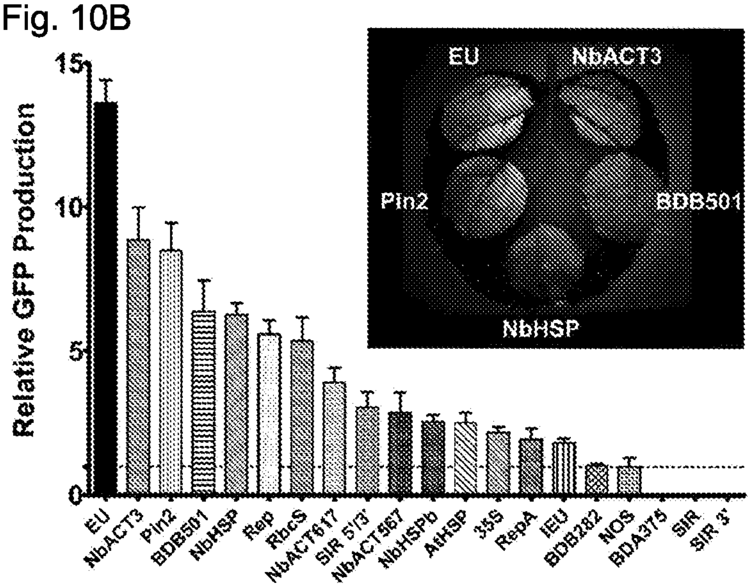

While much previous work used the NOS and 35S terminators, the *A. thaliana* 18.2 kDa heat shock protein terminator (AtHSP) was reported to enhance transgene production compared to the NOS terminator (Nagaya et al., 2010). In agreement with these results, we found that the AtHSP terminator provided a 2.5-fold increase in GFP production compared to the NOS terminator (FIG. 10B). Also consistent with previous work in transgenic potato (Richter et al., 2000), the potato pinII 3' UTR provided a very strong 8.5-fold increase compared to the NOS terminator (FIG. 10B). The rubisco small subunit (rbcS) 3' UTR from pea showed a 5.4-fold enhancement. These data demonstrate that many terminators from diverse plant species have high activity in *N. benthamiana.*

To identify new candidates, a genome-wide study of mRNA stability levels in *A. thaliana* (Narsai et al., 2007) was used to locate genes with potentially stability-enhancing 3' UTRs. We identified a *N. benthamiana* homolog of the *A. thaliana* 17.6 kDa class II heat shock protein (At5g12020). The 3' flanking region from this homolog (referred to as NbHSP) was highly active, increasing reporter gene expression by 6.3-fold compared to the NOS terminator, more than doubling the enhancement provided by the AtHSP terminator (FIG. 10B). We also identified an *N. benthamiana* homolog of *A. thaliana* actin 7 (At5g09810), referred to as NbACT3. While the downstream 617-nt region of NbACT3 enhanced expression by 3.9-fold compared to NOS, extending the 3' UTR to include more downstream sequence (1044 nt) resulted in a large 8.9-fold enhancement (NbACT3, FIG. 10B).

Many of the most highly active genetic elements in recombinant protein production systems are derived from viral sources. Therefore, we investigated the potential of viral terminators to enhance gene expression. The downstream short intergenic region (SIR) from the coat protein gene of bean yellow dwarf virus (BeYDV) showed no intrinsic terminator function by itself, or when additional downstream viral sequence (SIR 3') was included (FIG. 10B). However, when an upstream region (SIR 5'/3') from the bean yellow dwarf virus coat protein coding sequence was also included, it was highly functional, providing GFP production 3-fold greater than the NOS terminator (FIG. 10B). These data suggest that upstream elements present in the BeYDV coat protein gene are required for proper 3' end processing. The downstream sequences from the BeYDV rep and repA genes were also found to be highly active, providing a 5.6-fold and 2-fold respective enhancement. To test sequences from other geminiviruses, the terminators of bean dwarf mosaic virus (BDMV) genes were also investigated. A 282 nt sequence including the 3' end of the nuclear shuttle protein, the intergenic region, as well as the 3' end of the movement protein (BDB282) performed similarly to the NOS terminator. However, when an additional 200 nt of the downstream movement protein sequence was included (BDB501), it provided a 6.4-fold enhancement. A construct containing the BDMV coat protein downstream sequence alone was not functional, again suggesting that necessary signals may also reside in the gene coding sequence upstream from the terminator.

Taken together, these results show that many 3' UTRs from diverse sources exceed the enhancement provided by the commonly used NOS or 35S terminators, at least in a transient expression system in *N. benthamiana* leaves. Consistent with our previous work, the EU terminator outperformed the other 19 3' UTRs tested, providing a 13.6-fold increase compared to the NOS terminator, indicating that it is a uniquely potent enhancer of gene expression.

b. Combined Gene Terminators Strongly Enhance GFP Production

A double terminator consisting of the 35S terminator fused to the NOS terminator greatly enhanced protein production in various plant species compared to either terminator alone (Beyene et al., 2011). To investigate the potential for tandem terminators to synergistically enhance recombinant protein production, we tested combinations of those previously tested in FIG. 1B. We found an 18.4-fold enhancement by the 35S-NOS double terminator compared to the NOS terminator alone (FIG. 11), exceeding the highest production by the best single terminator. Interestingly, reversing the position of the two terminators (NOS-35S) provided a much lower 11.2-fold enhancement, but still greatly exceeded the GFP production obtained with either terminator alone.

Figure 11:
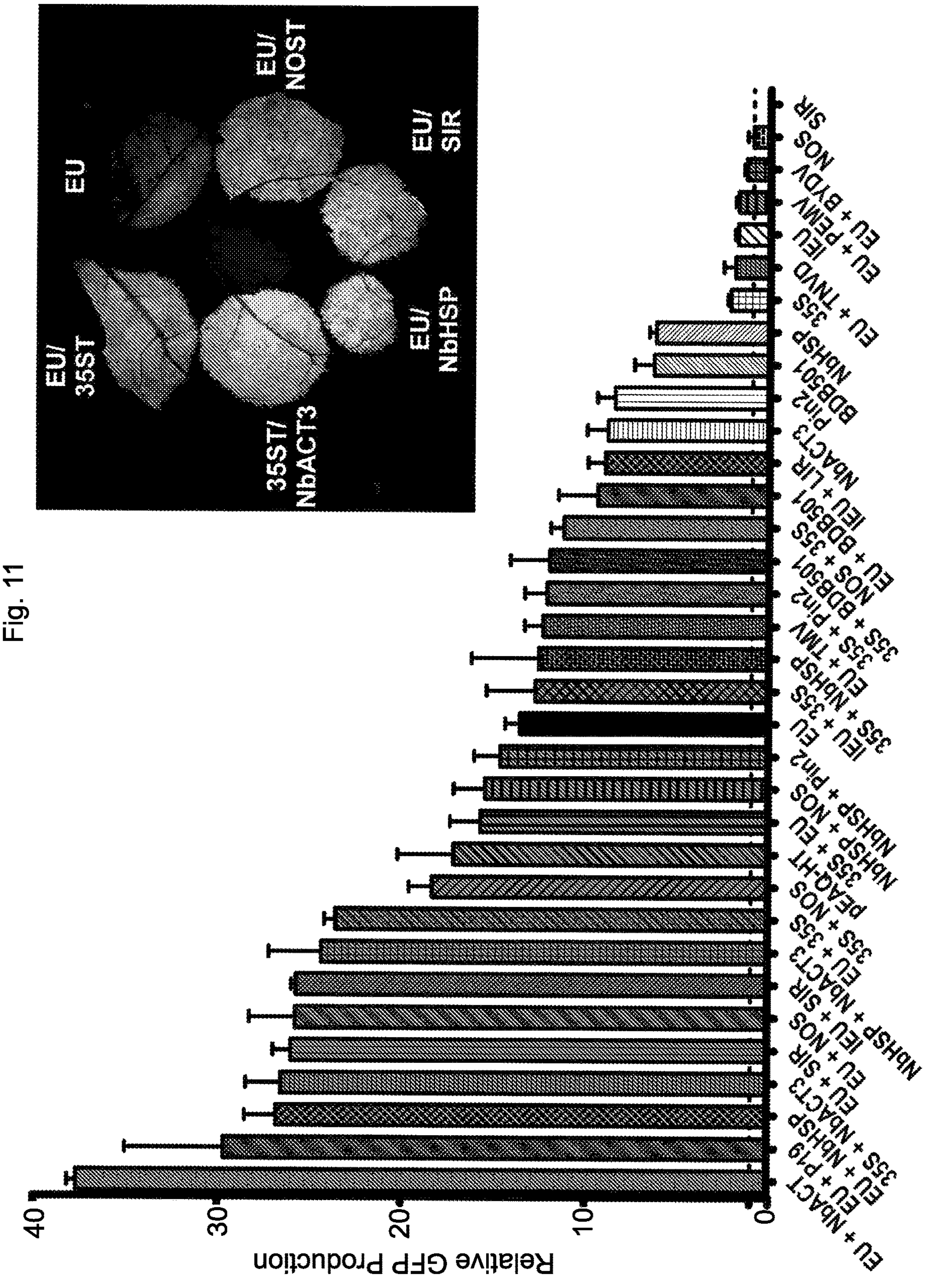
FIG. 11, in accordance with some embodiments, shows that double terminators strongly enhance GFP gene expression. Nonreplicating vectors containing different double terminators downstream from the GFP gene were agroinfiltrated into *N. benthamiana* leaves and analyzed for GFP production at 5 DPI. The filled bars indicate double terminators. Data shown are means±standard error of 3-4 independently infiltrated leaves. The abbreviations refer to the same as those in FIG. 10B. BYDV refers to the barley yellow dwarf virus 3' UTR. PEMV refers to the pea enation mosaic virus 3' UTR. As used in FIG. 11, TNVD refers to the tobacco necrosis virus-D 3' UTR; TMV refers to the tobacco mosaic virus 3' UTR; and LIR refers to the long intergenic region from bean yellow dwarf virus.

Fusion of 35S with pinII, NbHSP, and BDB501 3' regions all substantially enhanced protein production compared to either terminator alone. However, despite the individual superiority of each of these terminators compare to NOS, when paired with 35S, none exceeded the GFP production of 35S-NOS (FIG. 11, compare 35S-Pin2, 35S-NbHSP, 35S-BDB501, and 35S-NOS). In contrast, fusion of the individually strong NbACT3 terminator to the 3' end of either the 35S or NbHSP terminators resulted in a potent enhancement of GFP production, exceeding the production of 35S-NOS (FIG. 11).

As the extensin EU terminator was the best individual terminator identified, we evaluated its potential combined with other terminators. Addition of either the NbHSP, NOS, or 35S terminators to the 3' end of the EU terminator nearly doubled the GFP production provided by EU alone, exceeding the gene expression provided by 35S-NOS. The two best individual terminators, EU and NbACT3, when combined, exceeded all other combinations, providing a remarkable 37.7-fold increase compared to NOS alone (FIG. 11, EU+NbACT3). Interestingly, although the 35S terminator performed best when placed 5' of the NOS terminator, the opposite was found when paired with EU: the enhancement provided by 35S-EU was significantly lower than EU-35S (FIG. 11). Furthermore, addition of BDB501 to EU resulted in a slight decrease in expression (FIG. 11). Therefore, these results indicate that terminators placed in tandem interact either synergistically or antagonistically, in a context-dependent manner.

Figure 12:
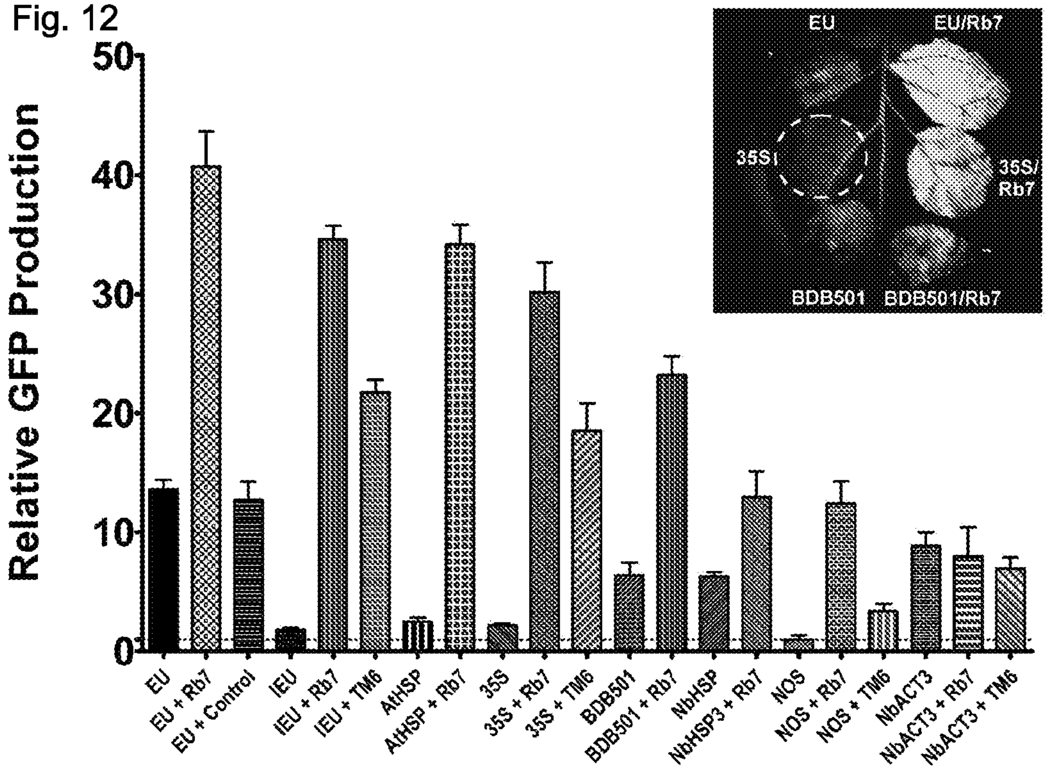
FIG. 12, in accordance with some embodiments, show that chromatin scaffold/matrix attachment regions (MAR) strongly enhance GFP expression. Nonreplicating GFP vectors containing either the tobacco Rb7 or tobacco TM6 MAR sequences inserted 3' of the gene terminator were agroinfiltrated into the leaves of *N. benthamiana* and evaluated for GFP production at 5 DPI. Data shown are means±standard error of 3-4 independently infiltrated leaves. "EU+Control" indicates DNA sequence obtained from an inverted region of the Norwalk virus capsid protein coding sequence was inserted 3' of the EU gene terminator in place of the Rb7 MAR.

Previously, we found that the 5' and 3' UTRs from the RNA viruses barley yellow dwarf virus (BYDV) and pea enation mosaic virus (PEMV) severely inhibited expression in *N. benthamiana* leaves using a replicating system containing the extensin terminator (Diamos et al., 2016). A non-replicating expression system based on the 5' and 3' UTRs from cowpea mosaic virus (CMPV) was reported to enhance gene expression largely due to incorporation of the viral 3' UTR before the NOS terminator (Sainsbury and Lomonossoff, 2008; Meshcheriakova et al., 2014). In this study, we evaluated virus-derived 3' UTRs in nonreplicating vectors. Similar to our results with replicating vectors, we found that the 3' UTRs from PEMV, BYDV, and tobacco necrosis virus D strongly inhibited gene expression when inserted downstream from the EU terminator, and the TMV 3' UTR had a negligible effect on gene expression (FIG. 11). In agreement with the results of Sainsbury et al., pEAQ-HT-GFP, which contains the cowpea mosaic virus 5' and 3' UTRs, provided a 17.1-fold increase compared to NOS alone (FIG. 12). However, this vector also contains the P19 suppressor of RNAi silencing. Coinfiltration of EU with P19 provided a 29.9-fold increase compared to NOS (FIG. 11, compare EU and EU+P19). The 3' UTRs derived from DNA viruses also performed very well. While the BeYDV SIR showed no terminator function by itself, addition of the SIR to the 3' end of EU nearly doubled its GFP production. Interestingly, although the intron-containing extensin terminator (IEU) performed very poorly on its own compared to the intronless version (EU), addition of the BeYDV SIR completely negated the detrimental effect of the intron (FIG. 10B, compare IEU+SIR and EU+SIR). Addition of the 35S terminator to IEU also greatly enhanced expression, however in this case the total yield was lower than the comparable vector with the intron removed (FIG. 11, compare IEU+35S and EU+35S). These results indicate that viral 3' flanking regions, have potential to strongly increase gene expression when inserted downstream from the gene terminator.

c. Matrix Attachment Regions are Potent Enhancers of Transient Expression

While MAR has been widely used in transgenic expression systems, there are few reports of their use in transient expression systems. We found that the tobacco Rb7 MAR strongly enhanced transient expression in a replicating geminiviral transient expression system when placed downstream from the gene terminator (Diamos et al., 2016). To more fully characterize the potential for MAR to function in transient expression systems, the tobacco Rb7 and TM6 MAR were inserted into nonreplicating GFP expression vectors in combination with 8 different gene terminators.

Figure 17A:
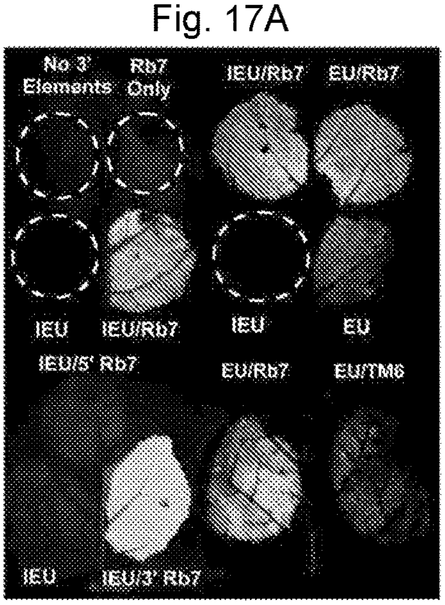
FIGS. 17A and 17B characterizes Rb7 and TM6 MARs.

Insertion of the Rb7 MAR downstream from the EU terminator resulted in a striking 3-fold enhancement of GFP production (40-fold compared to NOS alone), exceeding the best double terminator configuration (FIG. 12, compare EU and EU+Rb7). Interestingly, similar to the SIR, the Rb7 MAR also dramatically improved production of the otherwise weak IEU terminator, increasing expression 19-fold, bringing it nearly on par with the EU-Rb7 vector (FIG. 12, compare IEU, IEU+Rb7, and EU+Rb7 and FIG. 17A). To verify that the observed enhancement was unique to the Rb7 MAR, a control DNA sequence of similar size, derived from a synthetic norovirus capsid protein coding sequence, was instead inserted downstream of GFP, and found to provide no significant difference in GFP production (FIG. 12, compare EU and EU+Control). Inspection of the AT-rich Rb7 MAR sequence reveals many terminator-like elements, however in the absence of a terminator no detectable GFP activity was produced using the MAR as the sole 3' region, indicating that it does not act as a fully functional terminator (FIG. 17A). Consistent with our findings in replicating systems, positioning of the Rb7 MAR 5' of the promoter had no effect on gene expression (FIG. 17A).

We further found that Rb7 MAR provided a large enhancement when used in conjunction with the 35S (13.8-fold), AtHSP (13.6-fold), NOS (12-fold), BDB501 (3.6-fold), or NbHSP (2-fold) terminators (FIG. 12). In the absence of the Rb7 MAR, the NbHSP terminator provided nearly 3-fold more expression than the 35S terminator. However, upon addition of the MAR, the 35S/Rb7 combination provided double the expression of NbHSP/Rb7 (FIG. 12). Interestingly, while the Rb7 MAR substantially enhanced 7 of the 8 terminators tested, the NbACT3 terminator was unaffected by addition of the Rb7 MAR.

The tobacco TM6 MAR reportedly exceeded the enhancing effect of the Rb7 MAR in transgenic tobacco (Ji et al. 2013). To test the TM6 MAR in our transient expression system, the full sequence was cloned from tobacco plants and inserted in place of the Rb7 MAR. The TM6 MAR enhanced GFP production when paired with the 35S, NOS, or IEU terminators, but not with the NbACT3, similar to our findings for the Rb7 MAR (FIG. 12, purple bars). However, the magnitude of the enhancement provided by the TM6 MAR was significantly less than that of the Rb7 MAR in all combinations tested (FIG. 12 and FIG. 17A).

Figure 17B:
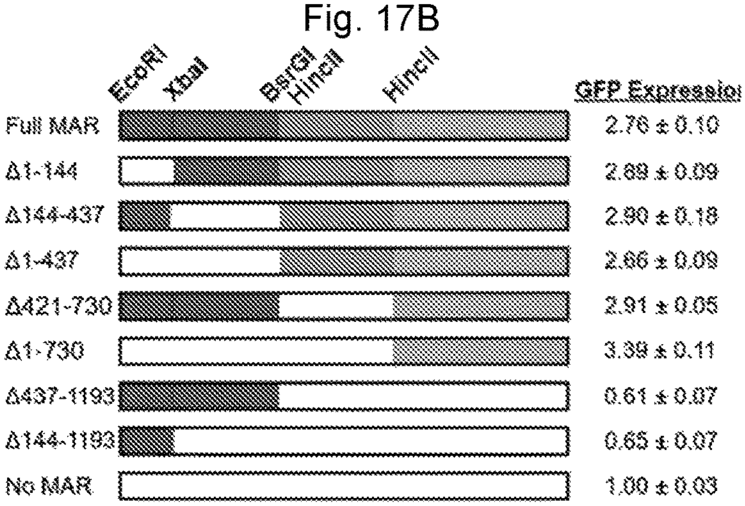

Using deletion studies, we investigated which regions of the 1193-bp Rb7 MAR were responsible for the observed enhancement. Deletion of nucleotides 144-1193 or 437-1193 eliminated the enhancing effect of the Rb7 MAR, however deletion of nucleotides 1-144, 144-437, 1-437, 421-730, or 1-730 did not impair MAR activity (FIG. 17B). In fact, a small but repeatable increase in the enhancement provided by the Rb7 MAR was observed upon deletion of nucleotides 1-730 (FIG. 17B). These data indicate that a relatively short region at the 3' end of the Rb7 MAR is responsible for all of the observed enhancement in this system.

d. Synergistic Enhancement of Combined 3' Flanking Regions

Figure 13:
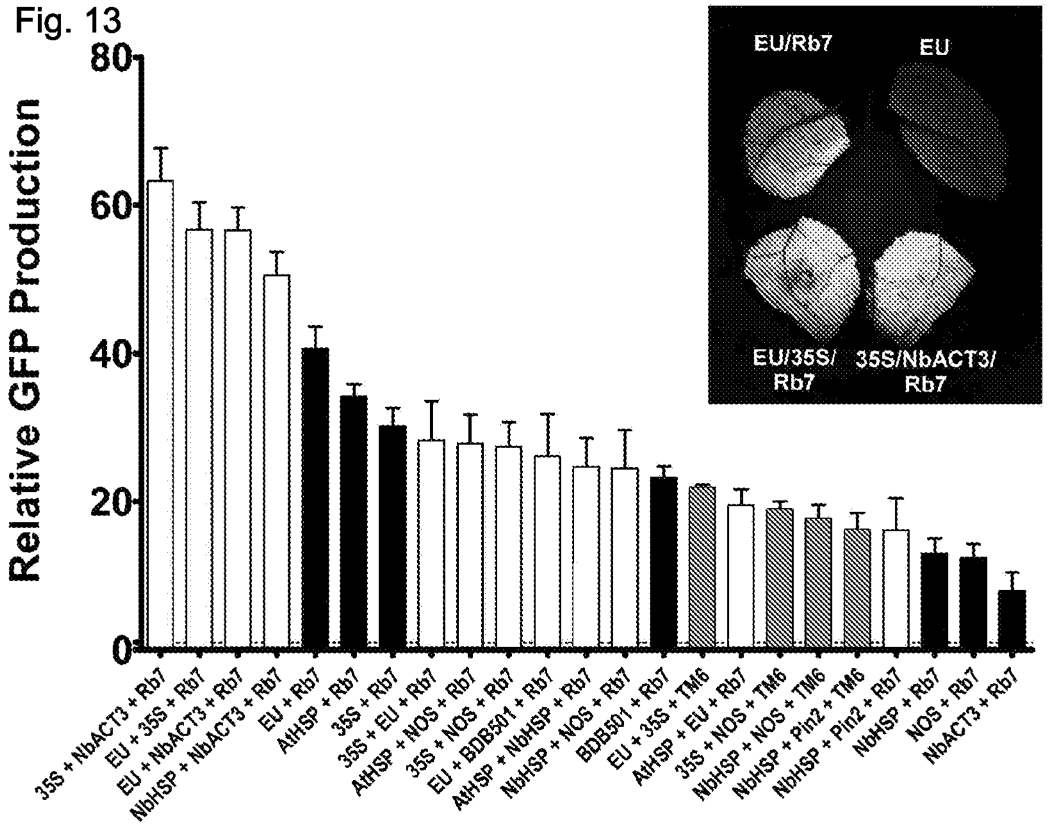
FIG. 13, in accordance with some embodiments, show that combined 3' UTRs strongly enhance GFP expression. Nonreplicating GFP vectors with combined terminators were created, agroinfiltrated into the leaves of *N. benthamiana*, and evaluated for GFP production at 5 DPI. Data shown are means±standard error of 3-4 independently infiltrated leaves. White bars indicate double terminators combined with Rb7 MAR; gray bars indicate double terminators combined with TM6 MAR; and black bars indicate single terminators combined with Rb7 MAR.

We investigated the potential for double terminators and the Rb7 or TM6 MAR to further increase gene expression when used in combination. Addition of the Rb7 MAR to the EU-35S double terminator significantly increased the expression provided by the double terminator alone (2.4-fold), and by either individual terminator with or without Rb7 MAR (FIG. 13, compare EU+Rb7, 35S+Rb7, EU+35S+Rb7 and FIG. 3 EU+35S). This represents a 56.7-fold total increase compared to the NOS terminator. However, the fold-increase provided by addition of the Rb7 MAR to EU-35S was smaller than the increase provided by addition of Rb7 to either EU or 35S alone (FIG. 17A). Interestingly, despite the failure of the Rb7 MAR to enhance expression of the NbACT3 terminator by itself, the 35S-NbACT3 double terminator was further enhanced by 2.4-fold upon addition of the Rb7 MAR, more than doubling the expression provided by 35S-Rb7 (FIG. 13). EU-NbACT3, the highest expressing double terminator, was also improved by 1.5-fold upon addition of the Rb7 MAR.

While the 35S and NOS terminators were substantially improved when combined in either orientation (FIG. 12), and while addition of the Rb7 MAR to the 35S-NOS double terminator provided a further 1.9-fold increase in expression (compare FIG. 13 35S+NOS+Rb7 to FIG. 12 35S+NOS), the total yield of 35S—NOS-Rb7 was no better than the single terminator construct 35S-Rb7 (FIG. 12, compare 35S+NOS+Rb7 and 35S+Rb7). Similarly, although we observed a large synergy between the Rb7 MAR and the individual terminators AtHSP, EU, BDB501, and 35S, and although the expression provided by the double terminators AtHSP-EU, 35S-EU, and EU-BDB501 was enhanced by addition of the Rb7, all performed worse than EU-Rb7. Furthermore, one double terminator combination was not improved at all by the presence of a MAR. Addition of the Rb7 MAR to NbHSP-Pin2 resulted in a small 1.1-fold increase, which was not statistically significant (compare FIG. 12 NbHSP+Pin2+Rb7 to FIG. 11 NbHSP+Pin2).

e. Evaluation of Combined 3' Flanking Regions in a Replicating System

Figure 14A:
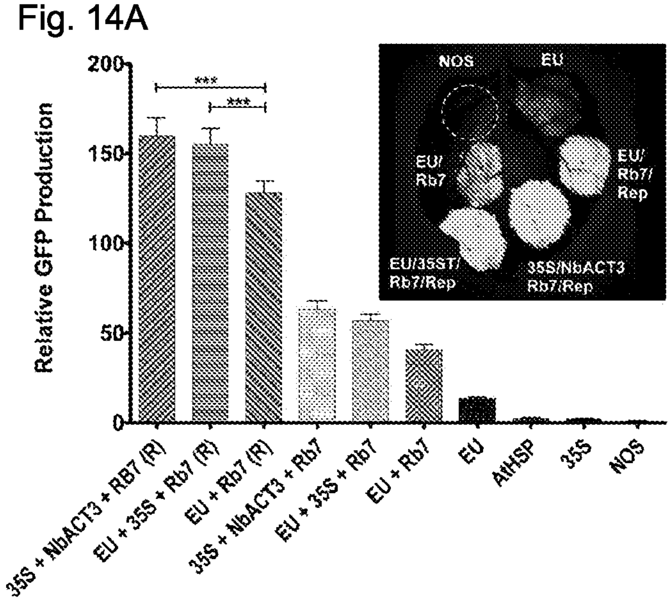
FIGS. 14A and 14B, in accordance with some embodiments, show evaluations of a variety of combined 3' UTRs in replicating vectors on GFP expression. Replicating vectors containing elements of bean yellow dwarf virus (Diamos et al, 2016) were constructed with various combined 3' flanking regions, agroinfiltrated into the leaves of *N. benthamiana*, and evaluated for GFP production.
Figure 14B:
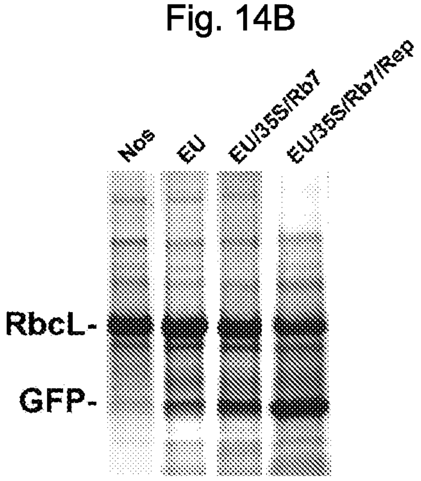
Figure 15:
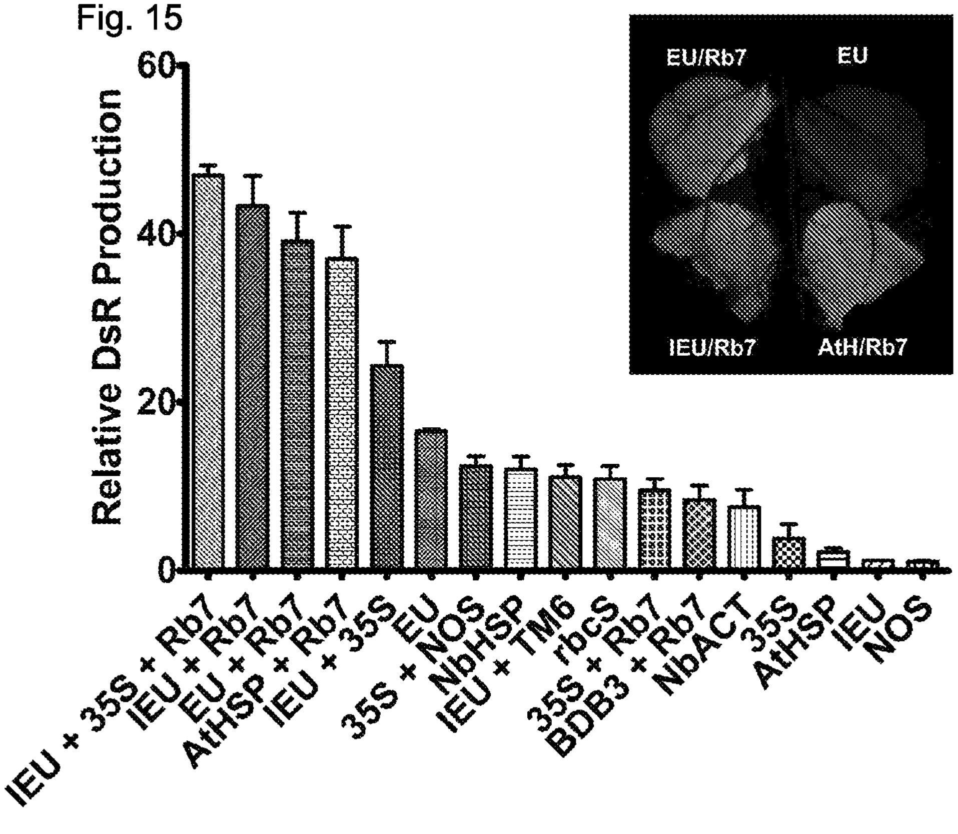
FIG. 15, in accordance with some embodiments, compares the relative DsR production of the identified 3' UTRs. Nonreplicating vectors were constructed with single, double, or MAR-containing terminators downstream from the DsRed gene and agroinfiltrated into the leaves of *N. benthamiana*. DsRed production was evaluated at 5 DPI by SDS-PAGE and UV fluorescence. Data shown are means±standard error of 3-4 independently infiltrated leaves.

Previously, we reported a plant transient expression system based on the geminivirus bean yellow dwarf virus, which enhances gene expression by increasing accumulation of DNA copies of the gene of interest (Huang et al. 2009). We found that expression was substantially increased by insertion of the extensin terminator and the Rb7 MAR, among other modifications (Diamos et al., 2016). To evaluate the potential of combined 3' UTRs to function in this system, several of the best performing 3' UTR combinations were cloned into geminiviral vectors expressing GFP. The geminiviral vector containing EU-Rb7 enhanced expression 3.1-fold more than the nonreplicating vector (FIG. 14A). Similarly, the two best nonreplicating vectors containing EU-35S-Rb7 and 35S-NbACT3-Rb7 were further enhanced 2.7-fold and 2.5-fold, respectively, when placed in geminiviral vectors (FIG. 14A). Similar to their non-replicating counterparts, in geminiviral vectors the 35S-EU-Rb7 and 35S-NbACT3-Rb7 combinations increased GFP production by up to 20% compared to a replicating vector containing only EU-Rb7 (FIG. 14A). The total GFP expression of the best construct is estimated at up to 50% total soluble protein or 3-5 g per kg leaf fresh weight (FIG. 14B).

f. Gene-Specific and Plant-Specific Activity of Single and Combined 3' Flanking Regions To determine whether the identified terminators performed similarly with a reporter gene other than GFP, vectors containing a variety of individual or combined terminators were constructed with the DsRed gene replacing the GFP gene. DsRed shares no sequence homology with GFP. For single terminators, the extensin terminator provided the highest level of gene expression (FIG. 15), in agreement with our data with GUS or Norwalk virus capsid protein (Rosenthal et al., 2018). Other terminators performed similarly as when paired with GFP, however some small differences were observed, such as the increased activity of NbHSP and 35S with DsRed compared to NOS (FIG. 15). The IEU-355 double terminator substantially exceeded the DsRed production of EU alone, however the 35S-NOS double terminator performed substantially worse with DsRed than with GFP (FIG. 15). Use of the Rb7 MAR strongly enhanced DsRed expression with most terminators, and the enhancement provided by Rb7 exceeded that of TM6 in the one case tested (FIG. 15). Interestingly, while 35S-Rb7 performed very well with GFP, it did not with DsRed.

The functionality of genetic elements often varies among species. To assess the generality of these results in other plant systems, a subset of 3' UTRs were tested in tobacco (*N. tabacum*) and lettuce. Similar to our results in *N. benthamiana*, in both tobacco and lettuce plants GFP gene expression with EU was >10-fold higher than with NOS, and EU exceeded all other single terminators tested (FIG. 16). While EU performed substantially better than all other single terminators in its native tobacco, the AtHSP, NbHSP, and NbACT3 performed nearly as well as EU in lettuce (FIG. 16). Addition of the Rb7 MAR strongly enhanced GFP expression when added to EU in tobacco and lettuce, and the 35S-NbACT3-Rb7 combination, which performed very strongly in *N. benthamiana*, also did so in tobacco and lettuce (FIG. 16). Despite its strong performance in *N. benthamiana*, IEU-355-Rb7, which contains the extensin intron, had much lower expression in tobacco (FIG. 16). Similarly, NbHSP-NbACT3 with or without Rb7 MAR performed substantially worse in tobacco than in *N. benthamiana* (FIG. 14 and FIG. 16).

g. Discussion

To more broadly assess the potential of 3' flanking regions to enhance gene expression in plant systems, we systematically compared a diverse set of terminators from various plant and viral sources. Narsai et al. (2007) reported a genome-wide analysis of mRNA stability in *A. thaliana*, showing that characteristic 3' UTR motifs are enriched in long-lived or short-lived transcripts. To rationally derive putative terminator candidates with potential to enhance gene expression, we identified *N. benthamiana* homologs of two highly stable *A. thaliana* transcripts: an 18.8 kDa class II heat shock protein gene, and an actin-like gene. Both terminators outperformed all of those frequently used previously (FIG. 10B). Since we tested only two terminators identified in this manner, we suspect that other candidates can be discovered. Overall, we found that 12 terminators exceeded the performance of 35S or NOS. Highly expressed genes from strong promoters are targets for RNA silencing (Que et al. 1997; Schubert et al. 2004), mediated by RDR6 (Beclin et al. 2002). Luo and Chen (2007) demonstrated that improperly terminated mRNAs result in RDR6-mediated silencing of the transgene, and that the use of a 35S-NOS double terminator reduced this effect while enhancing GUS expression is transgenic *A. thaliana*. Beyene et al. (2007) also found a large enhancing effect of a 35S-NOS double terminator in several plant species. While the intronless EU terminator by itself was significantly better than all 19 other individual terminators tested, we identified 8 double terminators that significantly exceeded the performance of EU alone, 7 of which significantly outperformed the 35S-NOS double terminator (FIG. 11). We found that nearly every combination outperformed either individual terminator alone, showing that tandem-linked terminators have excellent potential to enhance gene expression. Interestingly, in both tested cases, reversal of the position of the two terminators resulted in a substantial difference in expression, indicating that the observed enhancement does not arise entirely from the individual action of the two terminators, but rather on a synergistic interaction between the two terminators, which depends in part on their relative position. Furthermore, when positioned upstream from NOS, the 35S terminator performed strongly; however, the opposite was observed when paired with EU: expression was enhanced by 50% when 35S was instead positioned downstream from EU. These results indicate that the optimal position for a given terminator depends on the individual terminator with which it is paired. Further work is needed to study the individual mechanisms underlying these differences.

The 3' flanking regions from RNA viruses contain many mechanisms to enhance mRNA stability or increase translation (Fan et al., 2012; Simon and Miller 2013). However, when expressed in the plant nucleus, these 3' regions may contain cryptic splice sites and other detrimental sequences. Most of the RNA virus-derived 3' flanking regions we tested were poorly functional when transiently expressed in *N. benthamiana* leaves, except for those derived from cowpea mosaic virus. The 5' and 3' UTRs from cowpea mosaic virus were reported to be potent enhancers of protein expression (Sainsbury and Lomonossoff, 2008; Meshcheriakova et al., 2014). In general agreement, we found pEAQ-HT-GFP, which contains the NOS terminator and the cowpea mosaic virus UTRs, enhanced GFP expression 17.1-fold compared to NOS alone. However, the cowpea mosaic virus vector pEAQ-HT-GFP also contains the P19 suppressor of RNA silencing, which likely enhances RNA stability (Sainsbury et al., 2009), making direct comparisons to other 3' UTRs difficult. While pEAQ-HT-GFP provided 20% more GFP than the extensin terminator alone, it provided 40% less when extensin was also supplemented with P19 (FIG. 11). We also found that other highly expressing terminator combinations identified here were also strongly enhanced by addition of P19 (data not shown). As pEAQ-HT-GFP contains the relatively weak NOS terminator, we suspect the cowpea mosaic virus flanking regions may perform better with a stronger terminator, unless some particular synergy exists with NOS.

Flanking regions derived from nucleus-adapted DNA viruses, such as the geminiviruses, were found to be potent enhancers of gene expression, especially when used in conjunction with a functional terminator. The short 200 bp SIR from bean yellow dwarf virus showed no terminator activity by itself, but it was found to strongly increase gene expression when used in conjunction with the extensin terminator, on par with the best double terminator combinations tested. However, extending the SIR to include upstream and downstream coding sequence from the BeYDV coat and rep proteins showed that it also has strong terminator function on its own. Similar results were obtained with 3' UTRs obtained from bean dwarf mosaic virus. These results highlight the influence of the upstream gene coding sequence on 3' UTR function. Further work is needed to better characterize the enhancing potential of geminiviral 3' UTRs, and to determine whether the observed enhancing effect of the SIR is terminator-specific.

Though MAR was previously used in transgenic systems, we found the tobacco Rb7 MAR substantially improved gene expression using a geminiviral transient expression system (Diamos et al. 2016). Only a small percentage of T-DNA delivered by *agrobacterium* undergoes chromosomal integration, while the majority is transiently transcribed in the nucleus. It has been shown that the *agrobacterium* proteins VirE2, which coats the T-DNA, and VirD2, which attaches to 5' end of the T-DNA and mediates nuclear entry, both associate with cellular histones (Lacroix et al. 2008; van Heusden et al. 2015). As MAR is thought to influence chromatin structure, the association of T-DNA with histones suggests a possible mechanism by which MAR function in vectors delivered by agroinfiltration. Here, we find that both the tobacco Rb7 and TM6 elements greatly enhance transient gene expression in agroinfiltrated leaf tissue (FIG. 12). The effect of the Rb7 MAR varies in a promoter-dependent manner (Mankin et al. 2003). Similarly, we find that the effect of the MAR also varies in a terminator-dependent manner. EU was the strongest individual terminator and EU-Rb7 was the strongest MAR combination, exceeding the best double terminator by over 50%. However, while NbACT3 was the second strongest individual terminator, NbACT3-Rb7 was the lowest expressing MAR combination. Interestingly, we saw a similar effect when NbACT3 was paired with the TM6 MAR, suggesting that some enhancing activity present in both MAR is not active when paired with the NbACT3 region. All other terminators greatly benefited from addition of the Rb7 or TM6 MARs, although the magnitude of the enhancement varied in a manner that was not correlated to the individual expression level mediated by each terminator alone.

Ji et al. (2013) found that the TM6 MAR enhanced GUS expression at a level greater than the Rb7 MAR in transgenic tobacco. However, we consistently found that the Rb7 MAR increased transient expression more than the TM6 MAR. This observed discrepancy could be due to different expression systems, or different reporter genes. We found that the entire enhancing activity of the Rb7 MAR resides in a 463 bp region at its 3' end. Although a detailed characterization of the functional regions of the Rb7 MAR has not been reported, the region we found to be dispensable includes several AT-rich regions, a matrix attachment recognition sequence motif, and a topoisomerase II binding site, all of which were previously suspected to play a role in MAR function (Allen et al. 1996). Ji et al. (2013) found that deletion of similar MAR elements substantially reduced the enhancing effect of TM6. Additionally, it has been reported that the TM2 MAR functions best when placed 5' of the gene of interest (Zhang et al. 2009), whereas we found no effect of 5' insertion of the Rb7 MAR. As MAR are thought to contain multiple active regions responsible for their enhancing function, there may be differences in the key functional regions of the Rb7, TM2, and TM6 MARs, making direct comparison difficult. Alternatively, while Rb7 and TM6 are both clearly active in our transient expression system, the mechanisms by which expression is enhanced may differ between transient and transgenic systems. Further studies are needed to resolve these discrepancies.

Previously, we found that combining optimized 5' UTRs and the Rb7 MAR resulted in a synergistic enhancement of gene expression (Diamos et al. 2016). Other studies obtained favorable results by duplicating or combining highly functional genetic elements, such by tandem-linking TM2 MAR (Zhang et al. 2002) or combining the 5' UTR from alcohol hydrogenase and the AtHSP terminator (Limkul 2015). Here, we find that combining double terminators with the Rb7 MAR enhanced gene expression more than either component by itself in some, but not most, cases (FIG. 13). Particularly high synergy was observed between the Rb7 MAR and the EU-35S, 35S-NbACT3, and EU-NbACT3 double terminators, reaching very high expression levels of up to 60-fold more than the NOS terminator alone.

We saw variable effects when combining double terminators with MAR. While 35S-NOS was a relatively strong double terminator, it had little synergy when combined with Rb7. Similarly, while the AtHSP terminator had high synergy with the Rb7 MAR, double terminators containing AtHSP did not improve expression compared to AtHSP-Rb7 alone (FIG. 13). As all AtHSP double terminators tested in this study had AtHSP positioned as the upstream terminator, it is possible reversing terminator positions may result in better performance. Notably, EU-35S-Rb7 was one of the best combinations tested, but the reversed 35S-EU-Rb7 had a 50% reduction in expression (FIG. 13).

We have created a replicating transient expression system based on the geminivirus bean yellow dwarf virus, which amplifies the gene of interest to high copy number in the plant nucleus (Huang et al. 2009, Huang et al. 2010). By incorporating optimized 5' and 3' UTRs with other modifications, we have used this system to produce vaccine antigens and pharmaceutical proteins at levels greater than or similar to the highest levels reported in plant-based systems (Diamos et al. 2016). Here, we find that gene expression with the double terminator and MAR constructs 35S-NbACT3-Rb7 and EU-35S-Rb7 is improved by ~2.5-fold when placed in a replicating vector, a 20% increase compared to the best replicating construct containing only a single terminator and MAR (FIG. 14A). This represents a more than 150-fold increase compared to the original NOS vector alone, providing an estimate yield of around 40-60% total soluble protein or 4-5 mg recombinant protein per kg of leaf tissue (FIG. 14B), which appears to approach the theoretical limit achievable in a plant-based system.

The upstream gene coding sequence has been shown to interact with the 3' UTR. The NOS terminator contains a cryptic polyadenylation site that requires an upstream element to be present for its function (Sanfacon et al., 1991; Sanfacon and Hohn, 1990). We found that the intergenic regions of bean yellow dwarf virus and bean dwarf mosaic virus both require upstream coat protein coding sequence for terminator function (FIG. 10B). These results indicate that 3' UTRs may perform differently in the context of different genes of interest. Using DsRed as an alternative reporter gene to GFP with no shared homology, we found that most single or combined 3' UTRs performed similarly relative to one another, with a few notable exceptions. The 35S-NOS and 35S-Rb7 3' UTRs both performed substantially worse with DsRed than they did with GFP, however both still performed better than 35S alone. Despite these combinations performing worse, the 35S terminator alone performed better with DsRed than with GFP, and combinations with the 35S terminator positioned as the second terminator were still highly functional (FIG. 15).

Figure 16A:
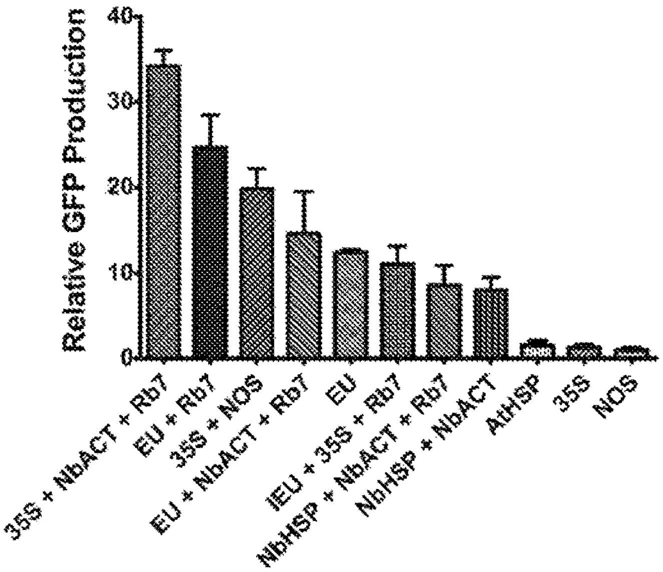
FIGS. 16A and 16B, in accordance with some embodiments, compares GFP expression of the a variety of 3' UTRs in tobacco and lettuce. Nonreplicating vectors were constructed with single, double, or MAR-containing terminators downstream from the GFP gene, and agroinfiltrated into the leaves of either tobacco (FIG. 16A) or lettuce (FIG. 16B) plants. GFP production was evaluated at 5 DPI by UV fluorescence and SDS-PAGE. Data shown are means±standard error of 3-4 independently infiltrated leaves.
Figure 16B:
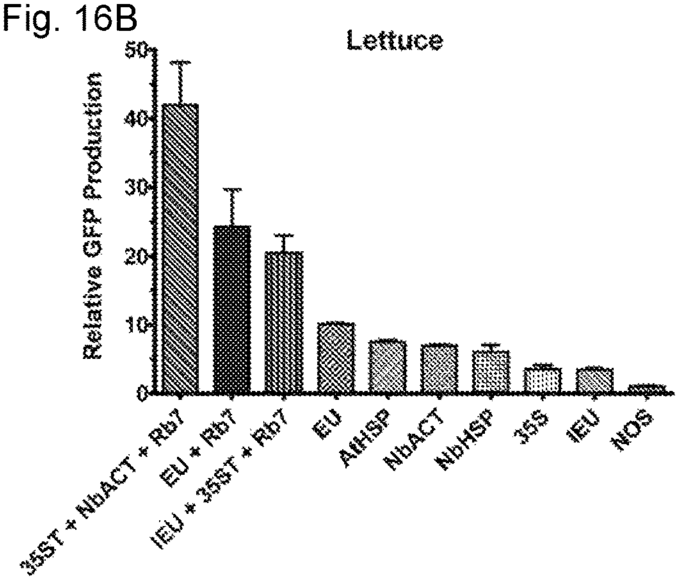

Lettuce has been shown to be a promising plant system capable of rapidly producing recombinant proteins (Lai et al., 2012; Chen et al., 2016). To further investigate the generality of our results, we also tested a variety of 3' UTRs in tobacco and lettuce. As with *N. benthamiana*, EU was the best individual terminator in lettuce. Further, combined terminators containing the Rb7 MAR substantially outperformed any individual terminator tested (FIGS. 16A and 16B). However, a few of the terminator combinations that performed very well in *N. benthamiana* performed relatively poorly in either lettuce or tobacco. As we did not test every identified combination with multiple genes or other plant systems, it is likely that other gene-specific or plant-specific effects exist that we did not discover here. Overall, our data suggests that the optimal terminator for a given system must be determined empirically. However, the potent enhancing effect of the intronless EU terminator has been demonstrated with GFP, DsRed, GUS, and Norwalk virus capsid protein, in *N. benthamiana*, lettuce, and tobacco (FIG. 10B, FIG. 15, FIG. 17A, FIG. 17B, and Rosenthal et al., 2018), indicating that the terminator is intrinsically highly active in many gene contexts. Additionally, our results clearly demonstrate that combining terminators is a highly effective strategy to improve gene expression in a variety of systems.

In conclusion, we have identified a diverse set of gene terminator regions that greatly exceed the gene expression provided by the most commonly used terminators in *N. benthamiana*, tobacco, and lettuce leaves. The intronless tobacco extensin terminator is a uniquely potent enhancer of gene expression. In nearly every case tested, double terminators outperformed either individual terminator alone, often exceeding the gene expression of the best individual terminators by more than 2-fold. We find that MAR, especially the 3' end of the Rb7 MAR, are strong enhancers of transient gene expression, and when combined with double terminators, synergistically enhance expression. Incorporating these combined terminators into a replicating geminiviral expression system has allowed us to produce recombinant proteins comparable to the highest levels ever reported in a plant-based system. The 3' UTR combinations identified here have broad potential to improve other DNA-based plant expression systems.

3. Double Terminators Enhance VLP Expression

Attempts to express the GII.4 norovirus capsid using the TMV-based magnICON system resulted in the rapid onset of cell death, and correspondingly low VLP yields of 0.3 mg per gram leaf fresh weight (LFW) (Mathew et al. 2014). The total soluble protein extractable from one gram of *N. benthamiana* leaf issue is 8-10 mg. Previously, we have reported expression of GI Norwalk capsid protein (NVCP) at 1.8 mg per gram leaf fresh weight (LFW) using bean yellow dwarf virus vectors, or ~20% of total soluble protein. To attempt production of GII.4 norovirus VLPs using optimized vectors designed to reduce cell death, bean yellow dwarf virus vectors (FIG. 18A) containing the Rb7 matrix attachment region, and the NbPsaK 5' UTR with or without reduced Rep/RepA expression (Diamos et al. 2016, and data to be published elsewhere) were infiltrated using *agrobacterium* strain EHA105 at an OD600 of 0.2 into the leaves of *Nicotiana benthamiana* and monitored for cell death. An unmodified vector without these optimizations was used as a control.

Figures 18A, 18B, 18C, 18D:
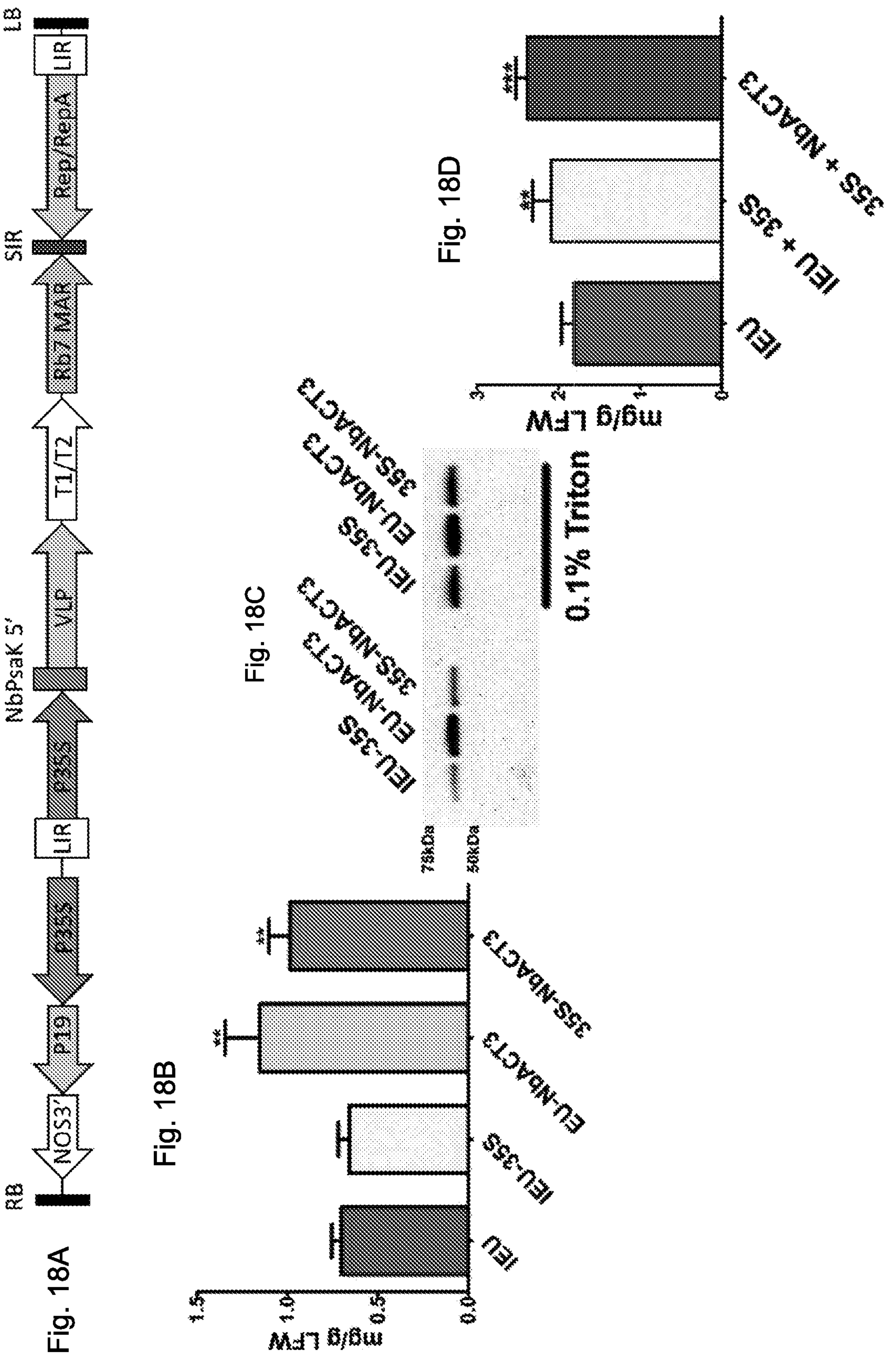
FIGS. 18A-D show that double terminators enhance VLP expression in a replicating vector derived from bean yellow dwarf virus.

Combined gene terminators, which we have found to be potent enhancers of plant transient gene expression, were tested in BeYDV vectors expressing GII.4 norovirus capsids. The gene terminators tested IEU, IEU+35S (indicated in FIGS. 18B and 18C as IEU-35S), EU+NbACT3 (indicated in FIGS. 18B and 18C as EU-NbACT3), and 35S+NbACT3 (indicated in FIGS. 18B and 18C as 35S-NbACT3). By both western blot and ELISA, the EU+NbACT3 and 35S+NbACT3 double terminators enhanced expression compared to IEU or IEU+35S. The best double terminator, EU+NbACT3, provided a 64% increase in expression, producing up to 1.1 mg/g LFW of GII.4 norovirus capsids (FIGS. 18B and 18C). Addition of 0.1% Triton X-100 detergent enhanced norovirus capsid recovery (FIG. 18C). Production of GI NVCP was also tested with the IEU, IEU+35S, and 35S+NbACT3 double terminators. Like GII.4 VLP, 35S+NbACT3 increased expression 30% compared to IEU, resulting in a yield of 2.3 mg/g NVCP, or up to 28% total soluble protein.

Figure 19:
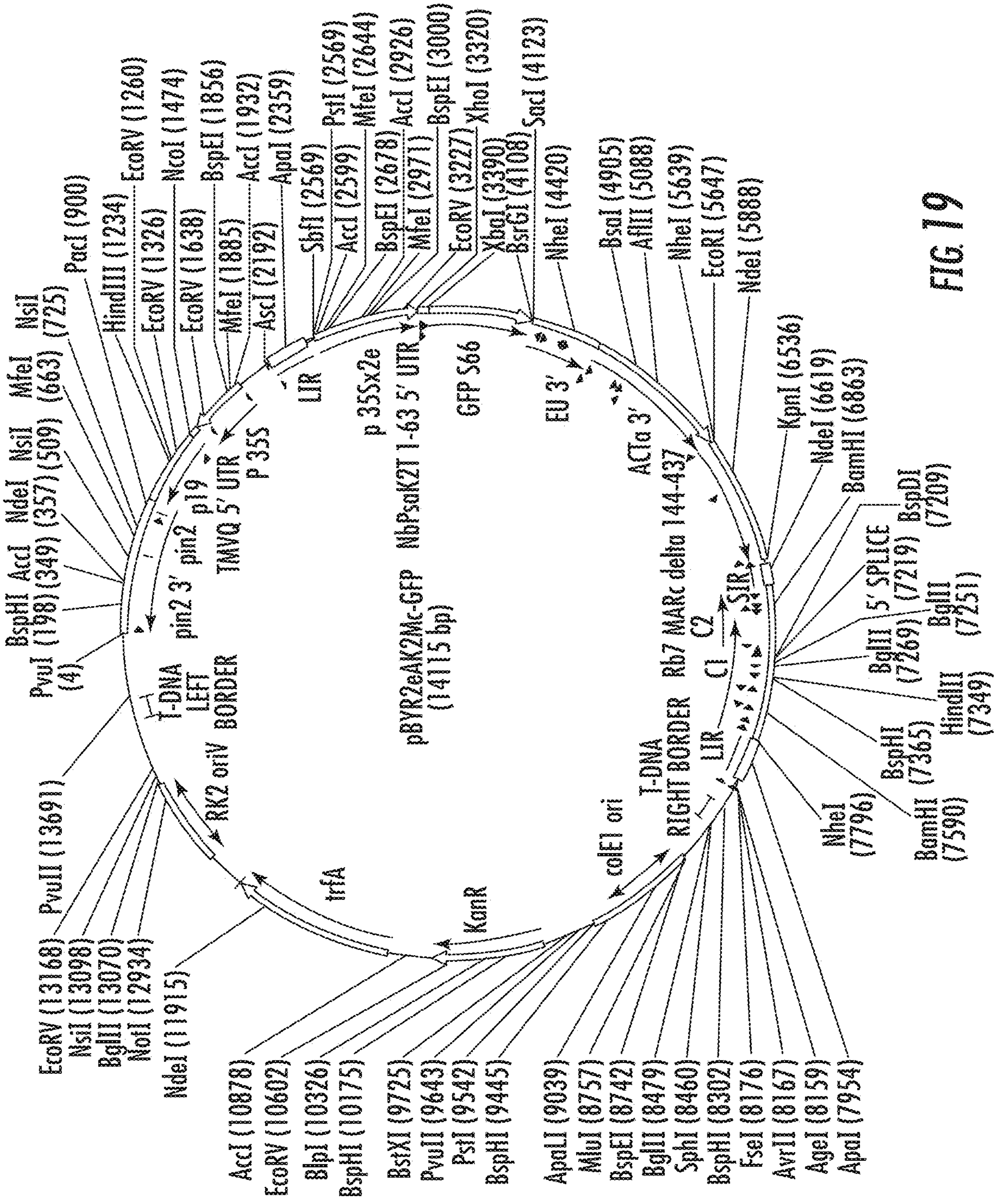
FIGS. 19-21 depict schematics of three exemplary plasmids comprising, in its expression cassettes, the 3' UTR comprising a double terminator and MAR.
Figure 20:
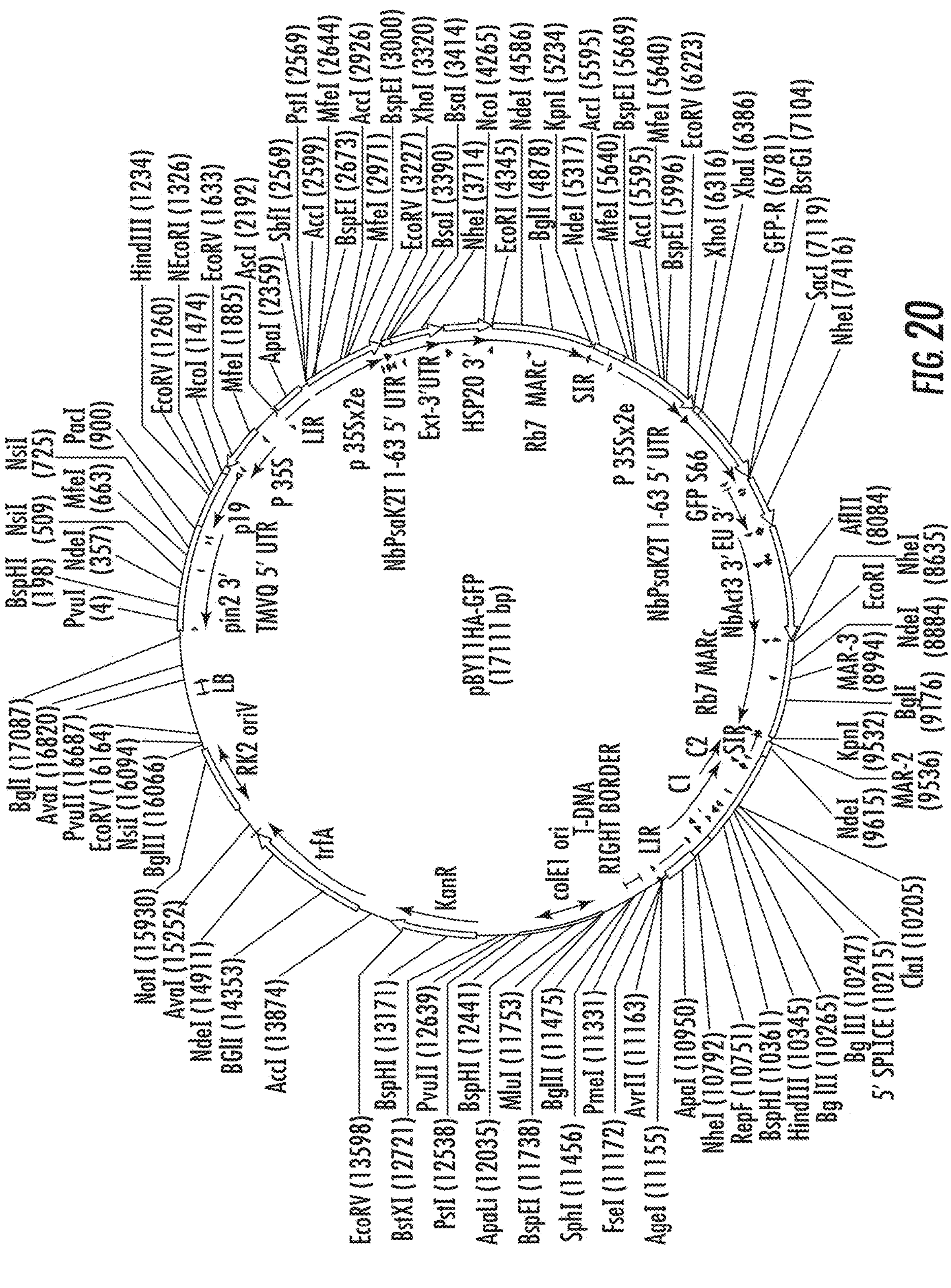
Figure 21:
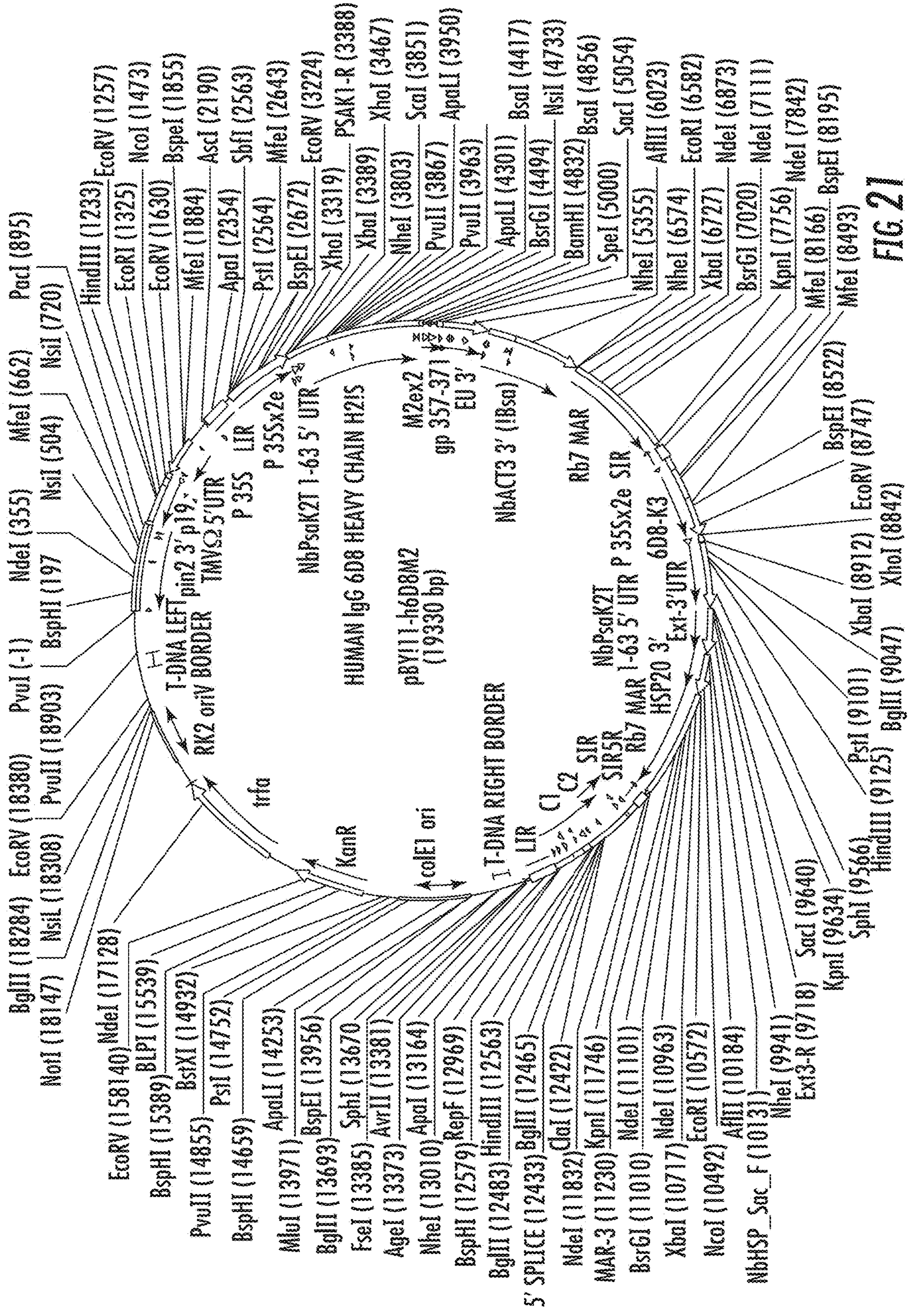
Figure 22A:
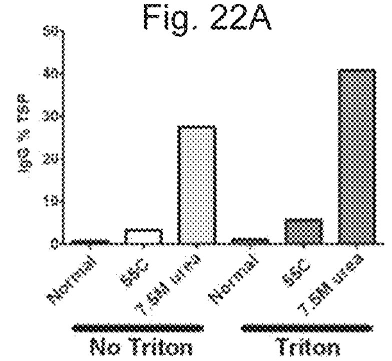
FIGS. 22A-22C depicts expression results of the plasmids of FIGS. 19-21.
Figure 22C:
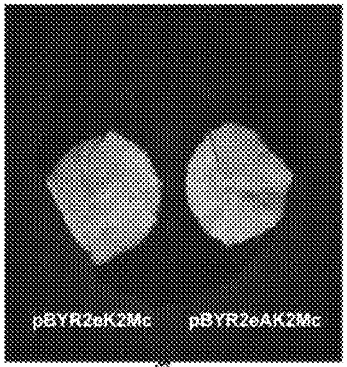
Figure 22B:
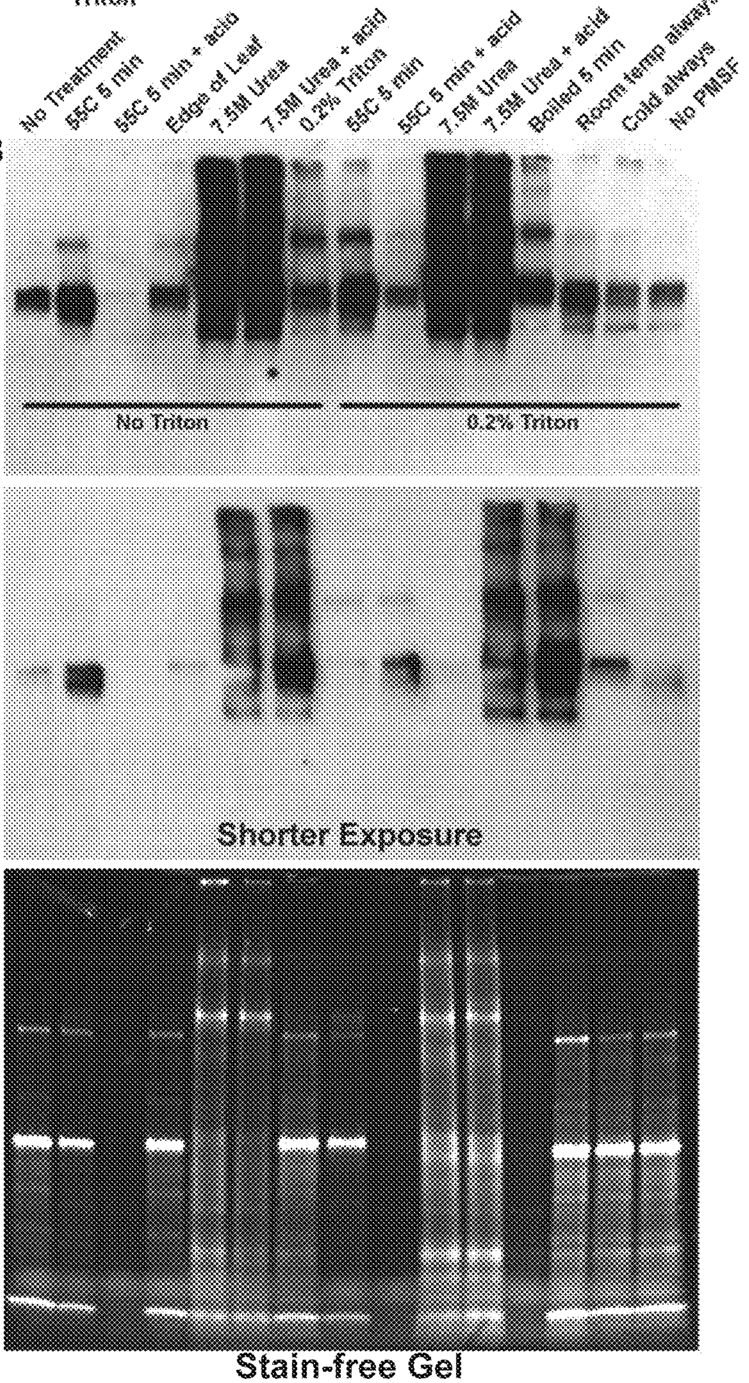

Using the BeYDV plant expression system, we have produced norovirus VLPs at 2-3 times the highest levels reported in plant-based systems. Modified BeYDV vectors allowed high-level production of GII.4 norovirus VLPs without eliciting the plant cell death response. By optimizing extraction conditions, we have achieved >90% purity of VLPs with no losses in yield, allowing production of milligram quantities of VLPs from a single plant leaf 4. Exemplary Plant Expression Vectors pBYR2eAK2Mc-GP (See FIG. 19 and SEQ ID NO. 115) is a BeYDV replicon that lies between the 2 long intergenic regions (indicated as LIR in FIG. 20), bounded by AscI and AgeI sites. The replicon contains one expression cassette with the CaMV 35S dual-enhancer promoter (indicated as P 35Sx2e in FIG. 19) followed by the *N. benthamiana* PsaK2 gene 5' UTR. The expression cassette follows in tandem P 35Sx2e and PsaK2 5' UTR followed by the GFP coding sequence, which is flanked by unique Xbal and SacI sites. Just downstream lie a chimeric terminator (also referred to herein as a double terminator) comprises the intronless tobacco extensin terminator (indicated as EU 3' in FIG. 19) and *N. benthamiana* actin 3 terminator (NbAct3). The double terminator is followed by the tobacco Rb7 matrix attachment region (indicated as Rb7 MARc delta 144-437 in FIG. 19). Downstream of the Rb7 MARc lies the BeYDV short intergenic region (SIR), which also contains polyadenylation signals. The Rep/RepA (C1/C2) gene in the inverse orientation is driven by a BeYDV promoter in the downstream LIR. The expression cassette for the siRNA binding protein p19 (from tomato bushy stunt virus) is located between the Pvul and AscI sites (~0-45° on FIG. 19). The p19 coding sequence is driven by a single enhancer 35S promoter and the tobacco mosaic virus (TMVΩ) 5' UTR. The potato pinII gene 3' region (Pin2) serves as the terminator for the p19 expression cassette. The T-DNA region (DNA that is transferred into plant cells by *A. tumefaciens*) is delineated by the left border and right border segments. As shown in FIG. 22C, this construct with a double terminator downstream of the GFP coding sequence resulted in brighter fluorescence than a corresponding construct with a single terminator (pBYR2eK2Mc-GFP).

pBY11HA-GFP (see FIG. 20 and SEQ ID NO. 116) contains a BeYDV replicon that lies between the 2 long intergenic regions (indicated as LIR in FIG. 20), bounded by AscI and AgeI sites. The replicon contains two expression cassettes having the CaMV 35S dual-enhancer promoter (indicated as P 35Sx2e in FIG. 20) followed by the *N. benthamiana* PsaK2 gene 5' UTR. The first cassette has 2 Bsal sites downstream of the 5' UTR; when cleaved by Bsal, the vector ends have 5' single strand protrusions (cohesive ends) 5'-CTAG (upstream) and 5'-AGCT (downstream), that permit insertion of a coding sequence. The Bsal sites are followed by a chimeric terminator comprising the intronless tobacco extensin terminator (indicated as Ext 3' UTR in FIG. 20) and *N. benthamiana* HSP20 gene terminator (also referred to herein as *N. benthamiana* 18.8 kDa class II heat shock protein 3' UTR or NbHSP), which is followed by the tobacco Rb7 matrix attachment region (indicated as Rb7 MARc in FIG. 20). Downstream of the first Rb7 MARc lies the BeYDV short intergenic region (SIR), which also contains polyadenylation signals. The second expression cassette follows in tandem (P 35Sx2e, PsaK2 5' UTR), followed by the GFP coding sequence, which is flanked by unique Xbal and SacI sites. Just downstream lie a chimeric terminator comprising the intronless tobacco extensin terminator (indicated as EU 3' in FIG. 20) and *N. benthamiana* actin 3 terminator (NbAct3). Another MARc and SIR segment follow the terminators. The Rep/RepA (C1/C2) gene in the inverse orientation is driven by a BeYDV promoter in the downstream LIR. An expression cassette for the siRNA binding protein p19 (from tomato bushy stunt virus) is located between the Pvul and AscI sites (~0-45° on FIG. 20). The p19 coding sequence is driven by a single enhancer 35S promoter and the tobacco mosaic virus (TMVΩ) 5' UTR. The potato pinII gene 3' region (Pin2) serves as the terminator for the p19 expression cassette. The T-DNA region (DNA that is transferred into plant cells by *A. tumefaciens*) is delineated by the left border and right border segments. The pBY11HA-GFP vector is optimized for the co-expression of two proteins and has unique restriction sites for ease of inserting two coding sequences.

pBY!11-h6D8M2e (see FIG. 21 and SEQ ID NO. 117) is similar to the dual-cassette vector pBY11HA-GFP, but has expression cassettes for a modified mAb (heavy chain fused to influenza antigen M2e in first cassette; light chain in second cassette). FIGS. 22A and 22B depict expression data for this vector, namely the expression of a recombinant immune complex (RIC). RIC is inherently insoluble due to the immune complex, but by modifying the extract protocol, RIC can be at least 40% of total soluble protein extracted from the transformed plant. Thus, the dual expression cassette vector containing dual chimeric terminators on both cassettes performs very well.

5. Experimental Procedures a. Vector Construction

For the sequence positions for the Ext terminator, the position of the U of the Ext stop codon is designated as −3. The initial construct was pBY027-IEU for the experiments resulting in FIGS. 1A-9, which contain a fragment spanning 1-731 nt from a *Nicotiana tabacum* genomic DNA (GenBank accession D13951) cloned in pBY027 (Mor et al 2003) using the SacI and EcoRI sites. The fragment was amplified by PCR using primers Ext-1 and Ext-2. The sequences of all primers used in experiments resulting in FIGS. 1A-9 are listed in Table 1. The intron-less form of Ext terminator (spanning 252-731 nt) was amplified by PCR from pBY027-IEU using primers Ext-3 and Ext-2 and cloned into the SacI and EcoRI sites of pBY027 to produce pBY027-EU. A XhoI-EcoRI fragment of pBY027-EU was excised and replaced the corresponding fragment in pPS1 (Huang and Mason 2004) to generate pEU (FIG. 1). The various forms of Ext terminator were similarly cloned using primer pairs of Ext-1 and Ext-2 (pIEU), Ext-3 and Ext-4 (pEU1), Ext-3 and Ext-6 (pEU2), Ext-5 and Ext-2 (pEU3), and Ext-1 and Ext-6 (pIEU2). The control plasmids pNOS, p35S, and pVSP were generated as follows. The NOS terminator was excised from construct pIBT211.1 (Richter et al 2000) and cloned into pBY027 to yield pBY027-NOS using the SacllEcoRl sites. The 35S terminator was amplified by PCR from pRTL2-GUS (Carrington et al 1991) using the primers 35STm-1 and 35STm-2 and cloned into pBY027 opened with SacllEcoRl to give pBY027-35S. The XhoI-EcoRI fragments of pBY027-NOS, pBY027-35S, and pBY027 (contains VSP terminator) were excised and replaced the corresponding fragment in pPS1 to produce pNOS, p35S, and pVSP. A fragment that contains the intron of Ext terminator was amplified by PCR from pIEU using primers Ext-1 and Ext-8 and cloned into pNOS opened with SacI to give pINOS. A set of constructs encoding Norwalk virus capsid protein (NVCP) with various terminators was obtained by replacing the XhoI/SacI fragment containing the green fluorescent protein (GFP) gene from the constructs pEU, pEU1, pEU2, pEU3, pIEU, pIEU2, p35S, pVSP, pNOS, and pINOS with the NVCP coding region excised from the plasmid pSNV210 (Zhang et al 2006) with the XhoI and SacI sites. Another set of constructs containing the β-glucuronidase gene (with intron) was obtained by replacing the GFP gene of constructs pEU, p35S, pVSP, and pNOS with the PCR fragment amplified from pGPTVK-GI (Collens et al 2007) using primers GUS-1 and GUS-2 and digested with XhoI and SacI.

For experiments resulting in FIGS. 10A-17B, an *agrobacterium* T-DNA binary vector containing the 35S promoter, tobacco mosaic virus 5' UTR, GFP gene, and full-length tobacco extensin terminator was constructed by 3-fragment ligation: the vector backbone from pPS1 (Huang and Mason, 2004) was obtained by XhoI-EcoRI digestion; the TMV 5' UTR-GFP fragment was excised from pBYR2e-GFP (Diamos et al., 2016) by XhoI-SacI digestion; and the intronless extensin terminator was excised from pBY-GFP212 (Diamos et al., 2016). The resulting vector, pPS-OGFP-EU, was used to construct single and double terminator constructs. The DsRed gene was amplified from pBYDsRed (Huang et al., 2010) with primers DsR-Xba-F and VspHT, digested Xbal-SacI, and inserted into pPS-OGFP-EU to create pPS-ODsR-EU. Terminators were amplified by PCR using primers (Table 1) designed to insert SacI and EcoRI restriction sites at its 5' and 3' ends, respectively, digested SacI-EcoRI, and ligated into pPS-OGFP digested likewise. The pinII, NOS, and rbcS 3' regions were obtained from pHB114 (Richter et al., 2000), pHB103 (Richter et al., 2000), and pRTL2-GUS (Carrington et al. 1991) respectively by SacI-EcoRI digestion and cloned into pPS-OGFP digested likewise.

Specifically, The NbHSP (homolog of At5g12020) and NbACT3 (homolog of At5g09810) terminators were identified using the Sol Genomics Network *N. benthamiana* draft genome (Fernandez-Pozo et al., 2015). Primers (Table 1) specific for NbHSP and NbACT3 designed to introduce SacI and EcoRI sites were used to amplify the downstream segments of each gene from *N. benthamiana* genomic DNA. The PCR products were digested SacI-EcoRI and inserted into pPS-OGFP-EU digested likewise.

For double terminator constructs, the upstream segment was amplified by PCR using primers (Table S1) designed to insert a SacI site at the 5' end, and Bsal site at the 3' end. The downstream segment was amplified with a Bsal site at the 5' end designed to generate compatible overhang with the upstream Bsal site, and an EcoRI site at the 3' end. The final construct was assembled by 3-fragment ligation: pPS-OGFP-EU digested SacI-EcoRI, the upstream segment digested SacI-Bsal, and the downstream segment digested Bsal-EcoRI.

For MAR constructs, the tobacco Rb7 or TM6 MAR was inserted downstream from the terminator. First, the Rb7 MAR was inserted into pPS-OGFP-EU by three fragment ligation: pPS-OGFP-EU was digested Pvul-Sphl to obtain the vector fragment; pPS-OGFP-EU was digested Pvul-EcoRI to obtain the GFP cassette; and pBYR2e-MRtxGM (Diamos et al., 2016) was digested EcoRI-Sphl to obtain the Rb7 MAR fragment. The resulting vector was digested KpnI-AgeI, the ends were blunted with Klenow fragment DNA polymerase, and the vector fragment was self-ligated to yield pPS-OGFPM-EU. The TM6 MAR (genbank accession KC555564) was PCR amplified from tobacco genomic DNA using primers TM6-EcoRI-F and TM6-KpnI-R (Ji et al., 2013), digested EcoRI-KpnI, and inserted into pUC19. The EcoRI-AvrII fragment containing the TM6 MAR was then excised and inserted into pPS-OGFPM-EU digested likewise to yield pPS-OGFPT-EU. Single or double terminators were inserted into pPS-OGFPM-EU or pPS-OGFPT-EU by SacI-EcoRI digestion as described for pPS-OGFP-EU. For Rb7 deletion mutants, native restriction sites were used as shown in FIGS. 14A and 14B. After digestion with each respective enzyme, the ends were blunted with Klenow fragment DNA polymerase, and self-ligated.

TABLE 1

| Primers Used | | |
|---|---|---|
| Name/Seq ID No. | | Sequence (5' to 3') |
| CAA-2 | 22 | GTTGTTGTTGTTGTTGTTTTGTGATGTTTGAACGATCGGGG |
| CAA-3 | 23 | CAACAACAACAACAACAAAACATTGGCAATAAAGTTTCTTAAGATTG |
| CAA-4 | 24 | TGTTTTGTTGTTGTTGTTGTTGTTGTTGTTGTTGTTGTTTTGTG |
| CAA-5 | 25 | CACAAAACAACAACAACAACAACAACAACAACAACAACAAAACA |
| 35STm-1 | 26 | GTGAGCTCGTCCGCAAAAATCACCAG |
| 35STm-2 | 27 | CAGAATTCGTCACTGGATTTTGGTTTTAGG |
| DT-2 | 28 | CGCTGTGCTGCCGTGCCTTTTTTTTTTTTTTTTTT |
| DT-4 | 29 | CGCTGTGCTGCCGTGCCTT |
| Ed-2 | 30 | GGCTTTATTATTTAATTGTCTCTCGAAAATGG |
| Ed-3 | 31 | TCGAGAGACAATTAAATAATAAAGCCCCACAG |
| EFf | 32 | CTGGTGGTTTTGAAGCTGGTA |
| EFp | 33 | FAM-CACGCATTGCTTGCTTTCACCC-TAMRA |
| EFr | 34 | GGTGGTAGCATCCATCTTGTT |
| Et-2 | 35 | ATCATCATCATCATCAATTCACATTGTCTCTCGAAAATGGAAAAAG |
| Et-3 | 36 | GATGATGATGATGATGAATTGTGTAAATAATAAAGCCCCACAGG |
| Ext-1 | 37 | GTGAGCTCGAAGTGACATCACAAAGTTGAAG |
| Ext-2 | 38 | CAGAATTCGTCATAACTGTAGAAATGATTCC |
| Ext-3 | 39 | GTGAGCTCAAAGCAGAATGCTGAGCTA |
| Ext-4 | 40 | CAGAATTCGGCTAGCTAGAGAGAGGAGGAGAAT |
| Ext-6 | 41 | CAGAATTCGAAACTGAACAAAACATACACAATGACAG |
| Ext-8 | 42 | TGCGAGCTCCTGCATAAGAATATACATTGTGTG |
| gfp-3f | 43 | ATGGTCCTGCTGGAGTTCGTGACC |
| gfp-f | 44 | GTCCAGGAGCGCACCATCTTCT |
| gfp-p | 45 | FAM-CGGGTCTTGTAGTTGCCGTCGTCCTTG-TAMRA |
| gfp-r | 46 | GATGCCCTTCAGCTCGATGCGGTT |
| GFP-F1 | 47 | GTCCTGCTGGAGTTCGTGACC |
| GFP-F2 | 48 | GCATGGACGAGCTGTACAAGTAAGAGC |
| GFP-R1 | 49 | CGTTTACGTCGCCGTCCAGC |
| GFP-R2 | 50 | CTCGCCCTTGCTCACCATTGTTC |
| GUS-1 | 51 | GTCTCGAGAACAATGTTACGTCCTGTAGAAACC |
| GUS-2 | 52 | ACGAGCTCTCATTGTTTGCCTCCCTGC |
| NE-2 | 53 | TTCTTCTTCTTCTTCTTTTCTCATGTTTGAACGATCGGGG |
| NE-3 | 54 | GAAGAAGAAGAAGAAGAAAAGATTGGCAATAAAGTTTCTTAAGATTG |
| NE-4 | 55 | TTCTTCTTCTTCTTCTTTTCTCAGGATTCAATCTTAAGAAAC |
| NE-5 | 56 | GAAGAAGAAGAAGAAGAAAAGAGGTTGCCGGTCTTGCGATG |
| NET-2 | 57 | ATCATCATCATCATCAATTCACATGTTTGAACGATCGGGG |
| NET-3 | 58 | GATGATGATGATGATGAATTGTTTGGCAATAAAGTTTCTTAAGATTG |
| NOSREco | 59 | CTCGAATTCCCGATCTAGTAAC |

TABLE 1-continued

Primers Used

| Name/Seq ID No. | | Sequence (5' to 3') |
|---|---|---|
| RS-2 | 60 | CAGCCCTACAACTATATCCGATGATGTTTGAACGATCGGGG |
| RS-3 | 61 | GAGTAAATATTACGAGTCGAGGTTGGCAATAAAGTTTCTTAAGATTG |
| RS-4 | 62 | CCTCGACTCGTAATATTTACTCAGCCCTACAACTATATCCGATG |
| RS-5 | 63 | CATCGGATATAGTTGTAGGGCTGAGTAAATATTACGAGTCGAGG |
| RT-0 | 64 | AACGAT TGAAGGAGCCACTCA |
| RT-1 | 65 | ACTGAAGGCGGGAAACGAC |
| RT-2 | 66 | GTGGTTGGCATGCACATACAA |
| RT-3 | 67 | ATTTGCCTGCGCACCTGT |
| sNV-3f | 68 | AATGGTGCTAGCAGCGGTCCAC |
| sNV-f | 69 | CAATGTCCAAAGTGTGCAATTCC |
| sNV-p | 70 | FAM-TGATGGAAGACTTGTTGGCACC-TAMRA |
| sNV-r | 71 | CCTCTTATCTTGGCAACATGTGAC |
| VE-5 | 72 | GAGAAAAGAAGAAGAAGAAGAAGAAGAAGAAGAAGAAAAGA |
| VE-6 | 73 | TCTTTTCTTCTTCTTCTTCTTCTTCTTCTTCTTCTTCTTTTCTC |
| Vet-5 | 74 | GTGAATTGATGATGATGATGATGATGATGATGATGATGAATTGT |
| Vet-6 | 75 | ACAATTCATCATCATCATCATCATCATCATCATCATCAATTCAC |
| TM6-EcoRI-F | 76 | TCCGAATTCTAATATTTAGAAATTTAATTAACATAACCAAGG |
| TM6-KpnI-R | 77 | CTGGTACCGACATCCTAGGTTCAATCAAAT |
| DsR-Xba-F | 78 | GAGTCTAGAACATGGTGCGCTCCTCC |
| VspHT | 79 | TGAATAGTGCATATCAGCATACCTTA |
| EU-Bsa-F | 80 | AGGGTCTCGGCTCAAAGCAGAATGCTG |
| EU-Bsa-R | 81 | AAGGTCTCGGAGCGTCATAACTGTAGAAATGATTCC |
| BDB-Bsa-F | 82 | GGGTCTCGGCTCTGACAACATCAGCAAG |
| NbHSP-Bsa-F | 83 | AGGGTCTCGGCTCACTGAGGAAATATATAGACAAATTAAG |
| 35S-Bsa-R | 84 | AAGGTCTCGGAGCGTCACTGGATTTTGGTTTTAGG |
| NbHSP-Bsa-R | 85 | AAGGTCTCAGAGCTCCCAAAGGAAACTATGTGTAC |
| NOS-Bsa-R | 86 | AGGGTCTCGGCTCAGATCGTTCAAACATTTG |
| Pin2-Bsa-F | 87 | GAGGTCTCAGCTCGTACCCTGCAATGTGACC |
| NbACT-Bsa-F | 88 | AGGGTCTCGGCTCATACAGCATTCCCA |
| BDB501-Sac-F | 89 | CCGAGCTCTGACAACATCAGCAAGAACG |
| BDB501-Eco-R | 90 | AAGAATTCAAAGGAAACCCATAAGATGCG |
| NbHSP-Sac-F | 91 | TCGAGCTCACTGAGGAAATATATAGACAAATTAAGTTTGGTTCTATG |
| NbHSP-Eco-R | 92 | GTGAATTCGCTCCCAAAGGAAACTATGTGTACTTC |

TABLE 1-continued

| Primers Used | | |
|---|---|---|
| Name/Seq ID No. | | Sequence (5' to 3') |
| NbACT-Sac-F | 93 | GCGAGCTCATACAGCATTCCCAGAAAGAGAAAC |
| NbACT-Eco-R | 94 | TAGAATTCATGCTAGCTTGTTTACACCTCG |
| BDA375-Sac-F | 95 | GAGAGCTCGGAGAACGCCTTATTATTGTATATGGC |
| BDA375-Eco-R | 96 | AAGAATTCGCTCATCACTGCACTTCAAGC |
| AtHSP-Sac-F | 97 | TAGAGCTCATATGAAGATGAAGATGAAATATTTGGTGTG |
| AtHSP-Eco-R | 98 | ATGAATTCCTTATCTTTAATCATATTCCATAGTCCATACC |
| AtHSP-Bsa-R | 99 | AAGGTCTCGGAGCCTTATCTTTAATCATATTCCATAGTCCATACC |
| Rep-Sac-F | 100 | AGCGAGCTCTAATAGGTTGCCAGTCTGATTTC |
| Rep-Eco-R | 101 | CTAGAATTCTTGCCATCGTTTTGTGG |
| RepA-Sac-F | 102 | TCGGAGCTCTGAACGTGCCTCTCCTC |
| SIR-Sac-F | 103 | AAGGAGCTCTAAAATGATTATTTTATGAATATATTTCATTGTGC |
| NbACT617-EcoR | 104 | AATGAATTCGAACCCCAATTACTGGAGC |
| 35S-Bsa-F | 105 | GCGGTCTCGGCATGGTGGAGCACGA |
| NOS-Bsa-F | 106 | AGGGTCTCGGCTCAGATCGTTCAAACATTTG |
| TNVD3-Bsr-F | 107 | ATTGTACAAGTAATTGCTTTCATAGATCCGTCTTCC |
| TNVD3-Sac-R | 108 | TAGAGCTCGGGTTCCTAGAGAGATCTCTAGG |
| TMV3-Bsr-F | 109 | TATGTACAAGTAAGGTAGTCAAGATGCATAATAAATAACGGATTGTG |
| TMV3-Sac-R | 110 | TAGAGCTCTGGGCCCCTACCGGGGGTAA |
| PEMV3-Bsr-F | 111 | ATTGTACAAGTAAGGCTTCGCTTCCCGCC |
| BYDV3-Kpn-F | 112 | AAGGTACCAGTGAAGACAACACC |
| BYDV3-Sac-R | 113 | ATGAGCTCGGGTTGCCGAACTGC |

b. DNA Constructs for Polypurine Sequence (PPS) Mutants

PPS mutant vectors were constructed using standard overlapping PCR and molecular cloning methods. For pEUd, primer sets Ext-3/Ed-2 and Ed-3/Ext-6 were used for initial amplification in separate PCR reactions using pBY027.IEU as template. The resulting PCR fragments were mixed and amplified using primers Ext-3 and Ext-6, complementary to the ends of the two initial fragments. The resulting PCR product was inserted into pBY027 using SacI/EcoRI sites and then subcloned into pPS1 via XhoI/EcoRI. For pEUs, similar steps were performed to amplify two overlapping DNA fragments in separate PCRs. The 5' fragment was obtained by double round PCR: in the first round, primers Ext-1 and Et-2 were used with pBY027.IEF as template and the resulting fragment was used for a second round of amplification with primers Ext-1 and Vet-6. The 3' fragment was also obtained by double round PCR: in the first round, primers Et-3 and Ext-2 were used with pBY027.EF as template and the resulting fragment was used for a second round of amplification with primers Vet-5 and Ext-2. The resulting 5' and 3' fragments were mixed and amplified using primers Ext-3 and Ext-2. The final PCR product was inserted into pBY027 using SacI/EcoRI sites and then subcloned via XhoI/EcoRI into pPS1.

c. Agroinfiltration Procedure

Binary vectors were separately introduced into *Agrobacterium tumefaciens* LBA4404 (for FIGS. 1A-9) or GV3101 (for FIGS. 10A-17B) by electroporation. The resulting strains were verified by PCR, grown overnight at 30° C., and used to infiltrate leaves. For the experiments of FIGS. 1A-9, the leaves were from 6- to 8-week-old growth chamber-grown *N. benthamiana*, tobacco (*N. tabacum* cv. 81V9), or lettuce (*Lactuca sativa* cv. Lolla Rosa) plants. For the experiments of FIGS. 10A-17B, the leaves were from 5- to 6-week-old *Nicotiana benthamiana*, tobacco (*N. tabacum*), or lettuce (*Lactuca sativa* "Black Seeded Simpson") maintained at 23-25° C. Briefly, the bacteria were pelleted by centrifugation for 5 min at 5,000 g and then resuspended in infiltration buffer (10 mM 2-(N-morpholino)ethanesulfonic acid (MES), pH 5.5 and 10 mM $MgSO_4$) to OD600=0.2. The resulting bacterial suspensions were infiltrated using a syringe without needle into fully expanded leaves through a small puncture (Huang and Mason 2004). Plant tissue was harvested 5 days post infiltration (DPI). Leaves producing GFP were photographed under UV illumination generated by a B-100AP lamp (UVP, Upland, CA).

d. GFP Assay

Total protein was extracted from leaf samples harvested at 2-3 DPI with extraction buffer (25 mM sodium phosphate buffer, pH 6.6, 100 mM NaCl, 1 mM EDTA, 0.05% Triton X-100, 50 mM sodium ascorbate, and 10 μg/ml leupeptin) using a FastPrep machine (Bio101). Cleared supernatants were obtained by centrifugation at 13,000 g for 10 min. The protein concentration from the leaf samples was determined using Bradford reagent (Bio-Rad®) with bovine serum albumin (BSA) as the reference standard. The GFP fluorescence intensity was examined on a microplate reader (Molecular Device Co, Spectra Max M2). GFP samples were prepared by serial 2-fold dilution with phosphate buffered saline (PBS, 137 mM NaCl, 2.6 mM KCl, 10 mM Na2HPO4, and 1.8 mM KH2PO4, pH 7.4) and 50 μl of each sample was added to black-wall 96-well plates (Corning), in duplicate. The excitation and emission wavelengths were 485 nm and 538 nm, respectively. All measurements were performed at room temperature and the reading of negative control (extract of uninfiltrated plant leaf) was subtracted before graphing. *E. coli* expressed GFP was used to generate standard curve. His-tagged GFP gene was cloned into pET28 expression vector (Invitrogen), introduced into *E. coli* strain BL21(DE3), and IPTG-induced GFP was purified using TALON His-Tag purification resin (Clontech®). GFP production was also analyzed by SDS-PAGE. Briefly, clarified plant protein extracts from 3 DPI were mixed with sample buffer (50 mM Tris-HCl, pH 6.8, 2% SDS, 10% glycerol, 0.02% bromophenol blue) and separated on 4-15% polyacrylamide gels (Bio-Rad®). The GFP band was visualized under UV illumination (365 nm), and the band intensity was quantified using ImageJ software.

e. Nvcp ELISA

Total leaf protein extracts prepared and normalized as described above were assayed by NVCP sandwich ELISA (Mason et al 1996). Briefly, a rabbit polyclonal anti-NVCP and a guinea pig polyclonal anti-NVCP were used as capture and detection antibodies, respectively. Insect cell-derived recombinant NVCP (Jiang et al 1992) was used as the reference standard.

f. GUS Activity Assay

GUS activity was measured as described by Francis and Spiker (2005). Briefly, total leaf protein was extracted from 100 mg leaf tissue at 2 DPI with 1 ml GUS Extraction Buffer [150 mM sodium phosphate pH 7.0, 10 mM EDTA, 10 mM β-mercaptoethanol, 0.1% Triton X-100, 0.1% sarcosyl, 10 μg/ml leupeptin] using a FastPrep machine (Bio101). The cleared extract (10 μl) was incubated with 130 μl assay buffer [GUS Extraction Buffer containing 1.2 mM 4-methylumbelliferyl-β-D-glucuronide (MUG) (Sigma(R))] in a dark 37° C. incubator for 20 minutes. The reaction was stopped by transferring 10 μl of the reaction to 190 μl stop buffer [200 mM sodium carbonate] in a black wall 96-well plate. Fluorescence was measured on a SpectraMax M2 microplate reader (Molecular Devices) at 460 nm when excited at 355 nm. A standard curve was generated using 50, 25, 5, 2.5, 0.5, 0.25, and 0 μM 4-methylumbelliferone (MU) on every plate. Fluorescence values were converted to moles of MU/minute, and then standardized by protein concentration determined by Bio-Rad RC DC protein assay kit according to the kit instructions, using BSA as the reference standard.

g. RNA Extraction and Quantitative PCR

Total RNA was purified from infiltrated tobacco leaves at 2 DPI using Plant RNA Reagent (Invitrogen), and residual DNA was removed by DNAfree system (Ambion). First-strand cDNA was synthesized from 1 μg of total RNA and oligo dT22 primer using the Superscript III First-Strand Synthesis System (Invitrogen) according to the manufacturer's protocol. Real-time PCR for each transcript of interest was performed on an IQ5 Real-Time PCR Detection System (Bio-Rad) using gene specific primers (gfp-f and gfp-r for GFP; sNV-f and sNV-r for NVCP) and custom-made Taqman FAM/MGB probes (GFP-p and sNV-p, Integrated DNA Technologies). Each sample was measured in triplicate for each transcript of interest and an internal reference gene. Elongation factor (EF1a) transcripts served as internal control (using primers EFf and EFr and probe EFp, Integrated DNA Technologies). Transcript levels of GFP, NVCP and EF1a were quantified using separate standard curves prepared with plasmids pBY027, pSNV210, and pCR4-Topo-EF1a, respectively. The construct pCR4-Topo-EF1a was obtained as follows. RT-PCR was performed with cDNA from wild-type *N. benthamiana* RNA using EF1f and EF1r primers, which amplify 119 bp (nt 167-285) fragment of EF1a gene (accession number AY206004). The amplified product was cloned into a PCR cloning vector, pCR4-Topo (Invitrogen). The relative quantification of GFP and NVCP transcripts was normalized against EFla transcripts.

h. Sequence Alignment of Ext Genes

The nucleotide sequences of plant Ext gene terminators were obtained from GenBank. The *N. benthamiana* Ext nucleotide sequence was obtained from the Sol Genomics Network (Bombarely et al 2012). Alignment was performed using the online program Clustal Omega.

i. Read-Through PCR

First-strand cDNA was synthesized from 1 μg of total RNA, described above, with a random primer. PCRs were performed to evaluate the transcription read-through of GFP and NVCP transcripts with four sets of primers. For GFP transcripts, a forward primer (gfp-3f), specific to GFP gene, was paired with one of four reverse primers RT-0, RT-1, RT-2, and RT-3, positioned at 42, 156, 291, and 389, respectively, downstream of the EcoRI site on the expression vectors. For NVCP transcripts, a NVCP specific sense primer sNV-3f was paired with the same four antisense primers used for GFP transcripts test.

j. Analysis of Transcript 3' Ends by Circularized RT-PCR

Circularized RT-PCR was performed as described, with modification (Slomovic and Schuster 2013). Total RNA was purified from leaves of *N. benthamiana* at 4 days post infiltration using RNeasy Plant Mini Kit (Qiagen®). Prior to circularization, 5 μg total RNA was decapped with 25 U of RNA 5' pyrophosphohydrolase (NEB) and 40 U of RNAse-OUT RNA inhibitor (Invitrogen) in a total volume of 50 μl buffer (20 mM Tris-HCl, pH 8.8, 10 mM $(NH_4)_2SO_4$, 10 mM KCl, 2 mM $MgSO_4$, 0.1% Triton X-100) for 1 hour at 37° C. The reaction was stopped by addition of 1 μl of 500 mM EDTA, and heated to 65° C. for 5 minutes. Decapped RNA was purified using a spin column (Qiagen®). RNA was then circularized with 10 U of T4 RNA Ligase (NEB) and 40 U RNAseOUT in a total volume of 20 μl buffer (50 mM Tris-HCl, pH 7.5, 10 mM $MgCl_2$, 1 mM DTT, 10% PEG8000, 50 μM ATP) for 1.5 hours at 25° C. The reaction was terminated by boiling for 2 minutes. First-strand cDNA was synthesized using Superscript III First-Strand Synthesis System (Invitrogen®) according to the manufacturer's protocol from purified circularized RNA using the primer GFP-R1, which binds near the 5' end of the GFP mRNA in the reverse direction. PCRs were performed by standard procedures with the cDNA obtained. Divergent primers were used for amplification of the fused 3' and 5' ends of the GFP mRNA: the forward primer, GFP-F1, which binds the 3' end of the GFP gene, and the reverse primer GFP-R2, which binds to the 5' end of the GFP gene, were designed to specifically amplify a cDNA product derived from a circularized transcript. A second round of PCR using primers GFP-R2 and GFP-F2 to increase specificity was also performed as suggested (Slomovic and Schuster 2013). The PCR products were cloned using native SacI-XhoI sites present in the mRNA, and 14 positive clones were randomly selected and sequenced.

k. Protein Extraction and Fluorescence Analysis

Total protein extract was obtained by homogenizing agroinfiltrated leaf samples with 1:5 (w:v) ice cold extraction buffer (25 mM sodium phosphate, pH 7.4, 100 mM NaCl, 1 mM EDTA, 0.1% Triton X-100, 10 mg/mL sodium ascorbate, 0.3 mg/mL PMSF) using a Bullet Blender machine (Next Advance, Averill Park, NY) following the manufacturer's instruction. To enhance solubility, the homogenized samples were end-over-end mixed at room temperature or 4° C. for 30 min. The crude plant extract was clarified by centrifugation at 13,000 g for 10 min at 4° C. Protein concentration of clarified leaf extracts was measured using a Bradford protein assay kit (Bio-Rad®) with bovine serum albumin as standard. For SDS-PAGE, clarified plant proteins extract were mixed with sample buffer containing a final concentration of 50 mM Tris-HCl, pH 6.8, 2% SDS, 10% glycerol, 0.02% bromophenol blue, and separated on 4-15% polyacrylamide gels (Bio-Rad®). For GFP or DsRed fluorescence, PAGE gels were visualized under UV illumination (365 nm) and stained with Coomassie stain (Bio-Rad®) following the manufacturer's instructions. The fluorescent band corresponding to GFP or DsRed was analyzed using ImageJ software to quantify the band intensity using native plant protein bands as an internal loading control.

l. SDS-PAGE and Western Blot

Clarified plant protein extract was mixed with sample buffer (50 mM Tris-HCl, pH 6.8, 2% SDS, 10% glycerol, 0.5M DTT, 0.02% bromophenol blue), boiled for 10 min, and then separated on 4-15% polyacrylamide gels (Bio-Rad). Polyacrylamide gels were either transferred to a PVDF membrane or stained with Coomassie stain (Bio-Rad) following the manufacturer's instructions. For GII.4 norovirus capsid detection, the protein transferred membranes were blocked with 5% dry milk in PBST (PBS with 0.05% Tween-20) for 1 h at 37° C. and probed in succession with polyclonal rabbit-anti GII.4 [44] diluted 1:5000 in 1% PBSTM followed by goat anti-rabbit IgG antibody-horseradish peroxidase conjugate (Sigma) diluted 1:5000 in 1% PBSTM. Bound antibody was detected with ECL reagent (Amersham).

m. Protein Quantification by ELISA

Norovirus capsid production was analyzed by sandwich ELISA. A rabbit polyclonal anti-GI or anti-GII antibody was bound to 96-well high-binding polystyrene plates (Corning), and the plates were blocked with 5% nonfat dry milk in PBST. After washing the wells with PBST (PBS with 0.05% Tween 20), the plant extracts were added and incubated. The bound norovirus capsids were detected by incubation with guinea pig polyclonal anti-GI or anti-GII antibody followed by goat anti-guinea pig IgG antibody-horseradish peroxidase conjugate (Sigma). The plate was developed with TMB substrate (Pierce) and the absorbance was read at 450 nm. Plant-produced GI or GII capsids were used as the reference standard (Kentucky Bio Processing).

REFERENCES CITED

Ali S, Taylor WC (2001) The 3' non-coding region of a C4 photosynthesis gene increases transgene expression when combined with heterologous promoters Plant Mol Biol 46:325-333

Allen, E., and Howell, M. D. (2010). miRNAs in the biogenesis of trans-acting siRNAs in higher plants. Semin. Cell Dev. Biol. 21, 798-804. doi:10.1016/j.semcdb.2010.03.008.

Allen, G. C., Hall, G., Michalowski, S., Newman, W., Spiker, S., Weissinger, A. K., et al. (1996). High-Level Transgene Expression in Plant Cells: Effects of a Strong Scaffold Attachment Region from Tobacco. Plant Cell 8, 899-913. doi:10.1105/tpc.8.5.899.Arntzen C J (2008) Plant science. Using tobacco to treat cancer Science 321:1052-1053 doi:10.1126/science.1163420

Andersen, P. K., Lykke-Andersen, S., and Jensen, T. H. (2012). Promoter-proximal polyadenylation sites reduce transcription activity. Genes Dev. 26, 2169-2179. doi: 10.1101/gad.189126.112.

Baeg K, Iwakawa H, Tomari Y (2017) The poly(A) tail blocks RDR6 from converting self mRNAs into substrates for gene silencing. Nat Plants 3:17036. doi: 10.1038/nplants.2017.36

Béclin, C., Boutet, S., Waterhouse, P., and Vaucheret, H. (2002). A branched pathway for transgene-induced RNA silencing in plants. Curr. Biol. 12, 684-688. doi:10.1016/50960-9822(02)00792-3.

Beyene G, Buenrostro-Nava M T, Damaj M B, Gao S-J, Molina J, Mirkov T E (2010) Unprecedented enhancement of transient gene expression from minimal cassettes using a double terminator Plant Cell Reports 30:13-25 doi:10.1007/s00299-010-0936-3

Bombarely A, Rosli H G, Vrebalov J, Moffett P, Mueller L A, Martin G B (2012) A Draft Genome Sequence of *Nicotiana* benthamianato Enhance Molecular Plant-Microbe Biology Research. Mol Plant-Microbe Interact 25:1523-1530. doi: 10.1094/mpmi-06-12-0148-ta Calikowski, T. T., Meulia, T., and Meier, I. (2003). A proteomic study of the *arabidopsis* nuclear matrix. J. Cell. Biochem. 90, 361-78. doi:10.1002/jcb.10624.

Carrington J C, Freed D D, Leinicke A J (1991) Bipartite Signal Sequence Mediates Nuclear Translocation of the Plant Potyviral NIa Protein The Plant Cell 3:953 doi: 10.2307/3869157

Chen, Q., and Davis, K. R. (2016). The potential of plants as a system for the development and production of human biologics. F1000Research 5, 912. doi:10.12688/f1000research. 8010.1.

Chen, Q., Dent, M., Hurtado, J., Stahnke, J., McNulty, A., Leuzinger, K., et al. (2016). Transient Protein Expression by Agroinfiltration in Lettuce. Methods Mol. Biol. 1385, 55-67. doi:10.1007/978-1-4939-3289-4_4.

Chung B Y W, Simons C, Firth A E, Brown C M, Hellens R P (2006) BMC Genomics 7:120 doi:10.1186/1471-2164-7-120

Collens J I, Mason H S, Curtis W R (2007) *Agrobacterium*-mediated viral vector-amplified transient gene expression in *Nicotiana glutinosa* plant tissue culture Biotechnol Prog 23:570-576 doi:10.1021/bp060342u Collens J I, Mason H S, Curtis W R (2008) *Agrobacterium*-Mediated Viral Vector-Amplified Transient Gene Expression in *Nicotiana glutinosa* Plant Tissue Culture Biotechnology Progress 23:570-576 doi:10.1021/bp060342u D'Aoust, M.-A., Couture, M. M.-J., Charland, N., Trépanier, S., Landry, N., Ors, F., et al. (2010). The production of hemagglutinin-based virus-like particles in plants: a rapid, efficient and safe response to pandemic influenza. Plant Biotechnol. J. 8, 607-19. doi:10.1111/j.1467-7652.2009.00496.x.

Diamos A G, Rosenthal S H, Mason H S (2016) 5' and 3' Untranslated Regions Strongly Enhance Performance of Geminiviral Replicons in *Nicotiana benthamiana* Leaves Frontiers in Plant Science 7 doi:10.3389/fpls.2016.00200

Dong H et al. (2007) An exploration of 3'-end processing signals and their tissue distribution in *Oryza sativa* Gene 389:107-113 doi:10.1016/j.gene.2006.10.015

Fan, Q., Treder, K., and Miller, W. A. (2012). Untranslated regions of diverse plant viral RNAs vary greatly in translation enhancement efficiency. BMC Biotechnol. 12, 22. doi:10.1186/1472-6750-12-22.

Fernandez-Pozo, N., Menda, N., Edwards, J. D., Saha, S., Tecle, I. Y., Strickler, S. R., et al. (2015). The Sol Genomics Network (SGN)—from genotype to phenotype to breeding. Nucleic Acids Res. 43, D1036-41. doi:10.1093/nar/gku1195.

Fox, J. L. (2012). First plant-made biologic approved. Nat. Biotechnol. 30, 472-472. doi:10.1038/nbt0612-472.Francis K E, Spiker S (2004) Identification of *Arabidopsis thaliana* transformants without selection reveals a high occurrence of silenced T-DNA integrations The Plant Journal 41:464-477 doi:10.1111/j.1365-313x.2004.02312.x Gilmartin G M (2005) Eukaryotic mRNA 3' processing: a common means to different ends Genes & Development 19:2517-2521 doi:10.1101/gad.1378105

Gleba Y Y, Tusé D, Giritch A (2014) Plant viral vectors for delivery by *Agrobacterium*. In: Current Topics in Microbiology and Immunology. pp 155-192Gray N K, Hentze M W (1994) Regulation of protein synthesis by mRNA structure Molecular Biology Reports 19:195-200 doi:10.1007/bf00986961

Halweg, C. (2005). The Rb7 Matrix Attachment Region Increases the Likelihood and Magnitude of Transgene Expression in Tobacco Cells: A Flow Cytometric Study. Plant Cell Online 17, 418-429. doi:10.1105/tpc.104.028100.

Hiatt, A., Bohorova, N., Bohorov, O., Goodman, C., Kim, D., Pauly, M. H., et al. (2014). Glycan variants of a respiratory syncytial virus antibody with enhanced effector function and in vivo efficacy. Proc. Natl. Acad. Sci. 111, 5992-5997. doi:10.1073/pnas.1402458111.

Hori K, Watanabe Y (2007) Context analysis of termination codons in mRNA that are recognized by plant NMD. Plant Cell Physiol 48:1072-8. doi:10.1093/pcp/pcm075

Hirsinger C, Parmentier Y, Durr A, Fleck J, Jamet E (1997) Plant Molecular Biology 33:279-289 doi:10.1023/a:1005738815383

Huang Z, Mason H S (2004) Conformational analysis of hepatitis B surface antigen fusions in an *Agrobacterium*-mediated transient expression system Plant Biotechnology Journal 2:241-249 doi:10.1111/j.1467-7652.2004.00068.x Huang, Z., Chen, Q., Hjelm, B., Arntzen, C., and Mason, H. (2009). A DNA replicon system for rapid high-level production of virus-like particles in plants. Biotechnol. Bioeng. 103, 706-714. doi:10.1002/bit.22299.

Huang, Z., Phoolcharoen, W., Lai, H., Piensook, K., Cardineau, G., Zeitlin, L., et al. (2010). High-level rapid production of full-size monoclonal antibodies in plants by a single-vector DNA replicon system. Biotechnol. Bioeng. 106, 9-17. doi:10.1002/bit.22652.

Hunt A G (2008) Messenger RNA 3' end formation in plants. Curr. Top. Microbiol. Immunol. 326:151-177 doi:10.1007/978-3-540-76776-3 9

Ingelbrecht L W, Herman L M F, Dekeyser R A, Montagu M C Van, Depicker A G (1989) Different 3' End Regions Strongly Influence the Level of Gene Expression in Plant Cells. Plant Cell 1:671-680 doi:10.1105/tpc.1.7.671

Ji G, Zheng J, Shen Y, Wu X, Jiang R, Lin Y, Loke J C, Davis K M, Reese G J, Li Q Q (2007) Predictive modeling of plant messenger RNA polyadenylation sites. BMC Bioinformatics 8:43. doi: 10.1186/1471-2105-8-43

Ji, L., Xu, R., Lu, L., Zhang, J., Yang, G., Huang, J., et al. (2013). TM6, a novel nuclear matrix attachment region, enhances its flanking gene expression through influencing their chromatin structure. Mol. Cells 36, 127-137. doi:10.1007/s10059-013-0092-z.

Jiang X, Wang M, Graham D Y, Estes M K (1992) Expression, self-assembly, and antigenicity of the Norwalk virus capsid protein J Virol 66:6527-6532

Kato H, Xie G, Sato Y, Imai R (2010) Isolation of Anther-specific Gene Promoters Suitable for Transgene Expression in Rice. Plant Mol Biol Report 28:381-387. doi:10.1007/s11105-009-0162-8

Kertész S, Kerényi Z, Mérai Z, Bartos I, Pálfy T, Barta E, Silhavy D (2006) Both introns and long 3'-UTRs operate as cis-acting elements to trigger nonsense-mediated decay in plants Nucleic Acids Research 34:6147-6157 doi:10.1093/nar/gkl737

Komarova, T. V, Baschieri, S., Donini, M., Marusic, C., Benvenuto, E., and Dorokhov, Y. L. (2010). Transient expression systems for plant-derived biopharmaceuticals. Expert Rev. Vaccines 9, 859-876. doi:10.1586/erv.10.85.

Kooiker M, Airoldi C A, Losa A, Manzotti P S, Finzi L, Kater M M, Colombo L (2005) BASIC PENTACYSTEINE1, a GA binding protein that induces conformational changes in the regulatory region of the homeotic *Arabidopsis* gene SEEDSTICK. Plant Cell 17:722-729. doi:10.1105/tpc.104.030130

Lacroix, B., Loyter, A., and Citovsky, V. (2008). Association of the *Agrobacterium* T-DNA-protein complex with plant nucleosomes. Proc. Natl. Acad. Sci. 105, 15429-15434. doi:10.1073/pnas.0805641105.

Lai, H., He, J., Engle, M., Diamond, M. S., and Chen, Q. (2012). Robust production of virus-like particles and monoclonal antibodies with geminiviral replicon vectors in lettuce. Plant Biotechnol. J. 10, 95-104. doi:10.1111/j.1467-7652.2011.00649.x.

Libri D, Dower K, Boulay J, Thomsen R, Rosbash M, Jensen T H (2002) Interactions between mRNA export commitment, 3'-end quality control, and nuclear degradation. Mol Cell Biol 22:8254-8266. doi: 10.1128/MCB.22.23.8254-8266.2002

Liebich, I., Bode, J., Reuter, I., and Wingender, E. (2002). Evaluation of sequence motifs found in scaffold/matrix-attached regions (S/MARs). Nucleic Acids Res. 30, 3433-3442. doi:10.1093/nar/gkf446.

Limkul, J., Misaki, R., Kato, K., and Fujiyama, K. (2015). The combination of plant translational enhancers and terminator increase the expression of human glucocerebrosidase in Nicotiana benthamiana plants. Plant Sci. 240, 41-49. doi:10.1016/j.plantsci.2015.08.018.

Loke J C (2005) Compilation of mRNA Polyadenylation Signals in Arabidopsis Revealed a New Signal Element and Potential Secondary Structures. Plant Physiol 138: 1457-1468. doi: 10.1104/pp. 105.060541

Lomonossoff G P, D'Aoust M-A (2016) Plant-produced biopharmaceuticals: A case of technical developments driving clinical deployment. Science 353:1237-40. doi: 10.1126/science.aaf6638

Luo Z, Chen Z (2007) Improperly terminated, unpolyadenylated mRNA of sense transgenes is targeted by RDR6-mediated RNA silencing in Arabidopsis. Plant Cell 19:943-58. doi: 10.1105/tpc.106.045724

Lyon, G. M., Mehta, A. K., Varkey, J. B., Brantly, K., Plyler, L., McElroy, A. K., et al. (2014). Clinical Care of Two Patients with Ebola Virus Disease in the United States. N. Engl. J. Med. 371, 2402-2409. doi:10.1056/nejmoa1409838.

Macfarlane, S. A., Gilmer, D., and Davies, J. W. (1992). Efficient inoculation with CaMV 35 S promoter-driven DNA clones of the tobravirus PEBV. Virology 187, 829-831. doi:10.1016/0042-6822(92)90488-b.

Mandel C R, Bai Y, Tong L (2007) Protein factors in pre-mRNA 3'-end processing Cellular and Molecular Life Sciences 65:1099-1122 doi:10.1007/s00018-007-7474-3

Mankin, S. L., Allen, G. C., Phelan, T., Spiker, S., and Thompson, W. F. (2003). Elevation of transgene expression level by flanking matrix attachment regions (MAR) is promoter dependent: a study of the interactions of six promoters with the RB7 3' MAR. Transgenic Res 12, 3-12. Available at: http://www.ncbi.nlm.nih.gov/pubmed/12650520.

Mapendano C K, Lykke-Andersen S, Kjems J, Bertrand E, Jensen T H (2010) Crosstalk between mRNA 3' End Processing and Transcription Initiation Molecular Cell 40:410-422 doi:10.1016/j.molce1.2010.10.012

Mason H S, Ball J M, Shi J J, Jiang X, Estes M K, Arntzen C J (1996) Expression of Norwalk virus capsid protein in transgenic tobacco and potato and its oral immunogenicity in mice Proceedings of the National Academy of Sciences 93:5335-5340 doi:10.1073/pnas.93. 11.5335

Mason H S, Richter L J, Thanavala Y, Arntzen C J (2000) Nature Biotechnology 18:1167-1171 doi:10.1038/81153

Mathew L G, Maloney B, Takeda N, Mason H S (2011) Spurious polyadenylation of Norovirus Narita 104 capsid protein mRNA in transgenic plants Plant Molecular Biology 75:263-275 doi:10.1007/s11103-010-9725-1

Menossi M, Rabaneda F, Puigdomenech P, Martinez-Izquierdo J A (2003) Analysis of regulatory elements of the promoter and the 3' untranslated region of the maize Hrgp gene coding for a cell wall protein Plant Cell Rep 21:916-923 doi:10.1007/s00299-003-0602-0

Meshcheriakova, Y. A., Saxena, P., and Lomonossoff, G. P. (2014). Fine-tuning levels of heterologous gene expression in plants by orthogonal variation of the untranslated regions of a nonreplicating transient expression system. Plant Biotechnol. J. 12, 718-727. doi:10.1111/pbi.12175.

Millevoi S, Vagner S (2009) Molecular mechanisms of eukaryotic pre-mRNA 3' end processing regulation Nucleic Acids Research 38:2757-2774 doi:10.1093/nar/gkp1176

Mogen B D, MacDonald M H, Graybosch R, Hunt A G (1990) Upstream Sequences Other than AAUAAA Are Required for Efficient Messenger RNA 3'-End Formation in Plants The Plant Cell 2:1261 doi:10.2307/3869344

Mlynárová, L., Hricová, A., Loonen, A., and Nap, J.-P. (2003). The presence of a chromatin boundary appears to shield a transgene in tobacco from RNA silencing. Plant Cell 15, 2203-17. doi:10.1105/tpc.012070.

Moore M J, Proudfoot N J (2009) Pre-mRNA Processing Reaches Back to Transcription and Ahead to Translation Cell 136:688-700 doi:10.1016/j.cell.2009.02.001

Mor T S, Moon Y-S, Palmer K E, Mason H S (2002) Geminivirus vectors for high-level expression of foreign proteins in plant cells Biotechnology and Bioengineering 81:430-437 doi:10.1002/bit.10483

Nagaya S, Kawamura K, Shinmyo A, Kato K (2009) The HSP Terminator of Arabidopsis thaliana Increases Gene Expression in Plant Cells Plant and Cell Physiology 51:328-332 doi:10.1093/pcp/pcp188

Nandi, S., Kwong, A. T., Holtz, B. R., Erwin, R. L., Marcel, S., and McDonald, K. A. (2016). Techno-economic analysis of a transient plant-based platform for monoclonal antibody production. MAbs 8, 1456-1466. doi:10.1080/19420862.2016.1227901.

Narsai R, Howell K A, Millar A H, O'Toole N, Small I, Whelan J (2007) Genome-Wide Analysis of mRNA Decay Rates and Their Determinants in Arabidopsis thaliana. PLANT CELL ONLINE 19:3418-3436. doi: 10.1105/tpc.107.055046

Olinger, G. G., Pettitt, J., Kim, D., Working, C., Bohorov, O., Bratcher, B., et al. (2012). Delayed treatment of Ebola virus infection with plant-derived monoclonal antibodies provides protection in rhesus macaques. Proc. Natl. Acad. Sci. U.S.A 109, 18030-5. doi:10.1073/pnas.1213709109.

Pietrzak, M., Shillito, R. D., Hohn, T., and Potrykus, I. (1986). Expression in plants of two bacterial antibiotic resistance genes after protoplast transformation with a new plant expression vector. Nucleic Acids Res. 14, 5857-5868. doi:10.1093/nar/14.14.5857.

Qin, C., Shi, N., Gu, M., Zhang, H., Li, B., Shen, J., et al. (2012). Involvement of RDR6 in short-range intercellular RNA silencing in Nicotiana benthamiana. Sci. Rep. 2, 467. doi:10.1038/srep00467.

Qiu, X., Wong, G., Audet, J., Bello, A., Fernando, L., Alimonti, J. B., et al. (2014). Reversion of advanced Ebola virus disease in nonhuman primates with ZMapp. Nature 514, 47-53. doi:10.1038/nature13777.

Qu X, Lykke-Andersen S, Nasser T, Saguez C, Bertrand E, Jensen T H, Moore C (2009) Assembly of an Export-Competent mRNP Is Needed for Efficient Release of the 3'-End Processing Complex after Polyadenylation Molecular and Cellular Biology 29:5327-5338 doi: 10.1128/mcb.00468-09

Que, Q., Wang, H. Y., English, J. J., and Jorgensen, R. A. (1997). The Frequency and Degree of Cosuppression by Sense Chalcone Synthase Transgenes Are Dependent on Transgene Promoter Strength and Are Reduced by Premature Nonsense Codons in the Transgene Coding Sequence. Plant Cell 9, 1357-1368. doi:10.1105/tpc.9.8.1357.

Rethmeier N, Seurinck J, Van Montagu M, Cornelissen M (1997) Intron-mediated enhancement of transgene expression in maize is a nuclear, gene-dependent process The Plant Journal 12:895-899 doi:10.1046/j.1365-313x.1997.12040895.x Richter, L. J., Thanavala, Y., Arntzen, C. J., and Mason, H. S. (2000). Production of hepatitis B surface antigen in transgenic plants for oral immunization. Nat. Biotechnol. 18, 1167-71. doi:10.1038/81153.

Rose A B (2008) Intron-Mediated Regulation of Gene Expression. Springer Berlin Heidelberg. doi:10.1007/978-3-540-76776-3_15

Rosenthal, S. H., Diamos, A. G., and Mason, H. S. (2018). An intronless form of the tobacco extensin gene terminator strongly enhances transient gene expression in plant leaves. Plant Mol. Biol. doi:10.1007/s11103-018-0708-y.

Rothnie H M (1996) Plant mRNA 3?-end formation Plant Molecular Biology 32:43-61 doi:10.1007/bf00039376

Rothnie H M, Chen G, Futterer J, Hohn T (2001) Polyadenylation in Rice Tungro Bacilliform Virus: cis-Acting Signals and Regulation Journal of Virology 75:4184-4194 doi:10.1128/jvi.75.9.4184-4194.2001

Sainsbury, F., and Lomonossoff, G. P. (2008). Extremely high-level and rapid transient protein production in plants without the use of viral replication. Plant Physiol. 148, 1212-8. doi:10.1104/pp. 108.126284.

Sainsbury, F., Thuenemann, E. C., and Lomonossoff, G. P. (2009). pEAQ: versatile expression vectors for easy and quick transient expression of heterologous proteins in plants. Plant Biotechnol. J. 7, 682-93. doi:10.1111/j.1467-7652.2009.00434.x.

Sanfacon H, Brodmann P, Hohn T (1991) A dissection of the cauliflower mosaic virus polyadenylation signal Genes & Development 5:141-149 doi:10.1101/gad.5.1.141

Schubert, D., Lechtenberg, B., Forsbach, A., Gils, M., Bahadur, S., and Schmidt, R. (2004). Silencing in *Arabidopsis* T-DNA transformants: the predominant role of a gene-specific RNA sensing mechanism versus position effects. Plant Cell 16, 2561-72. doi:10.1105/tpc.104.024547.

Sharma A K, Sharma M K (2009) Plants as bioreactors: Recent developments and emerging opportunities Biotechnology Advances 27:811-832 doi:10.1016/j.biotechadv.2009.06.004

Sheldon C C, Conn A B, Dennis E S, Peacock W J (2002) Different Regulatory Regions Are Required for the Vernalization-Induced Repression of FLOWERING LOCUS C and for the Epigenetic Maintenance of Repression. Plant Cell Online 14:2527-2537. doi: 10.1105/tpc.004564

Showalter A M, Keppler B, Lichtenberg J, Gu D, Welch L R (2010) A Bioinformatics Approach to the Identification, Classification, and Analysis of Hydroxyproline-Rich Glycoproteins PLANT PHYSIOLOGY 153:485-513 doi: 10.1104/pp. 110.156554

Sieburth L E, Meyerowitz E M (1997) Molecular Dissection of the AGAMOUS Control Region Shows That cis Elements for Spatial Regulation Are Located Intragenically The Plant Cell 9:355 doi:10.2307/3870487

Simon, A. E., and Miller, W. A. (2013). 3' cap-independent translation enhancers of plant viruses. Annu. Rev. Microbiol. 67, 21-42. doi:10.1146/annurev-micro-092412-155609.

Singh, G., Pratt, G., Yeo, G. W., and Moore, M. J. (2015). The Clothes Make the mRNA: Past and Present Trends in mRNP Fashion. Annu. Rev. Biochem. 84, 325-354. doi: 10.1146/annurev-biochem-080111-092106.

Slomovic S, Schuster G (2013) Circularized RT-PCR (cRT-PCR). Elsevier. doi:10.1016/b978-O-12-420037-1.00013-0

Strasser, R., Altmann, F., and Steinkellner, H. (2014). Controlled glycosylation of plant-produced recombinant proteins. Curr. Opin. Biotechnol. 30, 95-100. doi:10.1016/j.copbio.2014.06.008.

Streatfield S J (2007) Approaches to achieve high-level heterologous protein production in plants Plant Biotechnology Journal 5:2-15 doi:10.1111/j.1467-7652.2006.00216.x Tan-Wong S M, Wijayatilake H D, Proudfoot N J (2009) Gene loops function to maintain transcriptional memory through interaction with the nuclear pore complex Genes & Development 23:2610-2624 doi:10.1101/gad.1823209

Tan-Wong S M et al. (2012) Gene Loops Enhance Transcriptional Directionality Science 338:671-675 doi: 10.1126/science.1224350

Thanavala Y, Huang Z, Mason H S (2006) Plant-derived vaccines: a look back at the highlights and a view to the challenges on the road ahead Expert Review of Vaccines 5:249-260 doi:10.1586/14760584.5.2.249

Tian B, Manley J L (2013) Alternative cleavage and polyadenylation: the long and short of it Trends in Biochemical Sciences 38:312-320 doi:10.1016/j.tib s.2013 0.03 0.005

Tokuhisa, J. G., Singh, K., Dennis, E. S., and Peacock, W. J. (1990). A DNA-Binding Protein Factor Recognizes Two Binding Domains within the Octopine Synthase Enhancer Element. Plant Cell 2, 215. doi:10.2307/3869136.

Tora L, Dantonel J-C, Murthy K G K, Manley J L (1997) Nature 389:399-402 doi: 10.1038/38763

Tusé, D., Tu, T., and McDonald, K. A. (2014). Manufacturing Economics of Plant-Made Biologics: Case Studies in Therapeutic and Industrial Enzymes. Biomed Res. Int. 2014, 1-16. doi:10.1155/2014/256135.

Wigington, C. P., Williams, K. R., Meers, M. P., Bassell, G. J., and Corbett, A. H. (2014). Poly(A) RNA-binding proteins and polyadenosine RNA: new members and novel functions. Wiley Interdiscip. Rev. RNA 5, 601-622. doi:10.1002/wrna.1233.

Wolterink-van Loo, S., Escamilla Ayala, A. A., Hooykaas, P. J. J., and van Heusden, G. P. H. (2015). Interaction of the *Agrobacterium tumefaciens* virulence protein VirD2 with histones. Microbiology 161, 401-10. doi:10.1099/mic.0.083410-0.

Xing A, Moon B P, Mills K M, Falco S C, Li Z (2010) Revealing frequent alternative polyadenylation and widespread low-level transcription read-through of novel plant transcription terminators Plant Biotechnology Journal 8:772-782 doi:10.1111/j 0.1467-7652.2010.00504.x Zhang X, Mason H (2006) Bean Yellow Dwarf Virus replicons for high-level transgene expression in transgenic plants and cell cultures Biotechnology and Bioengineering 93:271-279 doi:10.1002/bit.20695

Zhang, J., Lu, L., Ji, L., Yang, G., and Zheng, C. (2009). Functional characterization of a tobacco matrix attachment region-mediated enhancement of transgene expression. Transgenic Res. 18, 377-385. doi:10.1007/s11248-008-9230-3.

Zhao H, Xing D, Li Q Q (2009) Unique features of plant cleavage and polyadenylation specificity factor revealed by proteomic studies. Plant Physiol 151:1546-56. doi: 10.1104/pp. 109.142729

Zhao J, Hyman L, Moore C (1999) Formation of mRNA 3' ends in eukaryotes: mechanism, regulation, and interrelationships with other steps in mRNA synthesis Microbiol Mol Biol Rev 63:405-445

Zhao, C.-P., Guo, X., Chen, S.-J., Li, C.-Z., Yang, Y., Zhang, J.-H., et al. (2017). Matrix attachment region combinations increase transgene expression in transfected Chinese hamster ovary cells. Sci. Rep. 7, 42805. doi:10.1038/srep42805.

Zimran, A., Brill-Almon, E., Chertkoff, R., Petakov, M., Blanco-Favela, F., Munoz, E. T., et al. (2011). Pivotal trial with plant cell-expressed recombinant glucocerebrosidase, taliglucerase alfa, a novel enzyme replacement therapy for Gaucher disease. Blood 118, 5767-5773. doi:10.1182/blood-2011-07-366955.

We claim:

1. A plant expression vector comprising an expression cassette, wherein the expression cassette comprises a 5' UTR and a 3' UTR operably linked to a nucleotide sequence encoding a protein of interest, short intergenic region of bean yellow dwarf virus (SIR), and p19 suppresser of RNA silencing from tomato bushy stunt virus (P19); wherein the 3' UTR comprises:

a first terminator, wherein the first terminator is intronless tobacco extension terminator (EU); and a second terminator, wherein the second terminator is from a 3' UTR selected from the group consisting of: *Nicotiana benthamiana* actin 3' UTR (NbACT3), [p19 suppressor of RNA silencing from tomato bushy stunt virus (P19),] *N. benthamiana* 18.8 kDa class II heat shock protein 3' UTR (NbHSP), agrobacterium nopaline synthase 3' UTR (NOS), cauliflower mosaic virus 35S 3' UTR (35S), tobacco mosaic virus 3' UTR (TMV), BDBS501 (bean dwarf mosaic virus DNA B nuclear shuttle protein 3' UTR, the intergenic region, the 3' end of the movement protein, and additional 200 nt downstream of the movement protein sequence), tobacco necrosis virus-D 3' UTR (TNVD), pea enation mosaic virus 3' UTR (PEMV), and barley yellow dwarf virus 3' UTR (BYDV); wherein the first terminator and second terminator are operably linked.

2. The plant expression vector of claim 1, wherein the first terminator and second terminator form a double terminator.

3. The plant expression vector of claim 2, wherein the 3' UTR further comprises a chromatin scaffold/matrix attachment region (MAR) downstream of the double terminator.

4. The plant expression vector of claim 1, wherein the 3' UTR further comprises a chromatin scaffold/matrix attachment region (MAR).

5. The plant expression vector of claim 1, wherein EU is upstream of the second terminator.

6. The plant expression vector of claim 1, wherein the 3' UTR comprises EU and 35S, and wherein 35S is upstream of EU.

7. The plant expression vector of claim 4, wherein the first terminator, the second terminator and MAR are selected from the group consisting of:

EU, 35S, and Rb7, wherein EU is downstream or upstream of 35S;

EU, NbACT3, and Rb7, wherein EU is upstream of NbACT3;

EU, BD501, and Rb7, wherein EU is upstream of BD501;

EU, *A. thaliana* heat shock protein 3' UTR (AtHSP), and Rb7, wherein EU is downstream of AtHSP;

EU, 35S, and TM6, wherein EU is upstream of 35S.

8. The plant expression vector of claim 7, wherein the sequence of the plant expression vector is set forth in SEQ ID NO. 115, SEQ ID NO. 116, or SEQ ID NO. 117.

9. A method of producing recombinant protein in a plant or plant part, the method comprising introducing the plant expression vector of claim 1 into the plant or plant part.

10. The method of claim 9, wherein the plant or plant part is transformed by the plant expression vector of claim 1 using an *Agrobacterium*.

11. The method of claim 10, wherein the *Agrobacterium* is *Agrobacterium tumefaciens*.

12. The method of claim 9, wherein the plant or plant part is transformed by the vector of claim 1 via agroinfiltration.

13. The method of claim 9, wherein the plant is tobacco or lettuce or the plant part is from tobacco or lettuce.

* * * * *

UNITED STATES PATENT AND TRADEMARK OFFICE

CERTIFICATE OF CORRECTION

PATENT NO. : 12,286,636 B2
APPLICATION NO. : 16/976739
DATED : April 29, 2025
INVENTOR(S) : Hugh Mason, Andrew Diamos and Sun Hee Rosenthal It is certified that error appears in the above-identified patent and that said Letters Patent is hereby corrected as shown below:

On the Title Page

Item (73) should read --(73) Assignee: Arizona Board of Regents on Behalf of Arizona State University, Scottsdale, AZ (US)--

Signed and Sealed this
Fifth Day of August, 2025

Coke Morgan Stewart
*Acting Director of the United States Patent and Trademark Office*

SEQUENCE LISTING

```
<160> NUMBER OF SEQ ID NOS: 117

<210> SEQ ID NO 1
<211> LENGTH: 283
<212> TYPE: DNA
<213> ORGANISM: Artificial Sequence
<220> FEATURE:
<223> OTHER INFORMATION: NOS 3' region

<400> SEQUENCE: 1

gagctcagat cgttcaaaca tttggcaata aagtttctta agattgaatc ctgttgccgg     60

tcttgcgatg attatcatat aatttctgtt gaattacgtt aagcatgtaa taattaacat    120

gtaatgcatg acgttattta tgagatgggt ttttatgatt agagtcccgc aattatacat    180

ttaatacgcg atagaaaaca aaatatagcg cgcaaactag gataaattat cgcgcgcggt    240

gtcatctatg ttactagatc ggcgatcggg gctgcaggaa ttc                      283


<210> SEQ ID NO 2
<211> LENGTH: 223
<212> TYPE: DNA
<213> ORGANISM: Artificial Sequence
<220> FEATURE:
<223> OTHER INFORMATION: 35S 3' region

<400> SEQUENCE: 2

gagctcgtcc gcaaaaatca ccagtctctc tctacaaatc tatctctctc tatttttctc     60

cagaataatg tgtgagtagt tcccagataa gggaattagg gttcttatag ggtttcgctc    120

atgtgttgag catataagaa acccttagta tgtatttgta tttgtaaaat acttctatca    180

ataaaatttc taattcctaa aaccaaaatc cagtgacgaa ttc                      223


<210> SEQ ID NO 3
<211> LENGTH: 982
<212> TYPE: DNA
<213> ORGANISM: Artificial Sequence
<220> FEATURE:
<223> OTHER INFORMATION: PinII 3' region

<400> SEQUENCE: 3

gagctcgccc ggggatcctc tagagtaccc tgcaatgtga ccctagactt gtccatcttc     60

tggattggcc aagttaatta atgtatgaaa taaaaggatg cacacatagt gacatgctaa    120

tcactataat gtgggcatca aagttgtgtg ttatgtgtaa ttactaatta tctgaataag    180

agaaagagat catccatatt tcttatccta aatgaatgtc acgtgtcttt ataattcttt    240

gatgaaccag atgcatttta ttaaccaatt ccatatacat ataaatatta atcatatata    300

attaatatca attgggttag caaaacaaat ctagtctagg tgtgttttgc taattattgg    360

gggatagtgc aaaaagaaat ctacgttctc aataattcag atagaaaact taataaagtg    420

agataattta catagattgc ttttatcctt tgatatatgt gaaaccatgc atgatataag    480

gaaaatagat agagaaataa ttttttacat cgttgaatat gtaaacaatt taattcaaga    540
```

```
agctaggaat ataaatattg aggagtttat gattattatt attattttga tgttcaatga    600

agttttttt aatttcatat gaagtataca aaaattcttc atagattttt gtttctatgc    660

cgtagttatc tttaatatat ttgtggttga agaaatttat tgctagaaac gaatggattg    720

tcaatttttt tttaaagcaa atatatatga aattatactg tatattattt tagtcatgat    780

taaaatgtgg ccttaattga atcatctttc tcattcattt tttcaaaagc atatcaggat    840

gattgatatt tatctatttt aaaaattaat ttaagggttc aaattaaatt taacttaaaa    900

gtgtcctaac cgtagttaaa ggtttacttt aaaaaaatac tatgaaaaat ctaatcttct    960

atgaatcgac ctgcaggaat tc                                             982
```

```
<210> SEQ ID NO 4
<211> LENGTH: 695
<212> TYPE: DNA
<213> ORGANISM: Artificial Sequence
<220> FEATURE:
<223> OTHER INFORMATION: rbcS 3' region

<400> SEQUENCE: 4

gagctcccaa ttcgccctat agtgagtcgt attacgcgcg gagctttcgt tcgtatcatc     60

ggtttcgaca acgttcgtca agttcaatgc atcagtttca ttgcgcacac accagaatcc    120

tactgagttt gagtattatg gcattgggaa aactgttttt cttgtaccat ttgttgtgct    180

tgtaatttac tgtgtttttt attcggtttt cgctatcgaa ctgtgaaatg gaaatggatg    240

gagaagagtt aatgaatgat atggtccttt tgttcattct caaattaata ttatttgttt    300

tttctcttat ttgttgtgtg ttgaatttga aattataaga gatatgcaaa cattttgttt    360

tgagtaaaaa tgtgtcaaat cgtggcctct aatgaccgaa gttaatatga ggagtaaaac    420

acttgtagtt gtaccattat gcttattcac taggcaacaa atatattttc agacctagaa    480

aagctgcaaa tgttactgaa tacaagtatg tcctcttgtg ttttagacat ttatgaactt    540

tcctttatgt aattttccag aatccttgtc agattctaat cattgcttta taattatagt    600

tatactcatg gatttgtagt tgagtatgaa aatattttt aatgcatttt atgacttgcc    660

aattgattga caacatgcat caagctatcg aattc                                695
```

```
<210> SEQ ID NO 5
<211> LENGTH: 743
<212> TYPE: DNA
<213> ORGANISM: Artificial Sequence
<220> FEATURE:
<223> OTHER INFORMATION: intronless tobacco extensin 3' region

<400> SEQUENCE: 5

gagctcgaag tgacatcaca aagttgaagg taataaagcc aaattaatta agacattttc     60

ataatgatgt caagaatgca aagcaaattg cataactgcc tttatgcaaa acattaatat    120

aatataaatt ataaagaact gcgctctctg cttcttattt tcttagcttc atttattagt    180

cactagctgt tcagaatttt cagtatcttt tgatattact aagaacctaa tcacacaatg    240

tatattctta tgcaggaaaa gcagaatgct gagctaaaag aaaggctttt tccattttcg    300

agagacaatg agaaaagaag aagaagaaga agaagaagaa gaagaagaaa agagtaaata    360

ataaagcccc acaggaggcg aagttcttgt agctccatgt tatctaagtt attgatattg    420

tttgccctat attttatttc tgtcattgtg tatgttttgt tcagtttcga tctccttgca    480

aaatgcagag attatgagat gaataaacta agttatatta ttatacgtgt taatattctc    540
```

-continued

```
ctcctctctc tagctagcct tttgttttct ctttttctta tttgattttc tttaaatcaa    600

tccattttag gagagggcca gggagtgatc cagcaaaaca tgaagattag aagaaacttc    660

cctctttttt ttcctgaaaa caatttaacg tcgagattta tctcttttttg taatggaatc    720

atttctacag ttatgacgaa ttc                                            743
```

<210> SEQ ID NO 6
<211> LENGTH: 492
<212> TYPE: DNA
<213> ORGANISM: Artificial Sequence
<220> FEATURE:
<223> OTHER INFORMATION: intro-containing tobacco extensin 3' region

<400> SEQUENCE: 6

```
gagctcaaag cagaatgctg agctaaaaga aaggcttttt ccattttcga gagacaatga     60

gaaaagaaga agaagaagaa gaagaagaag aagaagaaaa gagtaaataa taaagcccca    120

caggaggcga agttcttgta gctccatgtt atctaagtta ttgatattgt ttgccctata    180

ttttatttct gtcattgtgt atgttttgtt cagtttcgat ctccttgcaa aatgcagaga    240

ttatgagatg aataaactaa gttatattat tatacgtgtt aatattctcc tcctctctct    300

agctagcctt ttgttttctc tttttcttat ttgattttct ttaaatcaat ccattttagg    360

agagggccag ggagtgatcc agcaaaacat gaagattaga agaaacttcc ctcttttttt    420

tcctgaaaac aatttaacgt cgagatttat ctctttttgt aatggaatca tttctacagt    480

tatgacgaat tc                                                        492
```

<210> SEQ ID NO 7
<211> LENGTH: 453
<212> TYPE: DNA
<213> ORGANISM: Artificial Sequence
<220> FEATURE:
<223> OTHER INFORMATION: NbHSP 3' region

<400> SEQUENCE: 7

```
gagctcactg aggaaatata tagacaaatt aagtttggtt ctatgagttc taatttggac     60

ttaagagttg tttgaaattc tattttatag tgatgcttat aatgtatttg gactgttttc    120

tgctgtgtgt aagacctttt ggtctgtgaa ctggaaacat acatgaataa atttctttga    180

atttactgga atttttgcat caacaaaaga aaaattgaag ttactaactt gtaaatggaa    240

caattgtaat gttaaaggat ataaatatct taatatagtg cgatacgaat cacacgaatg    300

caagactttc tctctctgct cccgctcatg ctctcggtgc atgttagcta aatatacatc    360

ggtgcatcca tggcaggagc atgaggacgg ggatgaggaa gggagtgagg agggccaaaa    420

gaagtacaca tagtttcctt tgggagcgaa ttc                                 453
```

<210> SEQ ID NO 8
<211> LENGTH: 1050
<212> TYPE: DNA
<213> ORGANISM: Artificial Sequence
<220> FEATURE:
<223> OTHER INFORMATION: NbACT 3' region

<400> SEQUENCE: 8

```
gagctcatac agcattccca gaaagagaaa cagaagaaat atacaaactt tcattttgag     60

agcagcacct cgtctattga ttgcagataa tatgcttctc atttgtattt ccttttgatt    120

atttttgttt ctatcccttt gtttgagtca atctcaaata ttcggtcatt gttggtatga    180

aaaatcaagc agttcatgtt aagagtcaat ttaaaattaa tatttttata tagagttgta    240
```

```
tgtgaaatga tgttgtgatt tggtatatat ggataaagag cttgtcagtt cattttggtc    300

tcattttttt ggtatccaaa taagaaacac aaaagggata tgtccctcta ctatcaaata    360

ttagttataa gtattcatgt tatactattc gatattttct accccaatcg ttacctattt    420

aaaagtattt accoctccat ctatcaaacc cctggaccca gctttcctat tacatgtggc    480

ttcatcttaa gcccccaaac ctttttctta tttttgattt ttaaaggctc atcttaaaat    540

ttattactca aattaatacc tcttaataac ccacctcaag gacccagtaa ttaaatatcc    600

aattagctcc agtaattggg gttcatatta gctccagtct taaattttaa aggcgatgat    660

cgtattcctc cacttggttc atttatactc aaagaatact caatgtcttt agtgtttaga    720

taacttttttg taaatcatat agattgtttt aacaaaaaac aattcaatag tagattttca    780

catgaaagtt acataaaaat tctttaaaat tactttctca aaaaattgtt ccaaacatat    840

tatcccacaa ttaaactcaa tctgtttttc gaaacctaaa tcaaaaccaa tccaactacc    900

ttatataata tataatcaat acattgtaaa gaactgcatg ttcttttaaa ttttgggggc    960

aaagttattc cgtacgttca cacatgtact aataggaggt aataaatgat atgtgaaaca   1020

atcgaggtgt aaacaagcta gcatgaattc                                    1050
```

```
<210> SEQ ID NO 9
<211> LENGTH: 217
<212> TYPE: DNA
<213> ORGANISM: Artificial Sequence
<220> FEATURE:
<223> OTHER INFORMATION: SIR

<400> SEQUENCE: 9

gaattccgag tgtacttcaa gtcagttgga aatcaataaa atgattattt tatgaatata     60

tttcattgtg caagtagata gaaattacat atgttacata acacacgaaa taaacaaaaa    120

aacacaatcc aaaacaaaca ccccaaacaa aataacacta tatatatcct cgtatgagga    180

gaggcacgtt cagtgactcg acgattccta ggccggc                             217
```

```
<210> SEQ ID NO 10
<211> LENGTH: 818
<212> TYPE: DNA
<213> ORGANISM: Artificial Sequence
<220> FEATURE:
<223> OTHER INFORMATION: SIR with extra 3'

<400> SEQUENCE: 10

gagctctaaa atgattattt tatgaatata tttcattgtg caagtagata gaaattacat     60

atgttacata acacacgaaa taaacaaaaa aacacaatcc aaaacaaaca ccccaaacaa    120

aataacacta tatatatcct cgtatgagga gaggcacgtt cagtgactcg acgattcccg    180

agcaaaaaaa gtctccccgt cacacatata gtgggtgacg caattatctt caaagtaatc    240

cttctgttga cttgtcattg ataacatcca gtcttcgtca ggattccaaa gaattataga    300

agggatccca ccttttattt tcttcttttt tccatattta gggttgacag tgaaatcaga    360

ctggcaacct attaattgct tccacaatgg gacgaacttg aaggggatgt cgtcgatgat    420

attataggtg gcgtgttcat cgtagttggt gaagtcgatg gtcccgttcc agtagttgtg    480

tcgcccgaga cttctagccc aggtggtctt tccggtacga gttggtccgc agatgtagag    540

gctggggtgt ctgaccccag tccttccctc atcctggtta gatcggccat ccactcaagg    600

tcagattgtg cttgatcgta ggagacagga tgtatgaaag tgtaggcatc gatgcttaca    660
```

-continued

```
tgatataggt gcgtctctct ccagttgtgc agatcttcgt ggcagcggag atctgattct    720

gtgaagggcg acacgtactg ctcaggttgt ggaggaaata atttgttggc tgaatattcc    780

agccattgaa gctttgttgc ccattcatga gggaattc                            818


<210> SEQ ID NO 11
<211> LENGTH: 1237
<212> TYPE: DNA
<213> ORGANISM: Artificial Sequence
<220> FEATURE:
<223> OTHER INFORMATION: SIR with 5' and 3' regions

<400> SEQUENCE: 11

gagctccatt tcatttttgg ctggtgtacg acaagtctcc tggtgctaat gttcccagta     60

ctggggatat atttgaggga ccttcgttgt ttcctcataa tccttggacg tggactgtgt    120

ctagggctgc ttgccatcgt tttgtggtga agaaaacgtg gtcatgcgtg gtggagagca    180

atggtattga cccaaccaaa ggtcaaggag ctacttatta tgggcctggg ccttgtaatc    240

aggttaagtc ctgtaataag ttctttaaga gattgggtgt gtccacagag tggaaaaata    300

gtgcaacggg tgatgttggt gatataaagg aaggagccct ttacattgtt ggtgctcctt    360

cccaaaagtc cgatgtatat gtaaatggtt atttccgagt gtacttcaag tcagttggaa    420

atcaataaaa tgattatttt atgaatatat ttcattgtgc aagtagatag aaattacata    480

tgttacataa cacacgaaat aaacaaaaaa acacaatcca aaacaaacac cccaaacaaa    540

ataacactat atatatcctc gtatgaggag aggcacgttc agtgactcga cgattcccga    600

gcaaaaaaag tctccccgtc acacatatag tgggtgacgc aattatcttc aaagtaatcc    660

ttctgttgac ttgtcattga taacatccag tcttcgtcag gattccaaag aattatagaa    720

gggatcccac cttttatttt cttctttttt ccatatttag ggttgacagt gaaatcagac    780

tggcaaccta ttaattgctt ccacaatggg acgaacttga aggggatgtc gtcgatgata    840

ttataggtgg cgtgttcatc gtagttggtg aagtcgatgg tcccgttcca gtagttgtgt    900

cgcccgagac ttctagccca ggtggtcttt ccggtacgag ttggtccgca gatgtagagg    960

ctggggtgtc tgaccccagt ccttccctca tcctggttag atcggccatc cactcaaggt   1020

cagattgtgc ttgatcgtag gagacaggat gtatgaaagt gtaggcatcg atgcttacat   1080

gatataggtg cgtctctctc cagttgtgca gatcttcgtg gcagcggaga tctgattctg   1140

tgaagggcga cacgtactgc tcaggttgtg gaggaaataa tttgttggct gaatattcca   1200

gccattgaag ctttgttgcc cattcatgag ggaattc                            1237


<210> SEQ ID NO 12
<211> LENGTH: 513
<212> TYPE: DNA
<213> ORGANISM: Artificial Sequence
<220> FEATURE:
<223> OTHER INFORMATION: BDB501

<400> SEQUENCE: 12

gagctctgac aacatcagca agaacgccct cctagtatat tactgttgga tgtcagatac     60

tatgtcaaag gcatctactt ttgtatcgtt tgaccttgat tatatcggtt gattaatgat    120

aattgtaata aaaagctatt attgaacttt caattcctca acaaagaaat tattgcaacg    180

atttgggctg ataagcctta cagttactat ttatacactc ctggacagtg tttttcacta    240

gctcgtttaa ttgccccatc gacatagtaa tgttggattc cgctctctgg gcccctacaa    300

ttgaggcaga ctcccctggg tctaagacgc ttgttccaag cctgctgaga tgcctatatg    360
```

-continued

```
gatgcattgc gttttccacc tctgagtcgg catcggagtt gctgagccca attgtactcc    420

gtgaagccca tgattcaccc ggcttgatct ctattgggcc tggtagtcca atccttgaca    480

tggatgcgca tcttatgggt ttcctttgaa ttc                                 513


<210> SEQ ID NO 13
<211> LENGTH: 261
<212> TYPE: DNA
<213> ORGANISM: Artificial Sequence
<220> FEATURE:
<223> OTHER INFORMATION: AtHSP 3' region

<400> SEQUENCE: 13

gagctcatat gaagatgaag atgaaatatt tggtgtgtca aataaaaagc ttgtgtgctt     60

aagtttgtgt ttttttcttg gcttgttgtg ttatgaattt gtggcttttt ctaatatcaa    120

atgaatgtaa gatctcatta taatgaataa acaaatgttt ctataatcca ttgtgaatgt    180

tttgttggat ctcttctgca gcatataact actgtatgtg ctatggtatg gactatggaa    240

tatgattaaa gataagaatt c                                              261


<210> SEQ ID NO 14
<211> LENGTH: 675
<212> TYPE: DNA
<213> ORGANISM: Artificial Sequence
<220> FEATURE:
<223> OTHER INFORMATION: Rep 3' region

<400> SEQUENCE: 14

gagctctaat aggttgccag tctgatttca ctgtcaaccc taaatatgga aaaaagaaga     60

aaataaaagg tgggatccct tctataattc tttggaatcc tgacgaagac tggatgttat    120

caatgacaag tcaacagaag gattactttg aagataattg cgtcacccac tatatgtgtg    180

acggggagac ttttttttgct cgggaatcgt cgagtcactg aacgtgcctc tcctcatacg    240

aggatatata tagtgttatt ttgtttgggg tgtttgtttt ggattgtgtt tttttgttta    300

tttcgtgtgt tatgtaacat atgtaatttc tatctacttg cacaatgaaa tatattcata    360

aaataatcat tttattgatt tccaactgac ttgaagtaca ctcggaaata accatttaca    420

tatacatcgg acttttggga aggagcacca acaatgtaaa gggctccttc ctttatatca    480

ccaacatcac ccgttgcact atttttccac tctgtggaca cacccaatct cttaaagaac    540

ttattacagg acttaacctg attacaaggc ccaggcccat aataagtagc tccttgacct    600

ttggttgggt caataccatt gctctccacc acgcatgacc acgttttctt caccacaaaa    660

cgatggcaag aattc                                                     675


<210> SEQ ID NO 15
<211> LENGTH: 463
<212> TYPE: DNA
<213> ORGANISM: Artificial Sequence
<220> FEATURE:
<223> OTHER INFORMATION: RepA 3' region

<400> SEQUENCE: 15

gagctctgaa cgtgcctctc ctcatacgag gatatatata gtgttatttt gtttggggtg     60

tttgttttgg attgtgtttt tttgtttatt tcgtgtgtta tgtaacatat gtaatttcta    120

tctacttgca caatgaaata tattcataaa ataatcattt tattgatttc caactgactt    180

gaagtacact cggaaataac catttacata tacatcggac ttttgggaag gagcaccaac    240
```

aatgtaaagg gctccttcct ttatatcacc aacatcaccc gttgcactat ttttccactc 300
tgtggacaca cccaatctct taaagaactt attacaggac ttaacctgat tacaaggccc 360
aggcccataa taagtagctc cttgaccttt ggttgggtca ataccattgc tctccaccac 420
gcatgaccac gttttcttca ccacaaaacg atggcaagaa ttc 463

<210> SEQ ID NO 16
<211> LENGTH: 1175
<212> TYPE: DNA
<213> ORGANISM: Artificial Sequence
<220> FEATURE:
<223> OTHER INFORMATION: Rb7 MAR

<400> SEQUENCE: 16
gaattctcga ttaaaaatcc caattatatt tggtctaatt tagtttggta ttgagtaaaa 60
caaattcgaa ccaaaccaaa atataaatat atagttttta tatatatgcc tttaagactt 120
tttatagaat tttctttaaa aaatatctag aaatatttgc gactcttctg gcatgtaata 180
tttcgttaaa tatgaagtgc tccatttttta ttaactttaa ataattggtt gtacgatcac 240
tttcttatca agtgttacta aaatgcgtca atctctttgt tcttccatat tcatatgtca 300
aaatctatca aaattcttat atatcttttt cgaatttgaa gtgaaatttc gataatttaa 360
aattaaatag aacatatcat tatttaggta tcatattgat tttatactt aattactaaa 420 tttggttaac tttgaaagtg tacatcaacg aaaaattagt caaacgacta aaataaataa 480
atatcatgtg ttattaagaa aattctccta taagaatatt ttaatagatc atatgtttgt 540
aaaaaaaatt aatttttact aacacatata tttacttatc aaaaatttga caaagtaaga 600
ttaaaataat attcatctaa caaaaaaaaa accagaaaat gctgaaaacc cggcaaaacc 660
gaaccaatcc aaaccgatat agttggtttg gtttgatttt gatataaacc gaaccaactc 720
ggtccatttg cacccctaat cataatagct ttaatatttc aagatattat taagttaacg 780
ttgtcaatat cctggaaatt ttgcaaaatg aatcaagcct atatggctgt aatatgaatt 840
taaaagcagc tcgatgtggt ggtaatatgt aatttacttg attctaaaaa aatatcccaa 900
gtattaataa tttctgctag gaagaaggtt agctacgatt tacagcaaag ccagaataca 960
aagaaccata aagtgattga agctcgaaat atacgaagga acaaatattt ttaaaaaaat 1020
acgcaatgac ttggaacaaa agaaagtgat atatttttg ttcttaaaca agcatcccct 1080
ctaaagaatg gcagttttcc tttgcatgta actattatgc tcccttcgtt acaaaaattt 1140
tggactacta ttgggaactt cttctgaaaa tagtg 1175

<210> SEQ ID NO 17
<211> LENGTH: 1211
<212> TYPE: DNA
<213> ORGANISM: Artificial Sequence
<220> FEATURE:
<223> OTHER INFORMATION: TM6 MAR

<400> SEQUENCE: 17
gaattcaggt aatatttaga aatttaatta acataaccaa ggatttttat atcggtaata 60
actctaatat ggtatccaaa tcagtctaga actctcttac ctctaataag taaaagtact 120
tctaataaat tcatatactt tttctctctt ctccgatctc tctttgctct tctttttatg 180
tatcctttcc tttctaatag ccttttatga gaagtaaact tttagggttg gcccccccctc 240 cccccacaat tatatagttt cttactcagt tgttggaata taattcaaat tcttaaataa 300
ttgacggtga cattgagttt tactttgtgg aagagaatta gattctcgtg ttagtaaaat 360
cggttagtaa ttgatgatgc attattttta ctctataata gagatgcaat tttatttttg 420
cattttggga tcaaattgta atgcagtcat atattgattt cataaatgtt tgggatattg 480
ttggttattt aactagaaat agacttctta tttcatattt attgttaaaa tcctttattg 540
gagatgaatt atttgttcaa cgattagaag ttgatagtcg cttttgtttt agaagaaatt 600
ttaccgtaga ccaagttaag gagttttaga agcactttgc atgggagcat tagtgtatgt 660
tatggcttta tcaaatatag gttttgaaga ttcagagagc caagaaaagc tagaacccaa 720
gaactaggaa gttagagtaa ttcacaatac cataacgtga tataaaactt tttattgtaa 780
ctcaaatcgg taatattttt tgctttagtc ttaatcgata aattattttt ttatattgat 840
tagttatagg aggctcaaaa agttgggaat aattaaaata tcatattttg tatttgaaca 900
atttatgaaa tagtaattgg taaaaaatca ctttaaattt ttatcctata tccagaagga 960
ttatggtgtc tggcatagtt gtttggaaga tttgaatcag ggtaaaagta tgttgtaatt 1020
tttattttgt tataggcatt ttttgtgctt gattgttttg ttgtcattat attttattat 1080
ttggaagtgt atatatatgt ttgattaaaa tatagataat caattttata agaaatttgc 1140
aacaattaca aaaggataaa gtctacaata tgcgagtaaa atttgattga acctaggatg 1200
tccctgaatt c 1211

<210> SEQ ID NO 18
<211> LENGTH: 881
<212> TYPE: DNA
<213> ORGANISM: Artificial Sequence
<220> FEATURE:
<223> OTHER INFORMATION: BYDV 3' region

<400> SEQUENCE: 18
ggtaccagtg aagacaacac cactagcaca aatcggatcc tgggaaacag gcagaacttc 60
ggttcataag ctcgggtagg ctgtcaacct accgccgtat cgtattgtgt ttggccgatg 120
gaggatcttc acgttatcgc cgtttgtatt cttgccttga ctgtgctctc tggggtaggc 180
gctgttttga gttgctgccg ttggtgctgc agcaatcctt ttcctccctc cctctcttct 240
gtttaagcaa aagactctcg atctgtgcga gagacaatca aaaatatcga gggagcttcg 300
gctcagtgag ggattaacgg acccccagta atggccggtc ctggcggaca taaataaccc 360
gctataggac gaagtggtag ccaccactga tcaaatggca aacatgcttc tgtgttgtac 420
actgccccgg agcctaccgg gtcaacaagg ctatcccacc aacccgatga aatgagggtg 480
gagtgagcgg agtgggtgac ttcgtgatgt acacccgatc gtcaggattg aagacgttaa 540
aactcgacga cctggtacaa gtcgttaaac tgactcgggt ggatacacca cacccggccc 600
agcatgttgg catacccacg atacgaaacg tgggtctctt ggagccacta cctgtgatgc 660
aaggtagggt atgagtctta gcaagctctg agccaggaga tggacataaa ccatagcaat 720
ccaacgtgta accgcaatgg ggcaaacaac aggtgaaccg tgtccacggg cctggttacc 780
gaaaggaaag ccagtatcca acacagcaat gtgttggggg tcacaccctc ggggtactct 840
taacgctgac actcgaaaga gcagttcggc aacccgagct c 881

<210> SEQ ID NO 19
<211> LENGTH: 246
<212> TYPE: DNA
<213> ORGANISM: Artificial Sequence
<220> FEATURE:
<223> OTHER INFORMATION: TNVD 3' region

<400> SEQUENCE: 19
ggtaccttgc tttcatagat ccgtcttccc agagacgtta agaagaagct ggagaaaaat 60
attaggttag aagcttgggc gtgacaaacc caagttgcat ctcttacgtg gttaatcaca 120
ctgtatgttg acgtacaagc cggatcctgg gaaacaggtt taacggctca ctgtggtggt 180
gggccgtcga tacacttgta tgtgccccaa tattggttgt cgagatctct ctaggaaccc 240
gagctc 246

<210> SEQ ID NO 20
<211> LENGTH: 710
<212> TYPE: DNA
<213> ORGANISM: Artificial Sequence
<220> FEATURE:
<223> OTHER INFORMATION: PEMV 3' region

<400> SEQUENCE: 20
ggcttcgctt cccgccggaa gaccgcggcg gttctgttcc tcccacagga gtacggcaac 60
aacccacctt gggaaagtgg ggaccccagc actaactcct ttaactaggc gggcgtgttg 120
gttacagtag gaggggacag tgcgcatcga aactgagccc caccacaact ctcatccacg 180
gggtggttgg gacgcaggtg tcggagggat cgccagccct caggatagtg agctcccgca 240
gagggataag ctatctccct gcgacgtagt ggtagaacac gtgggatagg ggatgacctt 300
gtcgaccggt tatcggtccc ctgctccttc gagctggcaa ggcgctcaca ggttctacac 360
tgctactaaa gttggtggtg gatgtctcgc ccaaaaagat cacaaacgcg cgggacaagg 420
tcccttccac cttcgccggg taaggctaga gtcagcgctg catgactata acttgcggcc 480
gatccagttg cacgactggt ggtccccctc agtgtctcgg ttgtctgccg agtgggcggt 540
ggtcggattc caccacaccc tgccacgagg tgcgtggaga cttggccagt ctaggctcgt 600
cgtaattagt tgcagcgacg ttaatcaacc cgtccgggca tataatagga ccggttgtgc 660
ttcttcctcc cttcttagcc aggtggttac ctccctggcg cccgggtacc 710

<210> SEQ ID NO 21
<211> LENGTH: 215
<212> TYPE: DNA
<213> ORGANISM: Artificial Sequence
<220> FEATURE:
<223> OTHER INFORMATION: TMV 3' region

<400> SEQUENCE: 21
ggtaccggta gtcaagatgc ataataaata acggattgtg tccgtaatca cacgtggtgc 60
gtacgataac gcatagtgtt tttccctcca cttaaatcga agggttgtgt cttggatcgc 120
gcgggtcaaa tgtatatggt tcatatacat ccgcaggcac gtaataaagc gaggggttcg 180
aatccccccg ttacccccgg taggggccca gagct 215

<210> SEQ ID NO 22
<211> LENGTH: 41
<212> TYPE: DNA
<213> ORGANISM: Artificial Sequence
<220> FEATURE:
<223> OTHER INFORMATION: primer

<400> SEQUENCE: 22
gttgttgttg ttgttgtttt gtgatgtttg aacgatcggg g 41

<210> SEQ ID NO 23
<211> LENGTH: 47

-continued

<212> TYPE: DNA
<213> ORGANISM: Artificial Sequence
<220> FEATURE:
<223> OTHER INFORMATION: primer

<400> SEQUENCE: 23
caacaacaac aacaacaaaa cattggcaat aaagtttctt aagattg 47

<210> SEQ ID NO 24
<211> LENGTH: 44
<212> TYPE: DNA
<213> ORGANISM: Artificial Sequence
<220> FEATURE:
<223> OTHER INFORMATION: primer

<400> SEQUENCE: 24
tgttttgttg ttgttgttgt tgttgttgtt gttgttgttt tgtg 44

<210> SEQ ID NO 25
<211> LENGTH: 44
<212> TYPE: DNA
<213> ORGANISM: Artificial Sequence
<220> FEATURE:
<223> OTHER INFORMATION: primer

<400> SEQUENCE: 25
cacaaaacaa caacaacaac aacaacaaca acaacaacaa aaca 44

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
gtgagctcgt ccgcaaaaat caccag 26

<210> SEQ ID NO 27
<211> LENGTH: 30
<212> TYPE: DNA
<213> ORGANISM: Artificial Sequence
<220> FEATURE:
<223> OTHER INFORMATION: primer

<400> SEQUENCE: 27
cagaattcgt cactggattt tggttttagg 30

<210> SEQ ID NO 28
<211> LENGTH: 36
<212> TYPE: DNA
<213> ORGANISM: Artificial Sequence
<220> FEATURE:
<223> OTHER INFORMATION: primer

<400> SEQUENCE: 28
cgctgtgctg ccgtgccttt tttttttttt tttttt 36

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29

-continued cgctgtgctg ccgtgcctt 19

<210> SEQ ID NO 30
<211> LENGTH: 32
<212> TYPE: DNA
<213> ORGANISM: Artificial Sequence
<220> FEATURE:
<223> OTHER INFORMATION: primer

<400> SEQUENCE: 30
ggctttatta tttaattgtc tctcgaaaat gg 32

<210> SEQ ID NO 31
<211> LENGTH: 32
<212> TYPE: DNA
<213> ORGANISM: Artificial Sequence
<220> FEATURE:
<223> OTHER INFORMATION: primer

<400> SEQUENCE: 31
tcgagagaca attaaataat aaagccccac ag 32

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
ctggtggttt tgaagctggt a 21

<210> SEQ ID NO 33
<211> LENGTH: 23
<212> TYPE: DNA
<213> ORGANISM: Artificial Sequence
<220> FEATURE:
<223> OTHER INFORMATION: primer

<400> SEQUENCE: 33
cacgcattgc ttgctttcac cct 23

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
ggtggtagca tccatcttgt t 21

<210> SEQ ID NO 35
<211> LENGTH: 46
<212> TYPE: DNA
<213> ORGANISM: Artificial Sequence
<220> FEATURE:
<223> OTHER INFORMATION: primer

<400> SEQUENCE: 35
atcatcatca tcatcaattc acattgtctc tcgaaaatgg aaaaag 46

<210> SEQ ID NO 36
<211> LENGTH: 44
<212> TYPE: DNA
<213> ORGANISM: Artificial Sequence
<220> FEATURE:
<223> OTHER INFORMATION: primer

<400> SEQUENCE: 36
gatgatgatg atgatgaatt gtgtaaataa taaagcccca cagg 44

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
gtgagctcga agtgacatca caaagttgaa g 31

<210> SEQ ID NO 38
<211> LENGTH: 31
<212> TYPE: DNA
<213> ORGANISM: Artificial Sequence
<220> FEATURE:
<223> OTHER INFORMATION: primer

<400> SEQUENCE: 38
cagaattcgt cataactgta gaaatgattc c 31

<210> SEQ ID NO 39
<211> LENGTH: 27
<212> TYPE: DNA
<213> ORGANISM: Artificial Sequence
<220> FEATURE:
<223> OTHER INFORMATION: primer

<400> SEQUENCE: 39
gtgagctcaa agcagaatgc tgagcta 27

<210> SEQ ID NO 40
<211> LENGTH: 33
<212> TYPE: DNA
<213> ORGANISM: Artificial Sequence
<220> FEATURE:
<223> OTHER INFORMATION: primer

<400> SEQUENCE: 40
cagaattcgg ctagctagag agaggaggag aat 33

<210> SEQ ID NO 41
<211> LENGTH: 37
<212> TYPE: DNA
<213> ORGANISM: Artificial Sequence
<220> FEATURE:
<223> OTHER INFORMATION: primer

<400> SEQUENCE: 41
cagaattcga aactgaacaa aacatacaca atgacag 37

<210> SEQ ID NO 42
<211> LENGTH: 33
<212> TYPE: DNA
<213> ORGANISM: Artificial Sequence
<220> FEATURE:
<223> OTHER INFORMATION: primer

<400> SEQUENCE: 42
tgcgagctcc tgcataagaa tatacattgt gtg 33

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
atggtcctgc tggagttcgt gacc 24

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
gtccaggagc gcaccatctt ct 22

<210> SEQ ID NO 45
<211> LENGTH: 27
<212> TYPE: DNA
<213> ORGANISM: Artificial Sequence
<220> FEATURE:
<223> OTHER INFORMATION: primer

<400> SEQUENCE: 45
cgggtcttgt agttgccgtc gtccttg 27

<210> SEQ ID NO 46
<211> LENGTH: 24
<212> TYPE: DNA
<213> ORGANISM: Artificial Sequence
<220> FEATURE:
<223> OTHER INFORMATION: primer

<400> SEQUENCE: 46
gatgcccttc agctcgatgc ggtt 24

<210> SEQ ID NO 47
<211> LENGTH: 21
<212> TYPE: DNA
<213> ORGANISM: Artificial Sequence
<220> FEATURE:
<223> OTHER INFORMATION: primer

<400> SEQUENCE: 47
gtcctgctgg agttcgtgac c 21

<210> SEQ ID NO 48
<211> LENGTH: 27
<212> TYPE: DNA
<213> ORGANISM: Artificial Sequence
<220> FEATURE:
<223> OTHER INFORMATION: primer

<400> SEQUENCE: 48
gcatggacga gctgtacaag taagagc 27

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
cgtttacgtc gccgtccagc 20

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
ctcgcccttg ctcaccattg ttc 23

<210> SEQ ID NO 51
<211> LENGTH: 33
<212> TYPE: DNA
<213> ORGANISM: Artificial Sequence
<220> FEATURE:
<223> OTHER INFORMATION: primer

<400> SEQUENCE: 51
gtctcgagaa caatgttacg tcctgtagaa acc 33

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
acgagctctc attgtttgcc tccctgc 27

<210> SEQ ID NO 53
<211> LENGTH: 40
<212> TYPE: DNA
<213> ORGANISM: Artificial Sequence
<220> FEATURE:
<223> OTHER INFORMATION: primer

<400> SEQUENCE: 53
ttcttcttct tcttcttttc tcatgtttga acgatcgggg 40

<210> SEQ ID NO 54
<211> LENGTH: 47
<212> TYPE: DNA
<213> ORGANISM: Artificial Sequence
<220> FEATURE:
<223> OTHER INFORMATION: primer

<400> SEQUENCE: 54
gaagaagaag aagaagaaaa gattggcaat aaagtttctt aagattg 47

<210> SEQ ID NO 55
<211> LENGTH: 42
<212> TYPE: DNA
<213> ORGANISM: Artificial Sequence
<220> FEATURE:
<223> OTHER INFORMATION: primer

<400> SEQUENCE: 55
ttcttcttct tcttcttttc tcaggattca atcttaagaa ac 42

<210> SEQ ID NO 56

<211> LENGTH: 41
<212> TYPE: DNA
<213> ORGANISM: Artificial Sequence
<220> FEATURE:
<223> OTHER INFORMATION: primer

<400> SEQUENCE: 56
gaagaagaag aagaagaaaa gaggttgccg gtcttgcgat g 41

<210> SEQ ID NO 57
<211> LENGTH: 40
<212> TYPE: DNA
<213> ORGANISM: Artificial Sequence
<220> FEATURE:
<223> OTHER INFORMATION: primer

<400> SEQUENCE: 57
atcatcatca tcatcaattc acatgtttga acgatcgggg 40

<210> SEQ ID NO 58
<211> LENGTH: 47
<212> TYPE: DNA
<213> ORGANISM: Artificial Sequence
<220> FEATURE:
<223> OTHER INFORMATION: primer

<400> SEQUENCE: 58
gatgatgatg atgatgaatt gtttggcaat aaagtttctt aagattg 47

<210> SEQ ID NO 59
<211> LENGTH: 22
<212> TYPE: DNA
<213> ORGANISM: Artificial Sequence
<220> FEATURE:
<223> OTHER INFORMATION: primer

<400> SEQUENCE: 59
ctcgaattcc cgatctagta ac 22

<210> SEQ ID NO 60
<211> LENGTH: 41
<212> TYPE: DNA
<213> ORGANISM: Artificial Sequence
<220> FEATURE:
<223> OTHER INFORMATION: primer

<400> SEQUENCE: 60
cagccctaca actatatccg atgatgtttg aacgatcggg g 41

<210> SEQ ID NO 61
<211> LENGTH: 47
<212> TYPE: DNA
<213> ORGANISM: Artificial Sequence
<220> FEATURE:
<223> OTHER INFORMATION: primer

<400> SEQUENCE: 61
gagtaaatat tacgagtcga ggttggcaat aaagtttctt aagattg 47

<210> SEQ ID NO 62
<211> LENGTH: 44
<212> TYPE: DNA
<213> ORGANISM: Artificial Sequence
<220> FEATURE:
<223> OTHER INFORMATION: primer

<400> SEQUENCE: 62
cctcgactcg taatatttac tcagccctac aactatatcc gatg 44

<210> SEQ ID NO 63
<211> LENGTH: 44
<212> TYPE: DNA
<213> ORGANISM: Artificial Sequence
<220> FEATURE:
<223> OTHER INFORMATION: primer

<400> SEQUENCE: 63
catcggatat agttgtaggg ctgagtaaat attacgagtc gagg 44

<210> SEQ ID NO 64
<211> LENGTH: 21
<212> TYPE: DNA
<213> ORGANISM: Artificial Sequence
<220> FEATURE:
<223> OTHER INFORMATION: primer

<400> SEQUENCE: 64
aacgattgaa ggagccactc a 21

<210> SEQ ID NO 65
<211> LENGTH: 19
<212> TYPE: DNA
<213> ORGANISM: Artificial Sequence
<220> FEATURE:
<223> OTHER INFORMATION: primer

<400> SEQUENCE: 65
actgaaggcg ggaaacgac 19

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
gtggttggca tgcacataca a 21

<210> SEQ ID NO 67
<211> LENGTH: 18
<212> TYPE: DNA
<213> ORGANISM: Artificial Sequence
<220> FEATURE:
<223> OTHER INFORMATION: primer

<400> SEQUENCE: 67
atttgcctgc gcacctgt 18

<210> SEQ ID NO 68
<211> LENGTH: 22
<212> TYPE: DNA
<213> ORGANISM: Artificial Sequence
<220> FEATURE:
<223> OTHER INFORMATION: primer

<400> SEQUENCE: 68
aatggtgcta gcagcggtcc ac 22

<210> SEQ ID NO 69
<211> LENGTH: 23
<212> TYPE: DNA

-continued

<213> ORGANISM: Artificial Sequence
<220> FEATURE:
<223> OTHER INFORMATION: primer

<400> SEQUENCE: 69
caatgtccaa agtgtgcaat tcc 23

<210> SEQ ID NO 70
<211> LENGTH: 22
<212> TYPE: DNA
<213> ORGANISM: Artificial Sequence
<220> FEATURE:
<223> OTHER INFORMATION: primer

<400> SEQUENCE: 70
tgatggaaga cttgttggca cc 22

<210> SEQ ID NO 71
<211> LENGTH: 24
<212> TYPE: DNA
<213> ORGANISM: Artificial Sequence
<220> FEATURE:
<223> OTHER INFORMATION: primer

<400> SEQUENCE: 71
cctcttatct tggcaacatg tgac 24

<210> SEQ ID NO 72
<211> LENGTH: 44
<212> TYPE: DNA
<213> ORGANISM: Artificial Sequence
<220> FEATURE:
<223> OTHER INFORMATION: primer

<400> SEQUENCE: 72
gagaaaagaa gaagaagaag aagaagaaga agaagaagaa aaga 44

<210> SEQ ID NO 73
<211> LENGTH: 44
<212> TYPE: DNA
<213> ORGANISM: Artificial Sequence
<220> FEATURE:
<223> OTHER INFORMATION: primer

<400> SEQUENCE: 73
tcttttcttc ttcttcttct tcttcttctt cttcttcttt tctc 44

<210> SEQ ID NO 74
<211> LENGTH: 44
<212> TYPE: DNA
<213> ORGANISM: Artificial Sequence
<220> FEATURE:
<223> OTHER INFORMATION: primer

<400> SEQUENCE: 74
gtgaattgat gatgatgatg atgatgatga tgatgatgaa ttgt 44

<210> SEQ ID NO 75
<211> LENGTH: 44
<212> TYPE: DNA
<213> ORGANISM: Artificial Sequence
<220> FEATURE:
<223> OTHER INFORMATION: primer

<400> SEQUENCE: 75
acaattcatc atcatcatca tcatcatcat catcatcaat tcac 44

<210> SEQ ID NO 76
<211> LENGTH: 42
<212> TYPE: DNA
<213> ORGANISM: Artificial Sequence
<220> FEATURE:
<223> OTHER INFORMATION: primer

<400> SEQUENCE: 76
tccgaattct aatatttaga aatttaatta acataaccaa gg 42

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
ctggtaccga catcctaggt tcaatcaaat 30

<210> SEQ ID NO 78
<211> LENGTH: 26
<212> TYPE: DNA
<213> ORGANISM: Artificial Sequence
<220> FEATURE:
<223> OTHER INFORMATION: primer

<400> SEQUENCE: 78
gagtctagaa catggtgcgc tcctcc 26

<210> SEQ ID NO 79
<211> LENGTH: 26
<212> TYPE: DNA
<213> ORGANISM: Artificial Sequence
<220> FEATURE:
<223> OTHER INFORMATION: primer

<400> SEQUENCE: 79
tgaatagtgc atatcagcat acctta 26

<210> SEQ ID NO 80
<211> LENGTH: 27
<212> TYPE: DNA
<213> ORGANISM: Artificial Sequence
<220> FEATURE:
<223> OTHER INFORMATION: primer

<400> SEQUENCE: 80
agggtctcgg ctcaaagcag aatgctg 27

<210> SEQ ID NO 81
<211> LENGTH: 36
<212> TYPE: DNA
<213> ORGANISM: Artificial Sequence
<220> FEATURE:
<223> OTHER INFORMATION: primer

<400> SEQUENCE: 81
aaggtctcgg agcgtcataa ctgtagaaat gattcc 36

<210> SEQ ID NO 82
<211> LENGTH: 28
<212> TYPE: DNA
<213> ORGANISM: Artificial Sequence
<220> FEATURE:

-continued

<223> OTHER INFORMATION: primer

<400> SEQUENCE: 82
gggtctcggc tctgacaaca tcagcaag 28

<210> SEQ ID NO 83
<211> LENGTH: 40
<212> TYPE: DNA
<213> ORGANISM: Artificial Sequence
<220> FEATURE:
<223> OTHER INFORMATION: primer

<400> SEQUENCE: 83
agggtctcgg ctcactgagg aaatatatag acaaattaag 40

<210> SEQ ID NO 84
<211> LENGTH: 35
<212> TYPE: DNA
<213> ORGANISM: Artificial Sequence
<220> FEATURE:
<223> OTHER INFORMATION: primer

<400> SEQUENCE: 84
aaggtctcgg agcgtcactg gattttggtt ttagg 35

<210> SEQ ID NO 85
<211> LENGTH: 35
<212> TYPE: DNA
<213> ORGANISM: Artificial Sequence
<220> FEATURE:
<223> OTHER INFORMATION: primer

<400> SEQUENCE: 85
aaggtctcag agctcccaaa ggaaactatg tgtac 35

<210> SEQ ID NO 86
<211> LENGTH: 31
<212> TYPE: DNA
<213> ORGANISM: Artificial Sequence
<220> FEATURE:
<223> OTHER INFORMATION: primer

<400> SEQUENCE: 86
agggtctcgg ctcagatcgt tcaaacattt g 31

<210> SEQ ID NO 87
<211> LENGTH: 31
<212> TYPE: DNA
<213> ORGANISM: Artificial Sequence
<220> FEATURE:
<223> OTHER INFORMATION: primer

<400> SEQUENCE: 87
gaggtctcag ctcgtaccct gcaatgtgac c 31

<210> SEQ ID NO 88
<211> LENGTH: 27
<212> TYPE: DNA
<213> ORGANISM: Artificial Sequence
<220> FEATURE:
<223> OTHER INFORMATION: primer

<400> SEQUENCE: 88
agggtctcgg ctcatacagc attccca 27

<210> SEQ ID NO 89
<211> LENGTH: 28
<212> TYPE: DNA
<213> ORGANISM: Artificial Sequence
<220> FEATURE:
<223> OTHER INFORMATION: primer

<400> SEQUENCE: 89
ccgagctctg acaacatcag caagaacg 28

<210> SEQ ID NO 90
<211> LENGTH: 29
<212> TYPE: DNA
<213> ORGANISM: Artificial Sequence
<220> FEATURE:
<223> OTHER INFORMATION: primer

<400> SEQUENCE: 90
aagaattcaa aggaaaccca taagatgcg 29

<210> SEQ ID NO 91
<211> LENGTH: 47
<212> TYPE: DNA
<213> ORGANISM: Artificial Sequence
<220> FEATURE:
<223> OTHER INFORMATION: primer

<400> SEQUENCE: 91
tcgagctcac tgaggaaata tatagacaaa ttaagtttgg ttctatg 47

<210> SEQ ID NO 92
<211> LENGTH: 35
<212> TYPE: DNA
<213> ORGANISM: Artificial Sequence
<220> FEATURE:
<223> OTHER INFORMATION: primer

<400> SEQUENCE: 92
gtgaattcgc tcccaaagga aactatgtgt acttc 35

<210> SEQ ID NO 93
<211> LENGTH: 33
<212> TYPE: DNA
<213> ORGANISM: Artificial Sequence
<220> FEATURE:
<223> OTHER INFORMATION: primer

<400> SEQUENCE: 93
gcgagctcat acagcattcc cagaaagaga aac 33

<210> SEQ ID NO 94
<211> LENGTH: 30
<212> TYPE: DNA
<213> ORGANISM: Artificial Sequence
<220> FEATURE:
<223> OTHER INFORMATION: primer

<400> SEQUENCE: 94
tagaattcat gctagcttgt ttacacctcg 30

<210> SEQ ID NO 95
<211> LENGTH: 35
<212> TYPE: DNA
<213> ORGANISM: Artificial Sequence
<220> FEATURE:
<223> OTHER INFORMATION: primer

<400> SEQUENCE: 95
gagagctcgg agaacgcctt attattgtat atggc 35

<210> SEQ ID NO 96
<211> LENGTH: 29
<212> TYPE: DNA
<213> ORGANISM: Artificial Sequence
<220> FEATURE:
<223> OTHER INFORMATION: primer

<400> SEQUENCE: 96
aagaattcgc tcatcactgc acttcaagc 29

<210> SEQ ID NO 97
<211> LENGTH: 39
<212> TYPE: DNA
<213> ORGANISM: Artificial Sequence
<220> FEATURE:
<223> OTHER INFORMATION: primer

<400> SEQUENCE: 97
tagagctcat atgaagatga agatgaaata tttggtgtg 39

<210> SEQ ID NO 98
<211> LENGTH: 40
<212> TYPE: DNA
<213> ORGANISM: Artificial Sequence
<220> FEATURE:
<223> OTHER INFORMATION: primer

<400> SEQUENCE: 98
atgaattcct tatctttaat catattccat agtccatacc 40

<210> SEQ ID NO 99
<211> LENGTH: 45
<212> TYPE: DNA
<213> ORGANISM: Artificial Sequence
<220> FEATURE:
<223> OTHER INFORMATION: primer

<400> SEQUENCE: 99
aaggtctcgg agccttatct ttaatcatat tccatagtcc atacc 45

<210> SEQ ID NO 100
<211> LENGTH: 32
<212> TYPE: DNA
<213> ORGANISM: Artificial Sequence
<220> FEATURE:
<223> OTHER INFORMATION: primer

<400> SEQUENCE: 100
agcgagctct aataggttgc cagtctgatt tc 32

<210> SEQ ID NO 101
<211> LENGTH: 26
<212> TYPE: DNA
<213> ORGANISM: Artificial Sequence
<220> FEATURE:
<223> OTHER INFORMATION: primer

<400> SEQUENCE: 101
ctagaattct tgccatcgtt ttgtgg 26

<210> SEQ ID NO 102
<211> LENGTH: 26

<212> TYPE: DNA
<213> ORGANISM: Artificial Sequence
<220> FEATURE:
<223> OTHER INFORMATION: primer

<400> SEQUENCE: 102
tcggagctct gaacgtgcct ctcctc 26

<210> SEQ ID NO 103
<211> LENGTH: 44
<212> TYPE: DNA
<213> ORGANISM: Artificial Sequence
<220> FEATURE:
<223> OTHER INFORMATION: primer

<400> SEQUENCE: 103
aaggagctct aaaatgatta ttttatgaat atatttcatt gtgc 44

<210> SEQ ID NO 104
<211> LENGTH: 28
<212> TYPE: DNA
<213> ORGANISM: Artificial Sequence
<220> FEATURE:
<223> OTHER INFORMATION: primer

<400> SEQUENCE: 104
aatgaattcg aaccccaatt actggagc 28

<210> SEQ ID NO 105
<211> LENGTH: 25
<212> TYPE: DNA
<213> ORGANISM: Artificial Sequence
<220> FEATURE:
<223> OTHER INFORMATION: primer

<400> SEQUENCE: 105
gcggtctcgg catggtggag cacga 25

<210> SEQ ID NO 106
<211> LENGTH: 31
<212> TYPE: DNA
<213> ORGANISM: Artificial Sequence
<220> FEATURE:
<223> OTHER INFORMATION: primer

<400> SEQUENCE: 106
agggtctcgg ctcagatcgt tcaaacattt g 31

<210> SEQ ID NO 107
<211> LENGTH: 36
<212> TYPE: DNA
<213> ORGANISM: Artificial Sequence
<220> FEATURE:
<223> OTHER INFORMATION: primer

<400> SEQUENCE: 107
attgtacaag taattgcttt catagatccg tcttcc 36

<210> SEQ ID NO 108
<211> LENGTH: 31
<212> TYPE: DNA
<213> ORGANISM: Artificial Sequence
<220> FEATURE:
<223> OTHER INFORMATION: primer

<400> SEQUENCE: 108
tagagctcgg gttcctagag agatctctag g 31

<210> SEQ ID NO 109
<211> LENGTH: 47
<212> TYPE: DNA
<213> ORGANISM: Artificial Sequence
<220> FEATURE:
<223> OTHER INFORMATION: primer

<400> SEQUENCE: 109
tatgtacaag taaggtagtc aagatgcata ataaataacg gattgtg 47

<210> SEQ ID NO 110
<211> LENGTH: 28
<212> TYPE: DNA
<213> ORGANISM: Artificial Sequence
<220> FEATURE:
<223> OTHER INFORMATION: primer

<400> SEQUENCE: 110
tagagctctg ggcccctacc gggggtaa 28

<210> SEQ ID NO 111
<211> LENGTH: 29
<212> TYPE: DNA
<213> ORGANISM: Artificial Sequence
<220> FEATURE:
<223> OTHER INFORMATION: primer

<400> SEQUENCE: 111
attgtacaag taaggcttcg cttcccgcc 29

<210> SEQ ID NO 112
<211> LENGTH: 23
<212> TYPE: DNA
<213> ORGANISM: Artificial Sequence
<220> FEATURE:
<223> OTHER INFORMATION: primer

<400> SEQUENCE: 112
aaggtaccag tgaagacaac acc 23

<210> SEQ ID NO 113
<211> LENGTH: 23
<212> TYPE: DNA
<213> ORGANISM: Artificial Sequence
<220> FEATURE:
<223> OTHER INFORMATION: primer

<400> SEQUENCE: 113
atgagctcgg gttgccgaac tgc 23

<210> SEQ ID NO 114
<211> LENGTH: 377
<212> TYPE: DNA
<213> ORGANISM: Artificial Sequence
<220> FEATURE:
<223> OTHER INFORMATION: NbHSPb

<400> SEQUENCE: 114
gagctcactg aggaaatata tagacaaatt aagtttggtt ctatgagttc taatttggac 60
ttaagagttg tttgaaattc tattttatag tgatgcttat aatgtatttg gactgttttc 120
tgctgtgtgt aagacctttt ggtctgtgaa ctggaaacat acatgaataa atttctttga 180
atttactgga atttttgcat caacaaaaga aaaattgaag ttactaactt gtaaatggaa 240
caattgtaat gttaaaggat ataaatatct taatatagtg cgatacgaat cacacgaatg 300
caagactttc tctctctgct cccgctcatg ctctcggtgc atgttagcta aatatacatc 360
ggtgcatcca tgaattc 377

<210> SEQ ID NO 115
<211> LENGTH: 14115
<212> TYPE: DNA
<213> ORGANISM: Artificial Sequence
<220> FEATURE:
<223> OTHER INFORMATION: pBYR2eAK2Mc-GFP

<400> SEQUENCE: 115
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620
cgtcagtgga gatatcacat caatccactt gctttgaaga cgtggttgga acgtcttctt 1680
tttccacgat gctcctcgtg ggtgggggtc catctttggg accactgtcg gcagaggcat 1740
cttcaacgat ggcctttcct ttatcgcaat gatggcattt gtaggagcca ccttcctttt 1800
ccactatctt cacaataaag tgacagatag ctgggcaatg gaatccgagg aggtttccgg 1860

-continued

```
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggcc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat ggtgagcaag ggcgaggagc   3420
tgttcaccgg ggtggtgccc atcctggtcg agctggacgg cgacgtaaac ggccacaagt   3480
tcagcgtgtc cggcgagggc gagggcgatg ccacctacgg caagctgacc ctgaagttca   3540
tctgcaccac cggcaagctg cccgtgccct ggcccaccct cgtgaccacc ttcagctacg   3600
gcgtgcagtg cttcagccgc taccccgacc acatgaagca gcacgacttc ttcaagtccg   3660
ccatgcccga aggctacgtc caggagcgca ccatcttctt caaggacgac ggcaactaca   3720
agacccgcgc cgaggtgaag ttcgagggcg acaccctggt gaaccgcatc gagctgaagg   3780
gcatcgactt caaggaggac ggcaacatcc tggggcacaa gctggagtac aactacaaca   3840
gccacaacgt ctatatcatg gccgacaagc agaagaacgg catcaaggtg aacttcaaga   3900
tccgccacaa catcgaggac ggcagcgtgc agctcgccga ccactaccag cagaacaccc   3960
ccatcggcga cggccccgtg ctgctgcccg acaaccacta cctgagcacc cagtccgccc   4020
tgagcaaaga ccccaacgag aagcgcgatc acatggtcct gctggagttc gtgaccgccg   4080
ccgggatcac tcacggcatg gacgagctgt acaagtaaga gctcaaagca gaatgctgag   4140
ctaaaagaaa ggctttttcc attttcgaga gacaatgaga aaagaagaag aagaagaaga   4200
agaagaagaa gaagaaaaga gtaaataata aagccccaca ggaggcgaag ttcttgtagc   4260
```

-continued

```
tccatgttat ctaagttatt gatattgttt gccctatatt ttatttctgt cattgtgtat   4320
gttttgttca gtttcgatct ccttgcaaaa tgcagagatt atgagatgaa taaactaagt   4380
tatattatta tacgtgttaa tattctcctc ctctctctag ctagcctttt gttttctctt   4440
tttcttattt gattttcttt aaatcaatcc attttaggag agggccaggg agtgatccag   4500
caaaacatga agattagaag aaacttccct ctttttttc ctgaaaacaa tttaacgtcg    4560
agatttatct ctttttgtaa tggaatcatt tctacagtta tgacgctcat acagcattcc   4620
cagaaagaga aacagaagaa atatacaaac tttcattttg agagcagcac ctcgtctatt   4680
gattgcagat aatatgcttc tcatttgtat ttccttttga ttatttttgt ttctatccct   4740
ttgtttgagt caatctcaaa tattcggtca ttgttggtat gaaaaatcaa gcagttcatg   4800
ttaagagtca atttaaaatt aatattttta tatagagttg tatgtgaaat gatgttgtga   4860
tttggtatat atggataaag agcttgtcag ttcattttgg tctcattttt ttggtatcca   4920
aataagaaac acaaaaggga tatgtccctc tactatcaaa tattagttat aagtattcat   4980
gttatactat tcgatatttt ctaccccaat cgttacctat ttaaaagtat ttacccctcc   5040
atctatcaaa cccctggacc cagctttcct attacatgtg gcttcatctt aagcccccaa   5100
accttttct tatttttgat ttttaaaggc tcatcttaaa atttattact caaattaata    5160
cctcttaata acccacctca aggacccagt aattaaatat ccaattagct ccagtaattg   5220
gggttcatat tagctccagt cttaaatttt aaaggcgatg atcgtattcc tccacttggt   5280
tcatttatac tcaaagaata ctcaatgtct ttagtgttta gataactttt tgtaaatcat   5340
atagattgtt ttaacaaaaa acaattcaat agtagatttt cacatgaaag ttacataaaa   5400
attctttaaa attactttct caaaaaattg ttccaaacat attatcccac aattaaactc   5460
aatctgtttt tcgaaaccta aatcaaaacc aatccaacta ccttatataa tatataatca   5520
atacattgta aagaactgca tgttctttta aattttgggg gcaaagttat tccgtacgtt   5580
cacacatgta ctaataggag gtaataaatg atatgtgaaa caatcgaggt gtaaacaagc   5640
tagcatgaat tctcgattaa aaatcccaat tatatttggt ctaatttagt ttggtattga   5700
gtaaaacaaa ttcgaaccaa accaaaatat aaatatatag tttttatata tatgccttta   5760
agacttttta tagaattttc tttaaaaaat atctaggtac atcaacgaaa aattagtcaa   5820
acgactaaaa taaataaata tcatgtgtta ttaagaaaat tctcctataa gaatatttta   5880
atagatcata tgtttgtaaa aaaaattaat ttttactaac acatatattt acttatcaaa   5940
aatttgacaa agtaagatta aaataatatt catctaacaa aaaaaaaacc agaaaatgct   6000
gaaaacccgg caaaaccgaa ccaatccaaa ccgatatagt tggtttggtt tgattttgat   6060
ataaaccgaa ccaactcggt ccatttgcac ccctaatcat aatagcttta atatttcaag   6120
atattattaa gttaacgttg tcaatatcct ggaaattttg caaaatgaat caagcctata   6180
tggctgtaat atgaatttaa aagcagctcg atgtggtggt aatatgtaat ttacttgatt   6240
ctaaaaaaat atcccaagta ttaataattt ctgctaggaa gaaggttagc tacgatttac   6300
agcaaagcca gaatacaaag aaccataaag tgattgaagc tcgaaatata cgaaggaaca   6360
aatattttta aaaaaatacg caatgacttg gaacaaaaga aagtgatata ttttttgttc   6420
ttaaacaagc atcccctcta aagaatggca gttttccttt gcatgtaact attatgctcc   6480
cttcgttaca aaaattttgg actactattg ggaacttctt ctgaaaatag tggtaccgag   6540
tgtacttcaa gtcagttgga aatcaataaa atgattattt tatgaatata tttcattgtg   6600
```

```
caagtagata gaaattacat atgttacata acacacgaaa taaacaaaaa aacacaatcc   6660
aaaacaaaca ccccaaacaa aataacacta tatatatcct cgtatgagga gaggcacgtt   6720
cagtgactcg acgattcccg agcaaaaaaa gtctccccgt cacacatata gtgggtgacg   6780
caattatctt caaagtaatc cttctgttga cttgtcattg ataacatcca gtcttcgtca   6840
ggattgcaaa gaattataga agggatccca ccttttattt tcttcttttt tccatattta   6900
gggttgacag tgaaatcaga ctggcaacct attaattgct tccacaatgg gacgaacttg   6960
aaggggatgt cgtcgatgat attataggtg gcgtgttcat cgtagttggt gaagtcgatg   7020
gtcccgttcc agtagttgtg tcgcccgaga cttctagccc aggtggtctt tccggtacga   7080
gttggtccgc agatgtagag gctggggtgt ctgaccccag tccttccctc atcctggtta   7140
gatcggccat ccactcaagg tcagattgtg cttgatcgta ggagacagga tgtatgaaag   7200
tgtaggcatc gatgcttaca tgatataggt gcgtctctct ccagttgtgc agatcttcgt   7260
ggcagcggag atctgattct gtgaagggcg acacgtactg ctcaggttgt ggaggaaata   7320
atttgttggc tgaatattcc agccattgaa gctttgttgc ccattcatga gggaactctt   7380
ctttgatcat gtcaagatac tcctccttag acgttgcagt ctggataata gttcgccatc   7440
gtgcgtcaga tttgcgagga gacaccttat gatctcggaa atctcctctg gttttaatat   7500
ctccgtcctt tgatatgtaa tcaaggactt gtttagagtt tctagctggc tggatattag   7560
ggtgatttcc ttcaaaatcg aaaaaagaag gatccctaat acaaggtttt ttatcaagct   7620
ggataagagc atgatagtgg gtagtgccat cttgatgaag ctcagaagca acaccaagga   7680
agaaaataag aaaaggtgtg agtttctccc agagaaactg gaataaatca tctctttgag   7740
atgagcactt ggggtaggta aggaaaacat atttagattg gagtctgaag ttcttgctag   7800
cagaaggcat gttgttgtga ctccgagggg ttgcctcaaa ctctatctta taaccggcgt   7860
ggaggcatgg aggcaagggc attttggtaa tttaagtagt tagtggaaaa tgacgtcatt   7920
tacttaaaga cgaagtcttg cgacaagggg ggcccacgcc gaattttaat attaccggcg   7980
tggccccacc ttatcgcgag tgctttagca cgagcggtcc agatttaaag tagaaaagtt   8040
cccgcccact agggttaaag gtgttcacac tataaaagca tatacgatgt gatggtattt   8100
gatggagcgt atattgtatc aggtatttcc gtcggatacg aattattcgt acggccggac   8160
cggtccccta ggccggccaa ttcgagatcg gccgcggctg agtggctcct tcaatcgttg   8220
cggttctgtc agttccaaac gtaaaacggc ttgtcccgcg tcatcggcgg gggtcataac   8280
gtgactccct taattctccg ctcatgatca gattgtcgtt tcccgccttc agtttaaact   8340
atcagtgttt gacaggatat attggcgggt aaacctaaga gaaaagagcg tttattagaa   8400
taatcggata tttaaaaggg cgtgaaaagg tttatccgtt cgtccatttg tatgtgcatg   8460
ccaaccacag ggttccccag atctggcgcc ggccagcgag acgagcaaga ttggccgccg   8520
cccgaaacga tccgacagcg cgcccagcac aggtgcgcag gcaaattgca ccaacgcata   8580
cagcgccagc agaatgccat agtgggcggt gacgtcgttc gagtgaacca gatcgcgcag   8640
gaggcccggc agcaccggca taatcaggcc gatgccgaca gcgtcgagcg cgacagtgct   8700
cagaattacg atcaggggta tgttgggttt cacgtctggc ctccggagac tgtcatacgc   8760
gtaaaaaggc cgcgttgctg gcgttttttcc ataggctccg cccccctgac gagcatcaca   8820
aaaatcgacg ctcaagtcag aggtggcgaa acccgacagg actataaaga taccaggcgt   8880
ttccccctgg aagctccctc gtgcgctctc ctgttccgac cctgccgctt accggatacc   8940
tgtccgcctt tctcccttcg ggaagcgtgg cgctttctca tagctcacgc tgtaggtatc   9000
```

tcagttcggt gtaggtcgtt cgctccaagc tgggctgtgt gcacgaaccc cccgttcagc 9060
ccgaccgctg cgccttatcc ggtaactatc gtcttgagtc caacccggta agacacgact 9120
tatcgccact ggcagcagcc actggtaaca ggattagcag agcgaggtat gtaggcggtg 9180
ctacagagtt cttgaagtgg tggcctaact acggctacac tagaaggaca gtatttggta 9240
tctgcgctct gctgaagcca gttaccttcg gaaaaagagt tggtagctct tgatccggca 9300
aacaaaccac cgctggtagc ggtggttttt ttgtttgcaa gcagcagatt acgcgcagaa 9360
aaaaaggatc tcaagaagat cctttgatct tttctacggg gtctgacgct cagtggaacg 9420
aaaactcacg ttaagggatt ttggtcatga gattatcaaa aaggatcttc acctagatcc 9480
ttttaaatta aaaatgaagt tttaaatcaa tctaaagtat atatgagtaa acttggtctg 9540
cagttgccat gttttacggc agtgagagca gagatagcgc tgatgtccgg cggtgctttt 9600
gccgttacgc accaccccgt cagtagctga acaggaggga cagctgatag acacagaagc 9660
cactggagca cctcaaaaac accatcatac actaaatcag taagttggca gcatcaccca 9720
taattgtggt ttcaaaatcg gctccgtcga tactatgtta tacgccaact ttgaaaacaa 9780
ctttgaaaaa gctgttttct ggtatttaag gttttagaat gcaaggaaca gtgaattgga 9840
gttcgtcttg ttataattag cttcttgggg tatctttaaa tactgtagaa aagaggaagg 9900
aaataataaa tggctaaaat gagaatatca ccggaattga aaaaactgat cgaaaaatac 9960
cgctgcgtaa aagatacgga aggaatgtct cctgctaagg tatataagct ggtgggagaa 10020
aatgaaaacc tatatttaaa aatgacggac agccggtata aagggaccac ctatgatgtg 10080
gaacgggaaa aggacatgat gctatggctg gaaggaaagc tgcctgttcc aaaggtcctg 10140
cactttgaac ggcatgatgg ctggagcaat ctgctcatga gtgaggccga tggcgtcctt 10200
tgctcggaag agtatgaaga tgaacaaagc cctgaaaaga ttatcgagct gtatgcggag 10260
tgcatcaggc tctttcactc catcgacata tcggattgtc cctatacgaa tagcttagac 10320
agccgcttag ccgaattgga ttacttactg aataacgatc tggccgatgt ggattgcgaa 10380
aactgggaag aagacactcc atttaaagat ccgcgcgagc tgtatgattt tttaaagacg 10440
gaaaagcccg aagaggaact tgtcttttcc cacggcgacc tgggagacag caacatcttt 10500
gtgaaagatg gcaaagtaag tggctttatt gatcttggga gaagcggcag ggcggacaag 10560
tggtatgaca ttgccttctg cgtccggtcg atcagggagg atatcgggga agaacagtat 10620
gtcgagctat tttttgactt actggggatc aagcctgatt gggagaaaat aaaatattat 10680
attttactgg atgaattgtt ttagtaccta gatgtggcgc aacgatgccg gcgacaagca 10740
ggagcgcacc gacttcttcc gcatcaagtg ttttggctct caggccgagg cccacggcaa 10800
gtatttgggc aaggggtcgc tggtattcgt gcagggcaag attcggaata ccaagtacga 10860
gaaggacggc cagacggtct acgggaccga cttcattgcc gataaggtgg attatctgga 10920
caccaaggca ccaggcgggt caaatcagga ataagggcac attgccccgg cgtgagtcgg 10980
ggcaatcccg caaggagggt gaatgaatcg gacgtttgac cggaaggcat acaggcaaga 11040
actgatcgac gcggggtttt ccgccgagga tgccgaaacc atcgcaagcc gcaccgtcat 11100
gcgtgcgccc cgcgaaacct tccagtccgt cggctcgatg gtccagcaag ctacggccaa 11160
gatcgagcgc gacagcgtgc aactggctcc ccctgccctg cccgcgccat cggccgccgt 11220
ggagcgttcg cgtcgtctcg aacaggaggc ggcaggtttg gcgaagtcga tgaccatcga 11280
cacgcgagga actatgacga ccaagaagcg aaaaaccgcc ggcgaggacc tggcaaaaca 11340

-continued

```
ggtcagcgag gccaagcagg ccgcgttgct gaaacacacg aagcagcaga tcaaggaaat  11400
gcagctttcc ttgttcgata ttgcgccgtg gccggacacg atgcgagcga tgccaaacga  11460
cacggcccgc tctgccctgt tcaccacgcg caacaagaaa atcccgcgcg aggcgctgca  11520
aaacaaggtc attttccacg tcaacaagga cgtgaagatc acctacaccg gcgtcgagct  11580
gcgggccgac gatgacgaac tggtgtggca gcaggtgttg gagtacgcga agcgcacccc  11640
tatcggcgag ccgatcacct tcacgttcta cgagctttgc caggacctgg gctggtcgat  11700
caatggccgg tattacacga aggccgagga atgcctgtcg cgcctacagg cgacggcgat  11760
gggcttcacg tccgaccgcg ttgggcacct ggaatcggtg tcgctgctgc accgcttccg  11820
cgtcctggac cgtggcaaga aaacgtcccg ttgccaggtc ctgatcgacg aggaaatcgt  11880
cgtgctgttt gctggcgacc actacacgaa attcatatgg gagaagtacc gcaagctgtc  11940
gccgacggcc cgacggatgt tcgactattt cagctcgcac cgggagccgt acccgctcaa  12000
gctggaaacc ttccgcctca tgtgcggatc ggattccacc cgcgtgaaga agtggcgcga  12060
gcaggtcggc gaagcctgcg aagagttgcg aggcagcggc ctggtggaac acgcctgggt  12120
caatgatgac ctggtgcatt gcaaacgcta gggccttgtg gggtcagttc cggctggggg  12180
ttcagcagcc agcgctttac tggcatttca ggaacaagcg ggcactgctc gacgcacttg  12240
cttcgctcag tatcgctcgg gacgcacggc gcgctctacg aactgccgat aaacagagga  12300
ttaaaattga caattcaatg gcaaggactg ccagcgctgc catttttggg gtgaggccgt  12360
tcgcggccga ggggcgcagc ccctgggggg atgggaggcc cgcgttagcg ggccgggagg  12420
gttcgagaag ggggggcacc ccccttcggc gtgcgcggtc acgcgcacag ggcgcagccc  12480
tggttaaaaa caaggtttat aaatattggt ttaaaagcag gttaaaagac aggttagcgg  12540
tggccgaaaa acgggcggaa acccttgcaa atgctggatt ttctgcctgt ggacagcccc  12600
tcaaatgtca ataggtgcgc ccctcatctg tcagcactct gcccctcaag tgtcaaggat  12660
cgcgcccctc atctgtcagt agtcgcgccc ctcaagtgtc aataccgcag ggcacttatc  12720
cccaggcttg tccacatcat ctgtgggaaa ctcgcgtaaa atcaggcgtt ttcgccgatt  12780
tgcgaggctg gccagctcca cgtcgccggc cgaaatcgag cctgcccctc atctgtcaac  12840
gccgcgccgg gtgagtcggc ccctcaagtg tcaacgtccg cccctcatct gtcagtgagg  12900
gccaagtttt ccgcgaggta tccacaacgc cggcggccgc ggtgtctcgc acacggcttc  12960
gacggcgttt ctggcgcgtt tgcagggcca tagacggccg ccagcccagc ggcgagggca  13020
accagcccgg tgagcgtcgc aaaggcgctc ggtcttgcct tgctcgtcga gatctggggt  13080
cgatcagccg gggatgcatc aggccgacag tcggaacttc gggtccccga cctgtaccat  13140
tcggtgagca atggataggg gagttgatat cgtcaacgtt cacttctaaa gaaatagcgc  13200
cactcagctt cctcagcggc tttatccagc gatttcctat tatgtcggca tagttctcaa  13260
gatcgacagc ctgtcacggt taagcgagaa atgaataaga aggctgataa ttcggatctc  13320
tgcgagggag atgatatttg atcacaggca gcaacgctct gtcatcgtta caatcaacat  13380
gctaccctcc gcgagatcat ccgtgtttca aacccggcag cttagttgcc gttcttccga  13440
atagcatcgg taacatgagc aaagtctgcc gccttacaac ggctctcccg ctgacgccgt  13500
cccggactga tgggctgcct gtatcgagtg gtgattttgt gccgagctgc cggtcgggga  13560
gctgttggct ggctggtggc aggatatatt gtggtgtaaa caaattgacg cttagacaac  13620
ttaataacac attgcggacg tttttaatgt actggggtgg tttttctttt caccagtgag  13680
acgggcaaca gctgattgcc cttcaccgcc tggccctgag agagttgcag caagcggtcc  13740
```

-continued acgctggttt gccccagcag gcgaaaatcc tgtttgatgg tggttccgaa atcggcaaaa 13800
tcccttataa atcaaaagaa tagcccgaga tagggttgag tgttgttcca gtttggaaca 13860
agagtccact attaaagaac gtggactcca acgtcaaagg gcgaaaaacc gtctatcagg 13920
gcgatggccc actacgtgaa ccatcaccca aatcaagttt tttggggtcg aggtgccgta 13980
aagcactaaa tcggaaccct aaagggagcc cccgatttag agcttgacgg ggaaagccgg 14040
cgaacgtggc gagaaaggaa gggaagaaag cgaaaggagc gggcgccatt caggctgcgc 14100
aactgttggg aaggg 14115

<210> SEQ ID NO 116
<211> LENGTH: 17111
<212> TYPE: DNA
<213> ORGANISM: Artificial Sequence
<220> FEATURE:
<223> OTHER INFORMATION: pBY11HA-GFP

<400> SEQUENCE: 116
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780
tggatgatct ctttctctta ttcagataat tagtaattac acataacaca caactttgat 840
gcccacatta tagtgattag catgtcacta tgtgtgcatc cttttatttc atacattaat 900
taacttggcc aatccagaag atggacaagt ctagggtcac attgcagggt actctagctt 960
actcgccttc tttttcgaag gtttgagtac cttcagggca tcctcttgat acattacttt 1020
ccacttcgat tggggcaagc tgtagcagtt cttgcttaga ccgaattgcc atctcacaga 1080
gatgctgaag agttcgcgac cctccagaaa cggtgatact aactcctcga aaccgaatac 1140
tataggtaca tccgatctgg tcgaaaccga aaaatcgaga tgctgcatag ttaaccgaat 1200
ctcccgtcca agatccaagg actctgtgca gtgaagcttc cgtcctgtcg tatctgagat 1260
atctcttaaa tacaactttc ccgaaacccc agctttcctt gaaaccaagg ggattatctt 1320
gattcgaatt cgtctcatcg ttatgtagcc gccactcagt ccaactcgga ctttcgtcag 1380
gaagtttgaa gggagaagtt gtacctcctg atcctccatc ccaacgttca ctgttagctt 1440
gttccctagc gtcgtttcct tgtatagctc gttccatgga ttgtaaatag taattgtaat 1500
gttgtttgtt gtttgttgtt gttggtaatt gttgtaaaaa tacgctctcc aaatgaaatg 1560
aacttcctta tatagaggaa gggtcttgcg aaggatagtg ggattgtgcg tcatccctta 1620

-continued

```
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca aggggggccc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagcgagac caacaacggt ctctagctaa   3420
agcagaatgc tgagctaaaa gaaaggcttt ttccattttc gagagacaat gagaaaagaa   3480
gaagaagaag aagaagaaga agaagaagaa aagagtaaat aataaagccc cacaggaggc   3540
gaagttcttg tagctccatg ttatctaagt tattgatatt gtttgcccta tattttattt   3600
ctgtcattgt gtatgttttg ttcagtttcg atctccttgc aaaatgcaga gattatgaga   3660
tgaataaact aagttatatt attatacgtg ttaatattct cctcctctct ctagctagcc   3720
ttttgttttc tctttttctt atttgatttt ctttaaatca atccatttta ggagagggcc   3780
agggagtgat ccagcaaaac atgaagatta gaagaaactt ccctcttttt tttcctgaaa   3840
acaatttaac gtcgagattt atctcttttt gtaatggaat catttctaca gttatgacgg   3900
ctcactgagg aaatatatag acaaattaag tttggttcta tgagttctaa tttggactta   3960
agagttgttt gaaattctat tttatagtga tgcttataat gtatttggac tgttttctgc   4020
```

```
tgtgtgtaag accttttggt ctgtgaactg gaaacataca tgaataaatt tctttgaatt   4080
tactggaatt tttgcatcaa caaaagaaaa attgaagtta ctaacttgta aatggaacaa   4140
ttgtaatgtt aaaggatata aatatcttaa tatagtgcga tacgaatcac acgaatgcaa   4200
gactttctct ctctgctccc gctcatgctc tcggtgcatg ttagctaaat atacatcggt   4260
gcatccatgg caggagcatg aggacgggga tgaggaaggg agtgaggagg gccaaaagaa   4320
gtacacatag tttcctttgg gagcgaattc tcgattaaaa atcccaatta tatttggtct   4380
aatttagttt ggtattgagt aaaacaaatt cgaaccaaac caaaatataa atatatagtt   4440
tttatatata tgcctttaag actttttata gaattttctt taaaaaatat ctaggtacat   4500
caacgaaaaa ttagtcaaac gactaaaata aataaatatc atgtgttatt aagaaaattc   4560
tcctataaga atattttaat agatcatatg tttgtaaaaa aaattaattt ttactaacac   4620
atatatttac ttatcaaaaa tttgacaaag taagattaaa ataatattca tctaacaaaa   4680
aaaaaaccag aaaatgctga aaacccggca aaaccgaacc aatccaaacc gatatagttg   4740
gtttggtttg attttgatat aaaccgaacc aactcggtcc atttgcaccc ctaatcataa   4800
tagctttaat atttcaagat attattaagt taacgttgtc aatatcctgg aaattttgca   4860
aaatgaatca agcctatatg gctgtaatat gaatttaaaa gcagctcgat gtggtggtaa   4920
tatgtaattt acttgattct aaaaaaatat cccaagtatt aataatttct gctaggaaga   4980
aggttagcta cgatttacag caaagccaga atacaaagaa ccataaagtg attgaagctc   5040
gaaatatacg aaggaacaaa tatttttaaa aaaatacgca atgacttgga acaaaagaaa   5100
gtgatatatt ttttgttctt aaacaagcat cccctctaaa gaatggcagt tttcctttgc   5160
atgtaactat tatgctccct tcgttacaaa aattttggac tactattggg aacttcttct   5220
gaaaatagtg gtaccgagtg tacttcaagt cagttggaaa tcaataaaat gattatttta   5280
tgaatatatt tcattgtgca agtagataga aattacatat gttacataac acacgaaata   5340
aacaaaaaaa cacaatccaa aacaaacacc ccaaacaaaa taacactata tatatcctcg   5400
tatgaggaga ggcacgttca gtgactcgac gattcccgag caaaaaaagt ctccccgtca   5460
cacatatagt gggtgacgca attatcttca aagtaatcct tctgttgact tgtcattgat   5520
aacatccagt cttcgtcagg attccaaaga attatagaag ggatcggtca acatggtgga   5580
gcacgacaca cttgtctact ccaaaaatat caaagataca gtctcagaag accaaagggc   5640
aattgagact tttcaacaaa gggtaatatc cggaaacctc ctcggattcc attgcccagc   5700
tatctgtcac tttattgtga agatagtgga aaaggaaggt ggctcctaca aatgccatca   5760
ttgcgataaa ggaaaggcca tcgttgaaga tgcctctgcc gacagtggtc ccaaagatgg   5820
acccccaccc acgaggagca tcgtggaaaa agaagacgtt ccaaccacgt cttcaaagca   5880
agtggattga tgtgataaca tggtggagca cgacacactt gtctactcca aaaatatcaa   5940
agatacagtc tcagaagacc aaagggcaat tgagactttt caacaaaggg taatatccgg   6000
aaacctcctc ggattccatt gcccagctat ctgtcacttt attgtgaaga tagtggaaaa   6060
ggaaggtggc tcctacaaat gccatcattg cgataaagga aaggccatcg ttgaagatgc   6120
ctctgccgac agtggtccca aagatggacc cccacccacg aggagcatcg tggaaaaaga   6180
agacgttcca accacgtctt caaagcaagt ggattgatgt gatatctcca ctgacgtaag   6240
ggatgacgca caatcccact atccttcgca agacccttcc tctatataag gaagttcatt   6300
tcatttggag aggacctcga gaaacaaaca aaatcaacaa atatagaaaa taacgcattt   6360
```

-continued

```
ccaattcttt gaaatttctg caacatctag aacaatggtg agcaagggcg aggagctgtt   6420
caccggggtg gtgcccatcc tggtcgagct ggacggcgac gtaaacggcc acaagttcag   6480
cgtgtccggc gagggcgagg gcgatgccac ctacggcaag ctgaccctga agttcatctg   6540
caccaccggc aagctgcccg tgccctggcc caccctcgtg accaccttca gctacggcgt   6600
gcagtgcttc agccgctacc ccgaccacat gaagcagcac gacttcttca agtccgccat   6660
gcccgaaggc tacgtccagg agcgcaccat cttcttcaag gacgacggca actacaagac   6720
ccgcgccgag gtgaagttcg agggcgacac cctggtgaac cgcatcgagc tgaagggcat   6780
cgacttcaag gaggacggca acatcctggg gcacaagctg gagtacaact acaacagcca   6840
caacgtctat atcatggccg acaagcagaa gaacggcatc aaggtgaact tcaagatccg   6900
ccacaacatc gaggacggca gcgtgcagct cgccgaccac taccagcaga acacccccat   6960
cggcgacggc cccgtgctgc tgcccgacaa ccactacctg agcacccagt ccgccctgag   7020
caaagacccc aacgagaagc gcgatcacat ggtcctgctg gagttcgtga ccgccgccgg   7080
gatcactcac ggcatggacg agctgtacaa gtaagagctc aaagcagaat gctgagctaa   7140
aagaaaggct tttccattt tcgagagaca atgagaaaag aagaagaaga agaagaagaa   7200
gaagaagaag aaaagagtaa ataataaagc cccacaggag gcgaagttct tgtagctcca   7260
tgttatctaa gttattgata ttgtttgccc tatattttat ttctgtcatt gtgtatgttt   7320
tgttcagttt cgatctcctt gcaaaatgca gagattatga gatgaataaa ctaagttata   7380
ttattatacg tgttaatatt ctcctcctct ctctagctag ccttttgttt tctcttttc    7440
ttatttgatt ttctttaaat caatccattt taggagaggg ccagggagtg atccagcaaa   7500
acatgaagat tagaagaaac ttccctcttt tttttcctga aaacaattta acgtcgagat   7560
ttatctcttt ttgtaatgga atcatttcta cagttatgac gctcatacag cattcccaga   7620
aagagaaaca gaagaaatat acaaactttc attttgagag cagcacctcg tctattgatt   7680
gcagataata tgcttctcat ttgtatttcc ttttgattat ttttgtttct atccctttgt   7740
ttgagtcaat ctcaaatatt cggtcattgt tggtatgaaa aatcaagcag ttcatgttaa   7800
gagtcaattt aaaattaata tttttatata gagttgtatg tgaaatgatg ttgtgatttg   7860
gtatatatgg ataaagagct tgtcagttca ttttggtctg atttttttgg tatccaaata   7920
agaaacacaa aagggatatg tccctctact atcaaatatt agttataagt attcatgtta   7980
tactattcga tattttctac cccaatcgtt acctatttaa aagtatttac ccctccatct   8040
atcaaacccc tggacccagc tttcctatta catgtggctt catcttaagc ccccaaacct   8100
ttttcttatt tttgattttt aaaggctcat cttaaaattt attactcaaa ttaatacctc   8160
ttaataaccc acctcaagga cccagtaatt aaatatccaa ttagctccag taattggggt   8220
tcatattagc tccagtctta aattttaaag gcgatgatcg tattcctcca cttggttcat   8280
ttatactcaa agaatactca atgtctttag tgtttagata actttttgta aatcatatag   8340
attgttttaa caaaaaacaa ttcaatagta gattttcaca tgaaagttac ataaaaattc   8400
tttaaaatta ctttctcaaa aaattgttcc aaacatatta tcccacaatt aaactcaatc   8460
tgtttttcga aacctaaatc aaaaccaatc caactacctt atataatata taatcaatac   8520
attgtaaaga actgcatgtt cttttaaatt ttgggggcaa agttattccg tacgttcaca   8580
catgtactaa taggaggtaa taaatgatat gtgaaacaat cgaggtgtaa acaagctagc   8640
atgaattctc gattaaaaat cccaattata tttggtctaa tttagtttgg tattgagtaa   8700
aacaaattcg aaccaaacca aaatataaat atatagtttt tatatatatg cctttaagac   8760
```

```
tttttataga attttcttta aaaaatatct aggtacatca acgaaaaatt agtcaaacga   8820
ctaaaataaa taaatatcat gtgttattaa gaaaattctc ctataagaat attttaatag   8880
atcatatgtt tgtaaaaaaa attaattttt actaacacat atatttactt atcaaaaatt   8940
tgacaaagta agattaaaat aatattcatc taacaaaaaa aaaaccagaa aatgctgaaa   9000
acccggcaaa accgaaccaa tccaaaccga tatagttggt ttggtttgat tttgatataa   9060
accgaaccaa ctcggtccat ttgcacccct aatcataata gctttaatat ttcaagatat   9120
tattaagtta acgttgtcaa tatcctggaa attttgcaaa atgaatcaag cctatatggc   9180
tgtaatatga atttaaaagc agctcgatgt ggtggtaata tgtaatttac ttgattctaa   9240
aaaaatatcc caagtattaa taatttctgc taggaagaag gttagctacg atttacagca   9300
aagccagaat acaaagaacc ataaagtgat tgaagctcga aatatacgaa ggaacaaata   9360
tttttaaaaa aatacgcaat gacttggaac aaaagaaagt gatatatttt ttgttcttaa   9420
acaagcatcc cctctaaaga atggcagttt tcctttgcat gtaactatta tgctcccttc   9480
gttacaaaaa ttttggacta ctattgggaa cttcttctga aaatagtggt accgagtgta   9540
cttcaagtca gttggaaatc aataaaatga ttattttatg aatatatttc attgtgcaag   9600
tagatagaaa ttacatatgt tacataacac acgaaataaa caaaaaaaca caatccaaaa   9660
caaacacccc aaacaaaata acactatata tatcctcgta tgaggagagg cacgttcagt   9720
gactcgacga ttcccgagca aaaaaagtct ccccgtcaca catatagtgg gtgacgcaat   9780
tatcttcaaa gtaatccttc tgttgacttg tcattgataa catccagtct tcgtcaggat   9840
tgcaaagaat tatagaaggg attccacctt ttattttctt ctttttttcca tatttagggt   9900
tgacagtgaa atcagactgg caacctatta attgcttcca caatgggacg aacttgaagg   9960
ggatgtcgtc gatgatatta taggtggcgt gttcatcgta gttggtgaag tcgatggtcc  10020
cgttccagta gttgtgtcgc ccgagacttc tagcccaggt ggtctttccg gtacgagttg  10080
gtccgcagat gtagaggctg gggtgtctga ccccagtcct tccctcatcc tggttagatc  10140
ggccatccac tcaaggtcag attgtgcttg atcgtaggag acaggatgta tgaaagtgta  10200
ggcatcgatg cttacatgat ataggtgcgt ctctctccag ttgtgcagat cttcgtggca  10260
gcggagatct gattctgtga agggcgacac gtactgctca ggttgtggag gaaataattt  10320
gttggctgaa tattccagcc attgaagctt tgttgcccat tcatgaggga actcttcttt  10380
gatcatgtca agatactcct ccttagacgt tgcagtctgg ataatagttc gccatcgtgc  10440
gtcagatttg cgaggagaca ccttatgatc tcggaaatct cctctggttt taatatctcc  10500
gtcctttgat atgtaatcaa ggacttgttt agagtttcta gctggctgga tattagggtg  10560
atttccttca aaatcgaaaa aagaaggatc tctaatacaa ggttttttat caagctggat  10620
aagagcatga tagtgggtag tgccatcttg atgaagctca gaagcaacac caaggaagaa  10680
aataagaaaa ggtgtgagtt tctcccagag aaactggaat aaatcatctc tttgagatga  10740
gcacttgggg taggtaagga aaacatattt agattggagt ctgaagttct tgctagcaga  10800
aggcatgttg ttgtgactcc gaggggttgc ctcaaactct atcttataac cggcgtggag  10860
gcatggaggc aagggcattt tggtaattta agtagttagt ggaaaatgac gtcatttact  10920
taaagacgaa gtcttgcgac aagggggggcc cacgccgaat tttaatatta ccggcgtggc  10980
cccaccttat cgcgagtgct ttagcacgag cggtccagat ttaaagtaga aaagttcccg  11040
cccactaggg ttaaaggtgt tcacactata aaagcatata cgatgtgatg gtatttgatg  11100
```

-continued

```
gagcgtatat tgtatcaggt atttccgtcg gatacgaatt attcgtacgg ccggaccggt  11160
cccctaggcc ggccaattcg agatcggccg cggctgagtg gctccttcaa tcgttgcggt  11220
tctgtcagtt ccaaacgtaa aacggcttgt cccgcgtcat cggcgggggt cataacgtga  11280
ctcccttaat tctccgctca tgatcagatt gtcgtttccc gccttcagtt taaactatca  11340
gtgtttgaca ggatatattg gcgggtaaac ctaagagaaa agagcgttta ttagaataat  11400
cggatattta aaagggcgtg aaaaggttta tccgttcgtc catttgtatg tgcatgccaa  11460
ccacagggtt ccccagatct ggcgccggcc agcgagacga gcaagattgg ccgccgcccg  11520
aaacgatccg acagcgcgcc cagcacaggt gcgcaggcaa attgcaccaa cgcatacagc  11580
gccagcagaa tgccatagtg ggcggtgacg tcgttcgagt gaaccagatc gcgcaggagg  11640
cccggcagca ccggcataat caggccgatg ccgacagcgt cgagcgcgac agtgctcaga  11700
attacgatca ggggtatgtt gggtttcacg tctggcctcc ggagactgtc atacgcgtaa  11760
aaaggccgcg ttgctggcgt ttttccatag gctccgcccc cctgacgagc atcacaaaaa  11820
tcgacgctca agtcagaggt ggcgaaaccc gacaggacta taaagatacc aggcgtttcc  11880
ccctggaagc tccctcgtgc gctctcctgt tccgaccctg ccgcttaccg gatacctgtc  11940
cgcctttctc ccttcgggaa gcgtggcgct ttctcatagc tcacgctgta ggtatctcag  12000
ttcggtgtag gtcgttcgct ccaagctggg ctgtgtgcac gaaccccccg ttcagcccga  12060
ccgctgcgcc ttatccggta actatcgtct tgagtccaac ccggtaagac acgacttatc  12120
gccactggca gcagccactg gtaacaggat tagcagagcg aggtatgtag gcggtgctac  12180
agagttcttg aagtggtggc ctaactacgg ctacactaga aggacagtat ttggtatctg  12240
cgctctgctg aagccagtta ccttcggaaa aagagttggt agctcttgat ccggcaaaca  12300
aaccaccgct ggtagcggtg gtttttttgt ttgcaagcag cagattacgc gcagaaaaaa  12360
aggatctcaa gaagatcctt tgatcttttc tacggggtct gacgctcagt ggaacgaaaa  12420
ctcacgttaa gggattttgg tcatgagatt atcaaaaagg atcttcacct agatcctttt  12480
aaattaaaaa tgaagtttta aatcaatcta aagtatatat gagtaaactt ggtctgcagt  12540
tgccatgttt tacggcagtg agagcagaga tagcgctgat gtccggcggt gcttttgccg  12600
ttacgcacca ccccgtcagt agctgaacag gagggacagc tgatagacac agaagccact  12660
ggagcacctc aaaaacacca tcatacacta aatcagtaag ttggcagcat cacccataat  12720
tgtggtttca aaatcggctc cgtcgatact atgttatacg ccaactttga aaacaacttt  12780
gaaaaagctg ttttctggta tttaaggttt tagaatgcaa ggaacagtga attggagttc  12840
gtcttgttat aattagcttc ttggggtatc tttaaatact gtagaaaaga ggaaggaaat  12900
aataaatggc taaaatgaga atatcaccgg aattgaaaaa actgatcgaa aaataccgct  12960
gcgtaaaaga tacggaagga atgtctcctg ctaaggtata taagctggtg ggagaaaatg  13020
aaaacctata tttaaaaatg acggacagcc ggtataaagg gaccacctat gatgtggaac  13080
gggaaaagga catgatgcta tggctggaag gaaagctgcc tgttccaaag gtcctgcact  13140
ttgaacggca tgatggctgg agcaatctgc tcatgagtga ggccgatggc gtcctttgct  13200
cggaagagta tgaagatgaa caaagccctg aaaagattat cgagctgtat gcggagtgca  13260
tcaggctctt tcactccatc gacatatcgg attgtcccta tacgaatagc ttagacagcc  13320
gcttagccga attggattac ttactgaata acgatctggc cgatgtggat tgcgaaaact  13380
gggaagaaga cactccattt aaagatccgc gcgagctgta tgatttttta aagacggaaa  13440
agcccgaaga ggaacttgtc ttttcccacg gcgacctggg agacagcaac atctttgtga  13500
```

-continued

```
aagatggcaa agtaagtggc tttattgatc ttgggagaag cggcagggcg gacaagtggt  13560
atgacattgc cttctgcgtc cggtcgatca gggaggatat cggggaagaa cagtatgtcg  13620
agctattttt tgacttactg gggatcaagc ctgattggga gaaaataaaa tattatattt  13680
tactggatga attgttttag tacctagatg tggcgcaacg atgccggcga caagcaggag  13740
cgcaccgact tcttccgcat caagtgtttt ggctctcagg ccgaggccca cggcaagtat  13800
ttgggcaagg ggtcgctggt attcgtgcag ggcaagattc ggaataccaa gtacgagaag  13860
gacggccaga cggtctacgg gaccgacttc attgccgata aggtggatta tctggacacc  13920
aaggcaccag gcgggtcaaa tcaggaataa gggcacattg ccccggcgtg agtcggggca  13980
atcccgcaag gagggtgaat gaatcggacg tttgaccgga aggcatacag gcaagaactg  14040
atcgacgcgg ggtttttccgc cgaggatgcc gaaaccatcg caagccgcac cgtcatgcgt  14100
gcgccccgcg aaaccttcca gtccgtcggc tcgatggtcc agcaagctac ggccaagatc  14160
gagcgcgaca gcgtgcaact ggctccccct gccctgcccg cgccatcggc cgccgtggag  14220
cgttcgcgtc gtctcgaaca ggaggcggca ggtttggcga agtcgatgac catcgacacg  14280
cgaggaacta tgacgaccaa gaagcgaaaa accgccggcg aggacctggc aaaacaggtc  14340
agcgaggcca agcaggccgc gttgctgaaa cacacgaagc agcagatcaa ggaaatgcag  14400
ctttccttgt tcgatattgc gccgtggccg gacacgatgc gagcgatgcc aaacgacacg  14460
gcccgctctg ccctgttcac cacgcgcaac aagaaaatcc cgcgcgaggc gctgcaaaac  14520
aaggtcattt tccacgtcaa caaggacgtg aagatcacct acaccggcgt cgagctgcgg  14580
gccgacgatg acgaactggt gtggcagcag gtgttggagt acgcgaagcg cacccctatc  14640
ggcgagccga tcaccttcac gttctacgag ctttgccagg acctgggctg gtcgatcaat  14700
ggccggtatt acacgaaggc cgaggaatgc ctgtcgcgcc tacaggcgac ggcgatgggc  14760
ttcacgtccg accgcgttgg gcacctggaa tcggtgtcgc tgctgcaccg cttccgcgtc  14820
ctggaccgtg gcaagaaaac gtcccgttgc caggtcctga tcgacgagga aatcgtcgtg  14880
ctgtttgctg gcgaccacta cacgaaattc atatgggaga agtaccgcaa gctgtcgccg  14940
acggcccgac ggatgttcga ctatttcagc tcgcaccggg agccgtaccc gctcaagctg  15000
gaaaccttcc gcctcatgtg cggatcggat tccacccgcg tgaagaagtg gcgcgagcag  15060
gtcggcgaag cctgcgaaga gttgcgaggc agcggcctgg tggaacacgc ctgggtcaat  15120
gatgacctgg tgcattgcaa acgctagggc cttgtggggt cagttccggc tgggggttca  15180
gcagccagcg ctttactggc atttcaggaa caagcgggca ctgctcgacg cacttgcttc  15240
gctcagtatc gctcgggacg cacggcgcgc tctacgaact gccgataaac agaggattaa  15300
aattgacaat tcaatggcaa ggactgccag cgctgccatt tttggggtga ggccgttcgc  15360
ggccgagggg cgcagcccct gggggggatgg gaggcccgcg ttagcgggcc gggagggttc  15420
gagaaggggg ggcacccccc ttcggcgtgc gcggtcacgc gcacagggcg cagccctggt  15480
taaaaacaag gtttataaat attggtttaa aagcaggtta aaagacaggt tagcggtggc  15540
cgaaaaacgg gcggaaaccc ttgcaaatgc tggattttct gcctgtggac agcccctcaa  15600
atgtcaatag gtgcgcccct catctgtcag cactctgccc ctcaagtgtc aaggatcgcg  15660
cccctcatct gtcagtagtc gcgcccctca agtgtcaata ccgcagggca cttatcccca  15720
ggcttgtcca catcatctgt gggaaactcg cgtaaaatca ggcgttttcg ccgatttgcg  15780
aggctggcca gctccacgtc gccggccgaa atcgagcctg cccctcatct gtcaacgccg  15840
```

cgccgggtga gtcggcccct caagtgtcaa cgtccgcccc tcatctgtca gtgagggcca 15900
agttttccgc gaggtatcca caacgccggc ggccgcggtg tctcgcacac ggcttcgacg 15960
gcgtttctgg cgcgtttgca gggccataga cggccgccag cccagcggcg agggcaacca 16020
gcccggtgag cgtcgcaaag gcgctcggtc ttgccttgct cgtcgagatc tggggtcgat 16080
cagccgggga tgcatcaggc cgacagtcgg aacttcgggt ccccgacctg taccattcgg 16140
tgagcaatgg ataggggagt tgatatcgtc aacgttcact tctaaagaaa tagcgccact 16200
cagcttcctc agcggcttta tccagcgatt tcctattatg tcggcatagt tctcaagatc 16260
gacagcctgt cacggttaag cgagaaatga ataagaaggc tgataattcg gatctctgcg 16320
agggagatga tatttgatca caggcagcaa cgctctgtca tcgttacaat caacatgcta 16380
ccctccgcga gatcatccgt gtttcaaacc cggcagctta gttgccgttc ttccgaatag 16440
catcggtaac atgagcaaag tctgccgcct tacaacggct ctcccgctga cgccgtcccg 16500
gactgatggg ctgcctgtat cgagtggtga ttttgtgccg agctgccggt cggggagctg 16560
ttggctggct ggtggcagga tatattgtgg tgtaaacaaa ttgacgctta gacaacttaa 16620
taacacattg cggacgtttt taatgtactg gggtggtttt tcttttcacc agtgagacgg 16680
gcaacagctg attgcccttc accgcctggc cctgagagag ttgcagcaag cggtccacgc 16740
tggtttgccc cagcaggcga aaatcctgtt tgatggtggt tccgaaatcg gcaaaatccc 16800
ttataaatca aaagaatagc ccgagatagg gttgagtgtt gttccagttt ggaacaagag 16860
tccactatta aagaacgtgg actccaacgt caaagggcga aaaaccgtct atcagggcga 16920
tggcccacta cgtgaaccat cacccaaatc aagttttttg gggtcgaggt gccgtaaagc 16980
actaaatcgg aaccctaaag ggagcccccg atttagagct tgacggggaa agccggcgaa 17040
cgtggcgaga aaggaaggga agaaagcgaa aggagcgggc gccattcagg ctgcgcaact 17100
gttgggaagg g 17111

<210> SEQ ID NO 117
<211> LENGTH: 19330
<212> TYPE: DNA
<213> ORGANISM: Artificial Sequence
<220> FEATURE:
<223> OTHER INFORMATION: pBY11-h6D8M2

<400> SEQUENCE: 117
cgatcggtcg attcatagaa gattagattt ttcatagtat ttttttaaag taaaccttta 60
actacggtta ggacactttt aagttaaatt taatttgaac ccttaaatta atttttaaaa 120
tagataaata tcaatcatcc tgatatgctt ttgaaaaaat gaatgagaaa gatgattcaa 180
ttaaggccac attttaatca tgactaaaat aatatacagt ataatttcat atatatttgc 240
tttaaaaaaa aattgacaat ccattcgttt ctagcaataa atttcttcaa ccacaaatat 300
attaaagata actacggcat agaaacaaaa atctatgaag aatttttgta tacttcatat 360
gaaattaaaa aaaacttcat tgaacatcaa aataataata ataatcataa actcctcaat 420
atttatattc ctagcttctt gaattaaatt gtttacatat tcaacgatgt aaaaaattat 480
ttctctatct attttcctta tatcatgcat ggtttcacat atatcaaagg ataaaagcaa 540
tctatgtaaa ttatctcact ttattaagtt ttctatctga attattgaga acgtagattt 600
ctttttgcac tatcccccaa taattagcaa aacacaccta gactagattt gttttgctaa 660
cccaattgat attaattata tatgattaat atttatatgt atatggaatt ggttaataaa 720
atgcatctgg ttcatcaaag aattataaag acacgtgaca ttcatttagg ataagaaata 780

```
tggatgatct ctttctctta ttcagataat tagtaattac acataacaca caactttgat    840
gcccacatta tagtgattag catgtcacta tgtgtgcatc cttttatttc atacattaat    900
taacttggcc aatccagaag atggacaagt ctagggtcac attgcagggt actctagctt    960
actcgccttc tttttcgaag gtttgagtac cttcagggca tcctcttgat acattacttt   1020
ccacttcgat tggggcaagc tgtagcagtt cttgcttaga ccgaattgcc atctcacaga   1080
gatgctgaag agttcgcgac cctccagaaa cggtgatact aactcctcga aaccgaatac   1140
tataggtaca tccgatctgg tcgaaaccga aaaatcgaga tgctgcatag ttaaccgaat   1200
ctcccgtcca agatccaagg actctgtgca gtgaagcttc cgtcctgtcg tatctgagat   1260
atctcttaaa tacaactttc ccgaaacccc agctttcctt gaaaccaagg ggattatctt   1320
gattcgaatt cgtctcatcg ttatgtagcc gccactcagt ccaactcgga ctttcgtcag   1380
gaagtttgaa gggagaagtt gtacctcctg atcctccatc ccaacgttca ctgttagctt   1440
gttccctagc gtcgtttcct tgtatagctc gttccatgga ttgtaaatag taattgtaat   1500
gttgtttgtt gtttgttgtt gttggtaatt gttgtaaaaa tacgctctcc aaatgaaatg   1560
aacttcctta tatagaggaa gggtcttgcg aaggatagtg ggattgtgcg tcatccctta   1620
cgtcagtgga gatatcacat caatccactt gctttgaaga cgtggttgga acgtcttctt   1680
tttccacgat gctcctcgtg ggtgggggtc catctttggg accactgtcg gcagaggcat   1740
cttcaacgat ggcctttcct ttatcgcaat gatggcattt gtaggagcca ccttcctttt   1800
ccactatctt cacaataaag tgacagatag ctgggcaatg gaatccgagg aggtttccgg   1860
atattaccct ttgttgaaaa gtctcaattg ccctttggtc ttctgagact gtatctttga   1920
tatttttgga gtagacaagt gtgtcgtgct ccaccatgtt ctggcaattc cggttcgctt   1980
gctgtccata aaaccgccca gtctagctat cgccatgtaa gcccactgca agctacctgc   2040
tttctctttg cgcttgcgtt ttcccttgtc cagatagccc agtagctgac attcatccgg   2100
ggtcagcacc gtttctgcgg actggctttc tacgtgttcc gcttccttta gcagcccttg   2160
cgccctgagt gcttgcggca gcgtgaagct ggcgcgccgc tctagcagaa ggcatgttgt   2220
tgtgactccg aggggttgcc tcaaactcta tcttataacc ggcgtggagg catggaggca   2280
agggcatttt ggtaatttaa gtagttagtg gaaaatgacg tcatttactt aaagacgaag   2340
tcttgcgaca agggggggcc acgccgaatt ttaatattac cggcgtggcc ccaccttatc   2400
gcgagtgctt tagcacgagc ggtccagatt taaagtagaa aagttcccgc ccactagggt   2460
taaaggtgtt cacactataa aagcatatac gatgtgatgg tatttgatgg agcgtatatt   2520
gtatcaggta tttccgtcgg atacgaatta ttcgtacgac cctcctgcag gtcaacatgg   2580
tggagcacga cacacttgtc tactccaaaa atatcaaaga tacagtctca gaagaccaaa   2640
gggcaattga gacttttcaa caaagggtaa tatccggaaa cctcctcgga ttccattgcc   2700
cagctatctg tcactttatt gtgaagatag tggaaaagga aggtggctcc tacaaatgcc   2760
atcattgcga taaaggaaag gccatcgttg aagatgcctc tgccgacagt ggtcccaaag   2820
atggaccccc acccacgagg agcatcgtgg aaaaagaaga cgttccaacc acgtcttcaa   2880
agcaagtgga ttgatgtgat aacatggtgg agcacgacac acttgtctac tccaaaaata   2940
tcaaagatac agtctcagaa gaccaaaggg caattgagac ttttcaacaa agggtaatat   3000
ccggaaacct cctcggattc cattgcccag ctatctgtca ctttattgtg aagatagtgg   3060
aaaaggaagg tggctcctac aaatgccatc attgcgataa aggaaaggcc atcgttgaag   3120
```

-continued

```
atgcctctgc cgacagtggt cccaaagatg gacccccacc cacgaggagc atcgtggaaa   3180
aagaagacgt tccaaccacg tcttcaaagc aagtggattg atgtgatatc tccactgacg   3240
taagggatga cgcacaatcc cactatcctt cgcaagaccc ttcctctata taaggaagtt   3300
catttcattt ggagaggacc tcgagaaaca aacaaaatca acaaatatag aaaataacgc   3360
atttccaatt ctttgaaatt tctgcaacat ctagaacaat gggatggtct tgcatcatac   3420
tctttcttgt tgcaactgct acaggtgtcc actctgatgt tcagcttctc gagtctggag   3480
gtggtcttgt gcaacctgga ggttccttga gactctcctg tgcagcttca gggtttgact   3540
tcagtaggta ctggatgagt tgggttcgtc aagctcctgg gaaaggacta gaatggattg   3600
gagagatcaa tccagattca agtaccatca actatactcc atctctgaag gatcgcttca   3660
ccatttccag agacaatgcc aagaacacgt tgtatcttca gatgaacagc ttgaggactg   3720
aagacacagc cttgtactac tgcacaagac agggctatgg ctacaactac tggggtcaag   3780
gcaccactgt cacagtgtct tcagctagca ccaaaggtcc atcggtcttt ccactggcac   3840
cttcttccaa gagtacttct ggaggcacag ctgcactggg ttgtcttgtc aaggactact   3900
ttccagaacc tgttacggtt tcgtggaact caggtgctct gaccagtgga gtgcacacct   3960
ttccagctgt tcttcagtcc tcaggattgt attctcttag cagtgttgtg actgttccat   4020
cctcaagctt gggcactcag acctacatct gcaatgtgaa tcacaaaccc agcaacacca   4080
aggttgacaa gaaagttgag cccaagtctt gtgacaagac tcatacgtgt ccaccgtgcc   4140
cagcacctga acttcttgga ggaccgtcag tcttcttgtt tcctccaaag cctaaggata   4200
ccttgatgat ctccaggact cctgaagtca catgtgtagt tgtggatgtg agccatgaag   4260
atcctgaggt gaagttcaac tggtatgtgg atggtgtgga agtgcacaat gccaagacaa   4320
agccgagaga ggaacagtac aacagcacgt acagggttgt ctcagttctc actgttctcc   4380
atcaagattg gttgaatggc aaagagtaca agtgcaaggt ctccaacaaa gccctcccag   4440
cccccattga gaagaccatt tccaaagcga aagggcaacc ccgtgaacca caagtgtaca   4500
cacttcctcc atctcgcgat gaactgacca agaaccaggt cagcttgact tgcctggtga   4560
aaggcttcta tccctctgac atagctgtag agtgggagag caatgggcaa ccggagaaca   4620
actacaagac tacacctccc gttctcgatt ctgacggctc cttcttcctc tacagcaagc   4680
tcacagtgga caagagcagg tggcaacaag ggaatgtctt ctcatgctcc gtgatgcatg   4740
aggctcttca caatcactac acacagaaga gtctctcctt gtctccgggt aaaggaggtg   4800
gcggatcagg tggaggcggt tcaggcggag gtggatcctc tttgcttacc gaggttgaga   4860
cccctattag aaacgagtgg ggttgcagat gtaacgattc ttccgacgga ggttctggag   4920
gttccctttt gactgaagtg gagactccaa tcaggaacga atgggggatgc agatgcaacg   4980
actcctctga cggaggtgga actagtcata acactcctgt ttacaagctg gacatatctg   5040
aggcaactca ataagagctc aaagcagaat gctgagctaa aagaaaggct ttttccattt   5100
tcgagagaca atgagaaaag aagaagaaga agaagaagaa gaagaagaag aaaagagtaa   5160
ataataaagc cccacaggag gcgaagttct tgtagctcca tgttatctaa gttattgata   5220
ttgtttgccc tatattttat ttctgtcatt gtgtatgttt tgttcagttt cgatctcctt   5280
gcaaaatgca gagattatga gatgaataaa ctaagttata ttattatacg tgttaatatt   5340
ctcctcctct ctctagctag ccttttgttt tctctttttc ttatttgatt ttctttaaat   5400
caatccattt taggagaggg ccagggagtg atccagcaaa acatgaagat tagaagaaac   5460
ttccctcttt tttttcctga aaacaattta acgtcgagat ttatctcttt ttgtaatgga   5520
```

-continued

```
atcatttcta cagttatgac gctcatacag cattcccaga aagagaaaca gaagaaatat   5580
acaaactttc attttgagag cagcacctcg tctattgatt gcagataata tgcttctcat   5640
ttgtatttcc ttttgattat ttttgtttct atccctttgt ttgagtcaat ctcaaatatt   5700
cggtcattgt tggtatgaaa aatcaagcag ttcatgttaa gagtcaattt aaaattaata   5760
tttttatata gagttgtatg tgaaatgatg ttgtgatttg gtatatatgg ataaagagct   5820
tgtcagttca ttttggtctg atttttttgg tatccaaata agaaacacaa aagggatatg   5880
tccctctact atcaaatatt agttataagt attcatgtta tactattcga tattttctac   5940
cccaatcgtt acctatttaa aagtatttac ccctccatct atcaaacccc tggacccagc   6000
tttcctatta catgtggctt catcttaagc ccccaaacct ttttcttatt tttgattttt   6060
aaaggctcat cttaaaattt attactcaaa ttaatacctc ttaataaccc acctcaagga   6120
cccagtaatt aaatatccaa ttagctccag taattggggt tcatattagc tccagtctta   6180
aattttaaag gcgatgatcg tattcctcca cttggttcat ttatactcaa agaatactca   6240
atgtctttag tgtttagata actttttgta aatcatatag attgttttaa caaaaaacaa   6300
ttcaatagta gattttcaca tgaaagttac ataaaaattc tttaaaatta ctttctcaaa   6360
aaattgttcc aaacatatta tcccacaatt aaactcaatc tgtttttcga aacctaaatc   6420
aaaaccaatc caactacctt atataatata taatcaatac attgtaaaga actgcatgtt   6480
cttttaaatt ttgggggcaa agttattccg tacgttcaca catgtactaa taggaggtaa   6540
taaatgatat gtgaaacaat cgaggtgtaa acaagctagc atgaattctc gattaaaaat   6600
cccaattata tttggtctaa tttagtttgg tattgagtaa aacaaattcg aaccaaacca   6660
aaatataaat atatagtttt tatatatatg cctttaagac tttttataga attttcttta   6720
aaaaatatct agaaatattt gcgactcttc tggcatgtaa tatttcgtta aatatgaagt   6780
gctccatttt tattaacttt aaataattgg ttgtacgatc actttcttat caagtgttac   6840
taaaatgcgt caatctcttt gttcttccat attcatatgt caaaatctat caaaattctt   6900
atatatcttt ttcgaatttg aagtgaaatt tcgataattt aaaattaaat agaacatatc   6960
attatttagg tatcatattg atttttatac ttaattacta aatttggtta actttgaaag   7020
tgtacatcaa cgaaaaatta gtcaaacgac taaaataaat aaatatcatg tgttattaag   7080
aaaattctcc tataagaata ttttaataga tcatatgttt gtaaaaaaaa ttaattttta   7140
ctaacacata tatttactta tcaaaaattt gacaaagtaa gattaaaata atattcatct   7200
aacaaaaaaa aaaccagaaa atgctgaaaa cccggcaaaa ccgaaccaat ccaaaccgat   7260
atagttggtt tggtttgatt ttgatataaa ccgaaccaac tcggtccatt tgcacccta   7320
atcataatag ctttaatatt tcaagatatt attaagttaa cgttgtcaat atcctggaaa   7380
ttttgcaaaa tgaatcaagc ctatatggct gtaatatgaa tttaaaagca gctcgatgtg   7440
gtggtaatat gtaatttact tgattctaaa aaaatatccc aagtattaat aatttctgct   7500
aggaagaagg ttagctacga tttacagcaa agccagaata caaagaacca taaagtgatt   7560
gaagctcgaa atatacgaag gaacaaatat ttttaaaaaa atacgcaatg acttggaaca   7620
aaagaaagtg atatattttt tgttcttaaa caagcatccc ctctaaagaa tggcagtttt   7680
cctttgcatg taactattat gctcccttcg ttacaaaaat tttggactac tattgggaac   7740
ttcttctgaa aatagtggta ccgagtgtac ttcaagtcag ttggaaatca ataaaatgat   7800
tattttatga atatatttca ttgtgcaagt agatagaaat tacatatgtt acataacaca   7860
```

-continued

```
cgaaataaac aaaaaaacac aatccaaaac aaacacccca aacaaaataa cactatatat    7920
atcctcgtat gaggagaggc acgttcagtg actcgacgat tcccgagcaa aaaaagtctc    7980
cccgtcacac atatagtggg tgacgcaatt atcttcaaag taatccttct gttgacttgt    8040
cattgataac atccagtctt cgtcaggatt ccaaagaatt atagaaggga tcggtcaaca    8100
tggtggagca cgacacactt gtctactcca aaaatatcaa agatacagtc tcagaagacc    8160
aaagggcaat tgagactttt caacaaaggg taatatccgg aaacctcctc ggattccatt    8220
gcccagctat ctgtcacttt attgtgaaga tagtggaaaa ggaaggtggc tcctacaaat    8280
gccatcattg cgataaagga aaggccatcg ttgaagatgc ctctgccgac agtggtccca    8340
aagatggacc cccacccacg aggagcatcg tggaaaaaga agacgttcca accacgtctt    8400
caaagcaagt ggattgatgt gataacatgg tggagcacga cacacttgtc tactccaaaa    8460
atatcaaaga tacagtctca gaagaccaaa gggcaattga gacttttcaa caaagggtaa    8520
tatccggaaa cctcctcgga ttccattgcc cagctatctg tcactttatt gtgaagatag    8580
tggaaaagga aggtggctcc tacaaatgcc atcattgcga taaaggaaag gccatcgttg    8640
aagatgcctc tgccgacagt ggtcccaaag atggaccccc acccacgagg agcatcgtgg    8700
aaaaagaaga cgttccaacc acgtcttcaa agcaagtgga ttgatgtgat atctccactg    8760
acgtaaggga tgacgcacaa tcccactatc cttcgcaaga cccttcctct atataaggaa    8820
gttcatttca tttggagagg acctcgagaa acaaacaaaa tcaacaaata tagaaaataa    8880
cgcatttcca attctttgaa atttctgcaa catctagaac aatgggatgg tcttgcatca    8940
ttctcttctt ggtagccaca gctacaggtg tccactccga tgttttgatg actcaaagcc    9000
ctctctcact tcctgtgact cttggacagc ccgcatccat atcttgcaga tctagtcaga    9060
gtattgttca tagtaacggc aacacctact tggaatggta tctgcagaaa ccaggccagt    9120
ctccaaagct tctgatctac aaggcttcca atcgtttctc tggtgtccca gacaggttta    9180
gtggcagtgg atcagggact gacttcacat tgaagatcag cagagttgag gctgaagatg    9240
cgggagtgta ctattgtctt caaggttcac atgttccgtc aacgtttgga ggtgggacca    9300
aagtggagat caagactgtt gcggcgccat ctgtcttcat ctttcctcca tctgatgaac    9360
aactcaagtc tggaactgct tctgttgtgt gccttctgaa caacttctat cctagagaag    9420
ccaaagtaca gtggaaggtt gacaatgctc ttcaatcagg taactcccag gagagtgtca    9480
cagagcaaga ttccaaggat tccacctaca gcctctcaag taccttgacg ttgagcaagg    9540
cagactatga gaaacacaaa gtgtacgcat gcgaagtcac tcatcagggc ctgtcatcac    9600
ccgtgacaaa gagcttcaac aggggagagt gttaggtacc gagctcaaag cagaatgctg    9660
agctaaaaga aaggcttttt ccattttcga gagacaatga gaaaagaaga agaagaagaa    9720
gaagaagaag aagaagaaaa gagtaaataa taaagcccca caggaggcga agttcttgta    9780
gctccatgtt atctaagtta ttgatattgt ttgccctata ttttatttct gtcattgtgt    9840
atgttttgtt cagtttcgat ctccttgcaa aatgcagaga ttatgagatg aataaactaa    9900
gttatattat tatacgtgtt aatattctcc tcctctctct agctagcctt ttgttttctc    9960
tttttcttat ttgattttct ttaaatcaat ccattttagg agagggccag ggagtgatcc   10020
agcaaaacat gaagattaga agaaacttcc ctcttttttt tcctgaaaac aatttaacgt   10080
cgagatttat ctctttttgt aatggaatca tttctacagt tatgacggct cactgaggaa   10140
atatatagac aaattaagtt tggttctatg agttctaatt tggacttaag agttgtttga   10200
aattctattt tatagtgatg cttataatgt atttggactg ttttctgctg tgtgtaagac   10260
```

-continued

```
cttttggtct gtgaactgga aacatacatg aataaatttc tttgaattta ctggaatttt  10320
tgcatcaaca aaagaaaaat tgaagttact aacttgtaaa tggaacaatt gtaatgttaa  10380
aggatataaa tatcttaata tagtgcgata cgaatcacac gaatgcaaga ctttctctct  10440
ctgctcccgc tcatgctctc ggtgcatgtt agctaaatat acatcggtgc atccatggca  10500
ggagcatgag gacggggatg aggaagggag tgaggagggc caaaagaagt acacatagtt  10560
tcctttggga gcgaattctc gattaaaaat cccaattata tttggtctaa tttagtttgg  10620
tattgagtaa aacaaattcg aaccaaacca aaatataaat atatagtttt tatatatatg  10680
cctttaagac tttttataga attttcttta aaaaatatct agaaatattt gcgactcttc  10740
tggcatgtaa tatttcgtta aatatgaagt gctccatttt tattaacttt aaataattgg  10800
ttgtacgatc actttcttat caagtgttac taaaatgcgt caatctcttt gttcttccat  10860
attcatatgt caaaatctat caaaattctt atatatcttt ttcgaatttg aagtgaaatt  10920
tcgataattt aaaattaaat agaacatatc attatttagg tatcatattg atttttatac  10980
ttaattacta aatttggtta actttgaaag tgtacatcaa cgaaaaatta gtcaaacgac  11040
taaaataaat aaatatcatg tgttattaag aaaattctcc tataagaata ttttaataga  11100
tcatatgttt gtaaaaaaaa ttaattttta ctaacacata tatttactta tcaaaaattt  11160
gacaaagtaa gattaaaata atattcatct aacaaaaaaa aaaccagaaa atgctgaaaa  11220
cccggcaaaa ccgaaccaat ccaaaccgat atagttggtt tggtttgatt ttgatataaa  11280
ccgaaccaac tcggtccatt tgcaccccta atcataatag ctttaatatt tcaagatatt  11340
attaagttaa cgttgtcaat atcctggaaa ttttgcaaaa tgaatcaagc ctatatggct  11400
gtaatatgaa tttaaaagca gctcgatgtg gtggtaatat gtaatttact tgattctaaa  11460
aaaatatccc aagtattaat aatttctgct aggaagaagg ttagctacga tttacagcaa  11520
agccagaata caaagaacca taaagtgatt gaagctcgaa atatacgaag gaacaaatat  11580
ttttaaaaaa atacgcaatg acttggaaca aaagaaagtg atatattttt tgttcttaaa  11640
caagcatccc ctctaaagaa tggcagtttt cctttgcatg taactattat gctcccttcg  11700
ttacaaaaat tttggactac tattgggaac ttcttctgaa aatagtggta ccgagtgtac  11760
ttcaagtcag ttggaaatca ataaaatgat tattttatga atatatttca ttgtgcaagt  11820
agatagaaat tacatatgtt acataacaca cgaaataaac aaaaaaacac aatccaaaac  11880
aaacacccca aacaaaataa cactatatat atcctcgtat gaggagaggc acgttcagtg  11940
actcgacgat tcccgagcaa aaaaagtctc cccgtcacac atatagtggg tgacgcaatt  12000
atcttcaaag taatccttct gttgacttgt cattgataac atccagtctt cgtcaggatt  12060
gcaaagaatt atagaaggga ttccaccttt tattttcttc ttttttccat atttagggtt  12120
gacagtgaaa tcagactggc aacctattaa ttgcttccac aatgggacga acttgaaggg  12180
gatgtcgtcg atgatattat aggtggcgtg ttcatcgtag ttggtgaagt cgatggtccc  12240
gttccagtag ttgtgtcgcc cgagacttct agcccaggtg gtctttccgg tacgagttgg  12300
tccgcagatg tagaggctgg ggtgtctgac cccagtcctt ccctcatcct ggttagatcg  12360
gccatccact caaggtcaga ttgtgcttga tcgtaggaga caggatgtat gaaagtgtag  12420
gcatcgatgc ttacatgata taggtgcgtc tctctccagt tgtgcagatc ttcgtggcag  12480
cggagatctg attctgtgaa gggcgacacg tactgctcag gttgtggagg aaataatttg  12540
ttggctgaat attccagcca ttgaagcttt gttgcccatt catgagggaa ctcttctttg  12600
```

-continued

```
atcatgtcaa gatactcctc cttagacgtt gcagtctgga taatagttcg ccatcgtgcg  12660
tcagatttgc gaggagacac cttatgatct cggaaatctc ctctggtttt aatatctccg  12720
tcctttgata tgtaatcaag gacttgttta gagtttctag ctggctggat attagggtga  12780
tttccttcaa aatcgaaaaa agaaggatct ctaatacaag gttttttatc aagctggata  12840
agagcatgat agtgggtagt gccatcttga tgaagctcag aagcaacacc aaggaagaaa  12900
ataagaaaag gtgtgagttt ctcccagaga aactggaata aatcatctct ttgagatgag  12960
cacttggggt aggtaaggaa aacatattta gattggagtc tgaagttctt gctagcagaa  13020
ggcatgttgt tgtgactccg aggggttgcc tcaaactcta tcttataacc ggcgtggagg  13080
catggaggca agggcatttt ggtaatttaa gtagttagtg gaaaatgacg tcatttactt  13140
aaagacgaag tcttgcgaca aggggggccc acgccgaatt ttaatattac cggcgtggcc  13200
ccaccttatc gcgagtgctt tagcacgagc ggtccagatt taaagtagaa aagttcccgc  13260
ccactagggt taaaggtgtt cacactataa aagcatatac gatgtgatgg tatttgatgg  13320
agcgtatatt gtatcaggta tttccgtcgg atacgaatta ttcgtacggc cggaccggtc  13380
ccctaggccg gccaattcga gatcggccgc ggctgagtgg ctccttcaat cgttgcggtt  13440
ctgtcagttc caaacgtaaa acggcttgtc ccgcgtcatc ggcgggggtc ataacgtgac  13500
tcccttaatt ctccgctcat gatcagattg tcgtttcccg ccttcagttt aaactatcag  13560
tgtttgacag gatatattgg cgggtaaacc taagagaaaa gagcgtttat tagaataatc  13620
ggatatttaa aagggcgtga aaaggtttat ccgttcgtcc atttgtatgt gcatgccaac  13680
cacagggttc cccagatctg gcgccggcca gcgagacgag caagattggc cgccgcccga  13740
aacgatccga cagcgcgccc agcacaggtg cgcaggcaaa ttgcaccaac gcatacagcg  13800
ccagcagaat gccatagtgg gcggtgacgt cgttcgagtg aaccagatcg cgcaggaggc  13860
ccggcagcac cggcataatc aggccgatgc cgacagcgtc gagcgcgaca gtgctcagaa  13920
ttacgatcag gggtatgttg ggtttcacgt ctggcctccg gagactgtca tacgcgtaaa  13980
aaggccgcgt tgctggcgtt tttccatagg ctccgccccc ctgacgagca tcacaaaaat  14040
cgacgctcaa gtcagaggtg gcgaaacccg acaggactat aaagatacca ggcgtttccc  14100
cctggaagct ccctcgtgcg ctctcctgtt ccgaccctgc cgcttaccgg atacctgtcc  14160
gcctttctcc cttcgggaag cgtggcgctt tctcatagct cacgctgtag gtatctcagt  14220
tcggtgtagg tcgttcgctc caagctgggc tgtgtgcacg aaccccccgt tcagcccgac  14280
cgctgcgcct tatccggtaa ctatcgtctt gagtccaacc cggtaagaca cgacttatcg  14340
ccactggcag cagccactgg taacaggatt agcagagcga ggtatgtagg cggtgctaca  14400
gagttcttga agtggtggcc taactacggc tacactagaa ggacagtatt tggtatctgc  14460
gctctgctga agccagttac cttcggaaaa agagttggta gctcttgatc cggcaaacaa  14520
accaccgctg gtagcggtgg tttttttgtt tgcaagcagc agattacgcg cagaaaaaaa  14580
ggatctcaag aagatccttt gatcttttct acggggtctg acgctcagtg gaacgaaaac  14640
tcacgttaag ggattttggt catgagatta tcaaaaagga tcttcaccta gatcctttta  14700
aattaaaaat gaagttttaa atcaatctaa agtatatatg agtaaacttg gtctgcagtt  14760
gccatgtttt acggcagtga gagcagagat agcgctgatg tccggcggtg cttttgccgt  14820
tacgcaccac cccgtcagta gctgaacagg agggacagct gatagacaca gaagccactg  14880
gagcacctca aaaacaccat catacactaa atcagtaagt tggcagcatc acccataatt  14940
gtggtttcaa aatcggctcc gtcgatacta tgttatacgc caactttgaa aacaactttg  15000
```

-continued

```
aaaaagctgt tttctggtat ttaaggtttt agaatgcaag gaacagtgaa ttggagttcg  15060
tcttgttata attagcttct tggggtatct ttaaatactg tagaaaagag gaaggaaata  15120
ataaatggct aaaatgagaa tatcaccgga attgaaaaaa ctgatcgaaa aataccgctg  15180
cgtaaaagat acggaaggaa tgtctcctgc taaggtatat aagctggtgg gagaaaatga  15240
aaacctatat ttaaaaatga cggacagccg gtataaaggg accacctatg atgtggaacg  15300
ggaaaaggac atgatgctat ggctggaagg aaagctgcct gttccaaagg tcctgcactt  15360
tgaacggcat gatggctgga gcaatctgct catgagtgag gccgatggcg tcctttgctc  15420
ggaagagtat gaagatgaac aaagccctga aaagattatc gagctgtatg cggagtgcat  15480
caggctcttt cactccatcg acatatcgga ttgtccctat acgaatagct tagacagccg  15540
cttagccgaa ttggattact tactgaataa cgatctggcc gatgtggatt gcgaaaactg  15600
ggaagaagac actccattta aagatccgcg cgagctgtat gattttttaa agacggaaaa  15660
gcccgaagag gaacttgtct tttcccacgg cgacctggga gacagcaaca tctttgtgaa  15720
agatggcaaa gtaagtggct ttattgatct tgggagaagc ggcagggcgg acaagtggta  15780
tgacattgcc ttctgcgtcc ggtcgatcag ggaggatatc ggggaagaac agtatgtcga  15840
gctatttttt gacttactgg ggatcaagcc tgattgggag aaaataaaat attatatttt  15900
actggatgaa ttgttttagt acctagatgt ggcgcaacga tgccggcgac aagcaggagc  15960
gcaccgactt cttccgcatc aagtgttttg gctctcaggc cgaggcccac ggcaagtatt  16020
tgggcaaggg gtcgctggta ttcgtgcagg gcaagattcg gaataccaag tacgagaagg  16080
acggccagac ggtctacggg accgacttca ttgccgataa ggtggattat ctggacacca  16140
aggcaccagg cgggtcaaat caggaataag ggcacattgc cccggcgtga gtcggggcaa  16200
tcccgcaagg agggtgaatg aatcggacgt ttgaccggaa ggcatacagg caagaactga  16260
tcgacgcggg gttttccgcc gaggatgccg aaaccatcgc aagccgcacc gtcatgcgtg  16320
cgccccgcga aaccttccag tccgtcggct cgatggtcca gcaagctacg gccaagatcg  16380
agcgcgacag cgtgcaactg gctccccctg ccctgcccgc gccatcggcc gccgtggagc  16440
gttcgcgtcg tctcgaacag gaggcggcag gtttggcgaa gtcgatgacc atcgacacgc  16500
gaggaactat gacgaccaag aagcgaaaaa ccgccggcga ggacctggca aaacaggtca  16560
gcgaggccaa gcaggccgcg ttgctgaaac acacgaagca gcagatcaag gaaatgcagc  16620
tttccttgtt cgatattgcg ccgtggccgg acacgatgcg agcgatgcca aacgacacgg  16680
cccgctctgc cctgttcacc acgcgcaaca agaaaatccc gcgcgaggcg ctgcaaaaca  16740
aggtcatttt ccacgtcaac aaggacgtga agatcaccta caccggcgtc gagctgcggg  16800
ccgacgatga cgaactggtg tggcagcagg tgttggagta cgcgaagcgc acccctatcg  16860
gcgagccgat caccttcacg ttctacgagc tttgccagga cctgggctgg tcgatcaatg  16920
gccggtatta cacgaaggcc gaggaatgcc tgtcgcgcct acaggcgacg gcgatgggct  16980
tcacgtccga ccgcgttggg cacctggaat cggtgtcgct gctgcaccgc ttccgcgtcc  17040
tggaccgtgg caagaaaacg tcccgttgcc aggtcctgat cgacgaggaa atcgtcgtgc  17100
tgtttgctgg cgaccactac acgaaattca tatgggagaa gtaccgcaag ctgtcgccga  17160
cggcccgacg gatgttcgac tatttcagct cgcaccggga gccgtacccg ctcaagctgg  17220
aaaccttccg cctcatgtgc ggatcggatt ccacccgcgt gaagaagtgg cgcgagcagg  17280
tcggcgaagc ctgcgaagag ttgcgaggca gcggcctggt ggaacacgcc tgggtcaatg  17340
```

-continued

```
atgacctggt gcattgcaaa cgctagggcc ttgtggggtc agttccggct gggggttcag  17400

cagccagcgc tttactggca tttcaggaac aagcgggcac tgctcgacgc acttgcttcg  17460

ctcagtatcg ctcgggacgc acggcgcgct ctacgaactg ccgataaaca gaggattaaa  17520

attgacaatt caatggcaag gactgccagc gctgccattt ttggggtgag gccgttcgcg  17580

gccgaggggc gcagcccctg gggggatggg aggcccgcgt tagcgggccg ggagggttcg  17640

agaagggggg gcacccccct tcggcgtgcg cggtcacgcg cacagggcgc agccctggtt  17700

aaaaacaagg tttataaata ttggtttaaa agcaggttaa aagacaggtt agcggtggcc  17760

gaaaaacggg cggaaaccct tgcaaatgct ggattttctg cctgtggaca gcccctcaaa  17820

tgtcaatagg tgcgcccctc atctgtcagc actctgcccc tcaagtgtca aggatcgcgc  17880

ccctcatctg tcagtagtcg cgcccctcaa gtgtcaatac cgcagggcac ttatccccag  17940

gcttgtccac atcatctgtg ggaaactcgc gtaaaatcag gcgttttcgc cgatttgcga  18000

ggctggccag ctccacgtcg ccggccgaaa tcgagcctgc ccctcatctg tcaacgccgc  18060

gccgggtgag tcggcccctc aagtgtcaac gtccgcccct catctgtcag tgagggccaa  18120

gttttccgcg aggtatccac aacgccggcg gccgcggtgt ctcgcacacg gcttcgacgg  18180

cgtttctggc gcgtttgcag ggccatagac ggccgccagc ccagcggcga gggcaaccag  18240

cccggtgagc gtcgcaaagg cgctcggtct tgccttgctc gtcgagatct ggggtcgatc  18300

agccggggat gcatcaggcc gacagtcgga acttcgggtc cccgacctgt accattcggt  18360

gagcaatgga taggggagtt gatatcgtca acgttcactt ctaaagaaat agcgccactc  18420

agcttcctca gcggctttat ccagcgattt cctattatgt cggcatagtt ctcaagatcg  18480

acagcctgtc acggttaagc gagaaatgaa taagaaggct gataattcgg atctctgcga  18540

gggagatgat atttgatcac aggcagcaac gctctgtcat cgttacaatc aacatgctac  18600

cctccgcgag atcatccgtg tttcaaaccc ggcagcttag ttgccgttct tccgaatagc  18660

atcggtaaca tgagcaaagt ctgccgcctt acaacggctc tcccgctgac gccgtcccgg  18720

actgatgggc tgcctgtatc gagtggtgat tttgtgccga gctgccggtc ggggagctgt  18780

tggctggctg gtggcaggat atattgtggt gtaaacaaat tgacgcttag acaacttaat  18840

aacacattgc ggacgttttt aatgtactgg ggtggttttt cttttcacca gtgagacggg  18900

caacagctga ttgcccttca ccgcctggcc ctgagagagt tgcagcaagc ggtccacgct  18960

ggtttgcccc agcaggcgaa aatcctgttt gatggtggtt ccgaaatcgg caaaatccct  19020

tataaatcaa aagaatagcc cgagataggg ttgagtgttg ttccagtttg gaacaagagt  19080

ccactattaa agaacgtgga ctccaacgtc aaagggcgaa aaaccgtcta tcagggcgat  19140

ggcccactac gtgaaccatc acccaaatca agttttttgg ggtcgaggtg ccgtaaagca  19200

ctaaatcgga accctaaagg gagcccccga tttagagctt gacggggaaa gccggcgaac  19260

gtggcgagaa aggaagggaa gaaagcgaaa ggagcgggcg ccattcaggc tgcgcaactg  19320

ttgggaaggg                                                         19330
```